US011306122B2

(12) United States Patent
Zimering

(10) Patent No.: US 11,306,122 B2
(45) Date of Patent: Apr. 19, 2022

(54) COMPOSITIONS AND METHODS OF INHIBITING THE BINDING OF PLASMA IGG AUTOANTIBODIES TO SEROTONIN 2A RECEPTOR

(71) Applicant: United States Government As Represented By The Department of Veterans Affairs, Washington, DC (US)

(72) Inventor: Mark B. Zimering, Lyons, NJ (US)

(73) Assignee: The United States Government As Represented By The Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/897,071

(22) Filed: Jun. 9, 2020

(65) Prior Publication Data
US 2020/0392185 A1 Dec. 17, 2020

Related U.S. Application Data

(60) Provisional application No. 63/004,107, filed on Apr. 2, 2020, provisional application No. 62/861,595, filed on Jun. 14, 2019.

(51) Int. Cl.
| | | |
|---|---|---|
| *C07K 7/08* | (2006.01) | |
| *A61K 31/517* | (2006.01) | |
| *A61P 3/10* | (2006.01) | |
| *A61K 38/10* | (2006.01) | |
| *A61K 31/445* | (2006.01) | |

(52) U.S. Cl.
CPC .............. *C07K 7/08* (2013.01); *A61K 31/445* (2013.01); *A61K 31/517* (2013.01); *A61K 38/10* (2013.01); *A61P 3/10* (2018.01)

(58) Field of Classification Search
CPC ................................. C07K 7/08; A61K 31/517
See application file for complete search history.

(56) References Cited

U.S. PATENT DOCUMENTS

| | | | |
|---|---|---|---|
| 6,942,963 B1 | 9/2005 | Ingram et al. | |
| 7,067,550 B2 | 6/2006 | Ingram et al. | |
| 7,101,879 B2 | 9/2006 | Ingram et al. | |
| 10,633,427 B2 * | 4/2020 | Paterno | C12Y 106/03001 |
| 10,835,585 B2 * | 11/2020 | Fritsch | A61K 39/001104 |
| 2003/0105152 A1 | 6/2003 | Ingram et al. | |
| 2003/0114510 A1 | 6/2003 | Ingram et al. | |
| 2016/0376340 A1 * | 12/2016 | Paterno | C12Y 106/03001 514/17.9 |
| 2018/0153975 A1 * | 6/2018 | Fritsch | A61K 39/001151 |

FOREIGN PATENT DOCUMENTS

| | | | |
|---|---|---|---|
| EP | 15174144.1 | 6/2015 | |
| EP | 3 109 257 | * 12/2016 | C07K 14/705 |
| WO | WO 2002/035987 | 5/2002 | |
| WO | WO 2003/068147 | 8/2003 | |
| WO | WO 2016/187508 | * 11/2016 | A61K 39/00 |
| WO | PCT/US2020/036792 | 6/2020 | |

OTHER PUBLICATIONS

Aghajanian, GK, et al., Serotonin induces excitatory postsynaptic potentials in apical dendrites of neocortical pyramidal cells. Neuropharmacology. 1997; 36(4-5):589-99.
Aghajanian, GK, et al., Serotonin model of schizophrenia: emerging role of glutamate mechanisms. Brain Res Brain Res Rev. 2000;31(2-3):302-312.
Ansah, TA, et al., The 5-HT2A receptor antagonist M100907 produces antiparkinsonian effects and decreases striatal glutamate. Front Systems Neurosci 2011.
Baker, RA, et al., Constitutively active Gq/11-coupled receptors enable signaling by co-expressed G(i/o)-coupled receptors. J Biol Chem. vol. 2004: 279(7) 5152-5161.
Balakrishnan, K, et al., The phosphoinositide-3-kinase (PI3K)-delta and gamma inhibitor, IPI-145 (Duvelisib), overcomes signals from the PI3K/AKT/S6 pathway and promotes apoptosis in CLL. Leukemia. 2015;29(9):1811-1822.
Benros, ME, et al., Autoimmune diseases and infections as risk factors for schizophrenia. Annals of the New York Academy of Sciences. 2012; 1262:56-66.
Black, J, III, et al., HLA DQB1*0602 positive narcoleptic subjects with cataplexy have CSF IgG reactive to rat hypothalamic protein extract. Sleep 2005; 28: 1191-1192.
Chen, Y, et al., Mechanism of all-trans-retinal toxicity with implications for Stargardt disease and age-related macular degeneration. J Biol Chem. 2012; 287(7):5059-5069.
Corsetti, et al., Effect of dietary fat on the development of non-insulin dependent diabetes mellitus in obese Zucker diabetic fatty male and female rats. Atherosclerosis, Feb. 2000;148(2):231-41.
Crane, PK, et al. Association of Traumatic Brain Injury With Late-Life Neurodegenerative Conditions and Neuropathologic Findings. JAMA Neurol. Sep. 1, 2016; 73(9):1062-9.
Dechend, R, et al., Agonistic autoantibodies to the AT1 receptor in a transgenic rat model of preeclampsia. Hypertension. 2005;45(4):742-6.
Faaber, P, et al. Cross-reactivity of human and murine anti-DNA antibodies with heparan sulfate. The major glycosaminoglycan in glomerular basement membranes. J Clin Invest. Jun. 1986;77(6):1824-30.
Han F, et al., Narcolepsy onset is seasonal and increased following the 2009 H1N1 pandemic in China. Ann Neurol. 2011; 70(3):410-417.
Holthoff, HP, et al. Detection of anti-β1-AR autoantibodies in heart failure by a cell-based competition ELISA. Circ Res. 2012; 111(6):675-84.
Hu, G, et al., Type 2 Diabetes and the Risk of Parkinson's Disease. Diabetes Care 2007; 30(4): 842-847.
Huang, A, et al., Understanding healthcare burden and treatment patterns among young adults with schizophrenia. J Med Econ. Oct. 2018; 21(10):1026-1035.

(Continued)

*Primary Examiner* — Amber D Steele
(74) *Attorney, Agent, or Firm* — Ballard Spahr LLP

(57) ABSTRACT

Disclosed herein, are decoy peptides or polypeptides capable of inhibiting binding of 5-HT2A autoantibodies to a second extracellular loop region of the 5-HT2A receptor, and a pharmaceutical composition containing the decoy peptides or polypeptides and methods of use.

20 Claims, 23 Drawing Sheets
Specification includes a Sequence Listing.

(56) References Cited

OTHER PUBLICATIONS

Jensen, KK, et al., Improved methods for predicting peptide binding affinity to MHC class II molecules. Immunology. 2018;154(3):394-406.
Johnsen, JI, et al., Inhibitors of mammalian target of rapamycin downregulate MYCN protein expression and inhibit neuroblastoma growth in vitro and in vivo. Oncogene. 2008; 27(20):2910-2922.
Kim, A, et al., Determinants of immunodominance for CD4 T cells. Curr Opin Immunol. 2015; 34:9-15.
Kowalski et al., Ontogeny of hyperphagia in the Zucker (fa/fa) rat. Am J. Physiol. Oct. 1998; 275(4):R1106-9.
Luttrell, LM, et al., Activation and targeting of extracellular signal-regulated kinases by betaarrestin scaffolds. Proc Natl Acad Sci USA. 2001;98(5):2449-2454.
Mailian, KR., et al., Concentration and protein composition of circulating immune complexes in the blood of patients with schizophrenia and subjects with positive familial history of disease. Zh. Nevrol. Psikhiatr. Im. S. S. Korsakova 2005; 105: 55-60.
Mignot, E, et al., Complex HLA-DR and -DQ interactions confer risk of narcolepsy-cataplexy in three ethnic groups. Am J Hum Genet. 2001; 68(3):686-99.
Muguruza, C, et al., Group II Metabotropic Glutamate Receptors as Targets for Novel Antipsychotic Drugs. Front Pharmacol. May 20, 2016;7:130.
Nishino, S, et al., Hypocretin (orexin) deficiency in human narcolepsy. Lancet. 2000; 355(9197):39-40.
Nohynek, H, et al., AS03 adjuvanted AH1N1 vaccine associated with an abrupt increase in the incidence of childhood narcolepsy in Finland. PLoS One. 2012; 7(3):e33536.
Passacquale, G, et al., Monocyte-platelet interaction induces a pro-inflammatory phenotype in circulating monocytes. PLoS One. 2011; 6(1 0): e25595.
Patel, PS, et al. The role of the immune system in obesity and insulin resistance. J Obes 2013;2013:616193).
Schizophrenia Working Group of the Psychiatric Genomics Consortium. Biological insights from 108 schizophrenia-associated genetic loci. Nature. Jul. 24, 2014; 511(7510):421-7.
Schmid, CL, et al., Agonist-directed signaling of the serotonin 2A receptor depends on beta-arrestin-2 interactions in vivo. Proc Nail Acad Sci USA. 2008; 105(3):1079-8.
Schmid, CL, and Bohn, LM. Serotonin, but not N-methyltryptamines, activates the serotonin 2A receptor via a ß-arrestin2/Src/Akt signaling complex in vivo. J Neurosci. 2010; 30(40):13513-13524.
Vlodaysky, I, et al., Heparanase: multiple functions in inflammation, diabetes and atherosclerosis. Matrix Biol. Jun. 24, 2013; 32(5):220-2.
Voronova, IP, et al., 5-HT2A receptors control body temperature in mice during LPS-induced inflammation via regulation of NO production. Pharmacol Res. 2016; 103:123-131.
Xu, T, et al., Cellular localization of serotonin (2A) (5HT (2A)) receptors in the rat brain. Brain Res Bull. 2000; 51(6):499-505.
Wacker D, et al. Crystal Structure of an LSD-Bound Human Serotonin Receptor. Cell. 2017; 168(3):377-389.
Walker, KR, and Tesco, G. Molecular mechanisms of cognitive dysfunction following traumatic brain injury. Frontiers in Aging Neuroscience. 2013; 5:29.
Wang, J, et al., Metabotropic glutamate receptor subtype 2 is a cellular receptor for rabies virus. PLoS Pathogens. 2018; 14(7):e1007189.
Wright, C, et al., Detection of multiple autoantibodies in patients with ankylosing spondylitis using nucleic acid programmable protein arrays. Mol Cell Proteomics. 2012; 11(2):M9.00384.
Wu, X, et al., A rare premalignant prostate tumor epithelial cell syndecan-1 forms a fibroblast growth factor-binding complex with progression-promoting ectopic fibroblast growth factor receptor 1. Cancer Res. 2001;61(13):5295-302.
Zimering, MB, Autoantibodies in Type-2 Diabetes having Neurovascular Complications Bind to the Second Extracellular Loop of the 5-Hydroxytryptamine 2A Receptor. Endocrinol Diabetes Metab J. Aug. 2019;3(4) pii: 118. Epub Aug. 14, 2019.
Zimering, MB, Circulating Neurotoxic 5-HT2A Receptor Agonist Autoantibodies in Adult Type 2 Diabetes with Parkinson's Disease, J Endocrinol Diabetes. 2018; 5(2):10.
Zimering, MB, Diabetes Autoantibodies Mediate Neural- and Endothelial Cell-Inhibitory Effects via 5-Hydroxytryptamine-2 Receptor Coupled to Phospholipase C/Inositol Triphosphate/Ca2+ Pathway. J Endocrinol Diabetes. 2017;4(4):1-10.
Zimering, MB et al., Anti-endothelial and anti-neuronal effects from auto-antibodies in subsets of adult diabetes having a cluster of micro vascular complications. Diabetes Res Clin Pract. 2011;93(1):95-105.
Zimering, MB, et al. (2016) Toxic Immunoglobulin Light Chain Autoantibodies are Associated with a Cluster of Severe Complications in Older Adult Type 2 Diabetes. J Endocrinol Diab 3(1): 10.
Zimering, MB, et al. (2015) Autoantibodies in human diabetic depression inhibit adult neural progenitor cells in vitro and induce depressive-like behavior in rodents. J Endocrinol Diab 2015; 2(2):11.
Zimering, MB, et al., (2013) Anti-neurotrophic effects from autoantibodies in adult diabetes having primary open angle glaucoma or dementia. Front. Endocrinol. 4:58.
Zimering, MB, et al., Autoantibodies in type 2 diabetes induce stress fiber formation and apoptosis in endothelial cells. J Clin Endo Metab, 94(6), 2171-2177, 2009.
Zimering, MB, et al., Endothelial cell autoantibodies in predicting declining renal function, endstage renal disease, or death in adult type 2 diabetic nephropathy. Front. Endocrinol. 2014; 5:128.
Zimering, MB, et al., Metabolism. Investigators forthe VADT. Endothelial cell inhibitory autoantibodies are associated with laser photocoagulation in adults from the Veterans Affairs Diabetes Trial. 2009;58(6):882-7.
Alsip, N.L., et al., "Multiple serotonin receptors on large arterioles in striated muscle", Journal of Vascular Research, 1991, vol. 28, No. 6, pp. 537-541.
Bernfield, M., "Syndecan, a developmentally regulated cell surface proteoglycan that binds extracellular matrix and growth factors", Philosophical Transactions of the Royal Society of London, B, Biological Sciences, Mar. 12, 1990, vol. 327, No. 1239, pp. 171-186.
Chen, G., et al., "Inflammatory cytokines and fatty acids regulate endothelial cell heparanase expression", Biochemistry, May 4, 2004, vol. 43, No. 17, pp. 4971-4977.
Fuxe, K., et al., "Receptor heteromerization in adenosine A2A receptor signaling relevance for striatal function and Parkinson's disease", Neurology, Dec. 9, 2003, vol. 61, No. 11, Suppl. 6, pp. S19-S23.
Gonzalez-Maeso, J., et al., "Identification of a serotonin/glutamate receptor complex implicated in psychosis", Nature, Mar. 2008, vol. 452, No. 7183, pp. 93-97.
Hennessy, B.T., et al., "Exploiting the PI3K/AKT pathway for cancer drug discovery", Nature reviews Drug discovery, Dec. 2005, vol. 4, No. 12, pp. 988-1004.
Kosir, M.A., and Quinn, C.C., "Sorting of heparan sulfate proteoglycan into matrix compartments of prostate adenocarcinoma cells", Journal of Surgical Research, Jan. 1, 1995, vol. 58, No. 1, pp. 46-52.
Makino, H., et al., "Heparan sulfate proteoglycans are lost in patients with diabetic nephropathy", Nephron, 1992, vol. 61, No. 4, pp. 415-421.
Michino, M., et al., "What can crystal structures of aminergic receptors tell us about designing subtype-selective ligands?", Pharmacological Reviews, Jan. 1, 2015, vol. 67, No. 1, pp. 198-213.
Moreno, J.L., et al., "Metabotropic glutamate mGlu2 receptor is necessary for the pharmacological and behavioral effects induced by hallucinogenic 5-HT2A receptor agonists", Neuroscience Letters, Apr. 15, 2011, vol. 493, No. 3, pp. 76-79.
Peterson, R.G., et al., "Zucker Diabetic Fatty Rat as a Model for Non-insulin-dependent Diabetes Mellitus", Llar Journal, Jan. 1, 1990, vol. 32, No. 3, pp. 16-19.
Pootanakit, K., et al., "5-HT2a receptors in the rabbit retina: Potential presynaptic modulators", Visual Neuroscience, Mar. 1999, vol. 16, No. 2, pp. 221-230.
Shibata, S., et al., "Autoantibodies to Vascular Heparan Sulfate Proteoglycan in Systemic Lupus Erythematosus React with Endothelial

(56) References Cited

OTHER PUBLICATIONS

Cells and Inhibit the Formation of Thrombin-Antithrombin III Complexes", Clinical Immunology and immunopathology, Feb. 1, 1994, vol. 70, No. 2, pp. 114-123.
Tariq, S.H., et al., "Comparison of the Saint Louis University Mental Status Examination and the Mini-Mental State Examination for Detecting Dementia and Mild Neurocognitive Disorder—A Pilot Study", The American Journal of Geriatric Psychiatry, Nov. 1, 2006, vol. 14, No. 11, pp. 900-910.
Tokuyama, Y., et al., "Evolution of β-Cell Dysfunction in the Male Zucker Diabetic Fatty Rat", Diabetes, Dec. 1, 1995, vol. 44, No. 12, pp. 1447-1457.
Trimble, E.R., et al., "Insulin resistance is accompanied by impairment of amylase-gene expression in the exocrine pancreas of the obese Zucker rat", Biochemical Journal, Aug. 1, 1986, vol. 237, No. 3, pp. 807-812.
Triscari, J., et al., "Carbohydrate metabolism in lean and obese Zucker rats", Metabolism, Feb. 1, 1979, vol. 28, No. 2, pp. 183-189.
Wang, B., et al., "Leptin- and Leptin Receptor-Deficient Rodent Models: Relevance for Human Type 2 Diabetes", Current Diabetes Reviews, Mar. 1, 2014, vol. 10, No. 2, pp. 131-145.
Weiner, D.M., et al., "5-Hydroxytryptamine2A Receptor Inverse Agonists as Antipsychotics", Journal of Pharmacology and experimental therapeutics, Oct. 1, 2001, vol. 299, No. 1, pp. 268-276.
Zimering, M.B., et al., "Low plasma basic fibroblast growth factor is associated with laser photocoagulation treatment in adult type 2 diabetes mellitus from the Veterans Affairs Diabetes Trial", Metabolism, Mar. 1, 2009, vol. 58, No. 3, pp. 393-400.
Zimering, M.B., "Recurrent Macular Edema and Stroke Syndrome in Type 1 Diabetes Mellitus with Potent Endothelial Cell Inhibitory Autoantibodies", Endocrine Practice, Sep. 1, 2010, vol. 16, No. 5, pp. 842-850.
U.S. Appl. No. 62/861,595, filed Jun. 14, 2019, Mark B. Zimering.
U.S. Appl. No. 63/004,107, filed Apr. 2, 2020, Mark B. Zimering.

\* cited by examiner

COMPOSITIONS AND METHODS OF INHIBITING THE BINDING OF PLASMA IGG AUTOANTIBODIES TO SEROTONIN 2A RECEPTOR

CROSS REFERENCE TO RELATED APPLICATIONS

This application claims the benefit of U.S. Provisional Applications No. 62/861,595, filed Jun. 14, 2019; and 63/004,107, filed Apr. 2, 2020. The content of these earlier filed applications is hereby incorporated by reference herein in their entirety.

INCORPORATION OF THE SEQUENCE LISTING

The present application contains a sequence listing that is submitted via EFS-Web concurrent with the filing of this application, containing the file name "37759_0241P1_SL.txt" which is 4,096 bytes in size, created on Apr. 6, 2020, and is herein incorporated by reference in its entirety.

BACKGROUND

Diabetes is associated with an increased risk of serious health problems including certain neurovascular and neurodegenerative complications. Identifying patients with an increased risk and a therapeutic approach to minimize risk or treat neurovascular and neurodegenerative complications disease is needed.

SUMMARY

Described herein are decoy peptides comprising or consisting of the sequence of QDDSKVFKEGSCLLADDN (SEQ ID NO: 1), or a fragment thereof.

Disclosed herein are methods of identifying a subject at risk for developing a neurodegenerative disease, the methods comprising: a) obtaining or having obtained a sample from the subject, wherein the sample comprises one or more 5-hydroxytryptamine 2A receptor autoantibodies (5-HT2A receptor autoantibodies); b) contacting the sample of step a) with one or more decoy peptides comprising the sequence of QDDSKVFKEGSCLLADDN (SEQ ID NO: 1). SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more of the decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); and d) identifying the subject at risk for developing a neurodegenerative disease when the level of binding in step c) is higher when compared to the level of binding in a reference sample.

Disclosed herein are methods of identifying a subject at risk for developing a neurodegenerative disease, wherein the subject has refractory hypertension, obesity, or type 2 diabetes, the methods comprising: a) obtaining or having obtained a sample from the subject, wherein the sample comprises one or more 5-hydroxytryptamine 2A receptor autoantibodies (5-HT2A receptor autoantibodies); b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more of the decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); and d) identifying the subject at risk for developing a neurodegenerative disease when the level of binding in step c) is higher when compared to the level of binding in a reference sample.

Disclosed herein are methods of identifying a subject at risk for developing a neurodegenerative disease, wherein the subject does not have or has not been diagnosed with refractory hypertension, obesity, or type 2 diabetes, the methods comprising: a) obtaining or having obtained a sample from the subject, wherein the sample comprises one or more 5-hydroxytryptamine 2A receptor autoantibodies (5-HT2A receptor autoantibodies); b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more of the decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); and d) identifying the subject at risk for developing a neurodegenerative disease when the level of binding in step c) is higher when compared to the level of binding in a reference sample.

Disclosed herein are methods of identifying a subject at risk for developing a neurodegenerative disease, wherein the subject has a traumatic brain injury, the methods comprising: a) obtaining or having obtained a sample from the subject, wherein the sample comprises one or more 5-hydroxytryptamine 2A receptor autoantibodies (5-HT2A receptor autoantibodies); b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more of the decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); and d) identifying the subject at risk for developing a neurodegenerative disease when the level of binding in step c) is higher when compared to the level of binding in a reference sample.

Disclosed herein are methods of identifying a subject at risk for developing a neurodegenerative disease, wherein the subject has a traumatic brain injury, the methods comprising: a) obtaining or having obtained a sample from the subject, wherein the sample comprises one or more 5-hydroxytryptamine 2A receptor autoantibodies (5-HT2A receptor autoantibodies); b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more of the decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); and d) identifying the subject at risk for developing a neurodegenerative disease when the level of binding in step c) is higher when compared to the level of binding in a reference sample.

Disclosed herein are methods of treating a subject at risk for developing a neurodegenerative disease, wherein the subject has a traumatic brain injury, the methods comprising: a) obtaining or having obtained a sample from the subject, wherein the sample comprises one or more 5-hydroxytryptamine 2A receptor autoantibodies (5-HT2A receptor autoantibodies); b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more of the decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); d) identifying the subject at risk for developing a neurodegenerative disease when the level of binding in step c) is higher when compared to the level of binding in a reference sample; and e) administering to the subject a therapeutically effective amount of a 5-HT2A receptor antagonist.

Disclosed herein are methods of competitively inhibiting the binding of 5-hydroxytryptamine 2A receptor autoantibodies to a second extracellular loop region of the 5-HT2A receptor, the methods comprising: administering to a subject a therapeutically effective amount of one or more decoy peptides comprising or consisting of the amino acid sequence of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1), or a fragment thereof.

Disclosed herein are methods of lowering blood pressure in a subject, the methods comprising: administering to a subject a therapeutically effective amount of one or more of the decoy peptides or polypeptides comprising or consisting of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof.

Disclosed herein are methods of preventing or reducing one or more symptoms of kidney disease or the risk of developing kidney disease in a subject, the methods comprising: administering to a subject a therapeutically effective amount of one or more of the decoy peptides or polypeptides comprising or consisting of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof can be administered to the subject.

Disclosed herein are methods of identifying a subject at risk for or developing retinal degeneration, the methods comprising: a) obtaining or having obtained a sample from the subject, wherein the sample can comprise one or more 5-HT2A receptor autoantibodies; b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); and d) identifying the subject at risk for developing a retinal degeneration when the level of binding in step c) is higher when compared to the level of binding in a reference sample.

Disclosed herein are methods of treating a subject having or at risk for developing retinal degeneration, the methods comprising: a) obtaining or having obtained a sample from the subject, wherein the sample can comprise one or more 5-HT2A receptor autoantibodies; b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more of the decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); d) identifying the subject at risk for developing a retinal degeneration when the level of binding in step c) is higher when compared to the level of binding in a reference sample; and e) administering to the subject a therapeutically effective amount of a 5-HT2A receptor antagonist.

BRIEF DESCRIPTION OF THE DRAWINGS

FIG. 4A shows protein-A eluate fraction in representative TBI patient incubated with N2A cells for 24 hours at indicated dilutions. Cell survival was determined with MTT assay. FIG. 4B shows that a one-fiftieth dilution of the protein-A eluate fraction from eight different TBI plasmas was incubated with N2a cells in the presence or absence of the selective 5-HT2AR receptor antagonist M100907 (250 nM) or the alpha-1 adrenergic receptor antagonist prazosin (850 nM)(n=5 patients). Cell survival (after 24 hours) was determined using MIT assay. *$P<0.01$ compared to TBI 5-HT2A receptor autoantibodies alone.

FIG. 5B shows protein-A eluate in type 2 diabetic dementia patient having multiple microvascular complications bind with high potency and titer to both 5-HT2AR peptide and to purified neuronal-cell derived heparan sulfate proteoglycan (HSPG).

FIG. 7A shows the dose-dependence of acute N2A neurite retraction by the autoantibodies from two older diabetic patients not suffering with diabetic microvascular complications or any neuropsychiatric or neurodegenerative complication (open bars). FIG. 7B shows time-dependent acute neurite retraction induced by diabetic schizophrenia plasma autoantibodies (solid bars; Pt 1). Results represent mean±SE. Similar results were obtained in the plasma autoantibodies from five of five schizophrenia patients tested.

FIG. 8A shows LY379268 potentiates IgG neurite retraction diabetic schizophrenia Pt plasma autoantibodies in N2A cells. FIG. 8B shows LY379268 potentiates neurite retraction by the hallucinogen DOI. DOI was incubated at the indicated concentrations in the presence (orange symbol) or absence (blue symbol) of a 10 micromolar concentration of LY379268 in N2A cells. Each point represents mean acute neurite retraction which varied by <10%. In FIG. 8A, a similar result was obtained in the diabetic schizophrenia Pt 2 plasma autoantibodies.

FIG. 10A shows that plasma autoantibodies in three patients with schizophrenia (solid line), four patients with another disorder (dotted line), or a patient with diabetes and discoid lupus (dashed line) were incubated with N2A cells at the indicated concentrations for 24 hours. Each point represents mean N2A cell survival, i.e., quadruplicate determinations which varied by <10%. *P<0.01 compared to solid line or dotted line. FIG. 10B shows that patient 1 diabetic schizophrenia autoantibodies (60 nM) was incubated alone (solid bars) or with a 200 nanomolar (speckled bar) or a 500 nanomolar concentration (open bar) of the selective 5-HT2AR antagonist M100907 in N2A cells for 24 hours. Results are mean±SE.

FIG. 11A shows that Patient 1's schizophrenia plasma autoantibodies (40 nM) were incubated alone (solid bar) or with (speckled bar) a 5 micromolar concentration of the mGlu2R agonist LY379268 in N2A cells for 24 hours. Similar results were obtained in the plasma autoantibodies from Pt 2 chronic schizophrenia, and a Parkinson's disease patient who had been experiencing visual hallucinations. FIG. 11B shows that Patient 2's chronic schizophrenia plasma autoantibodies (40 nM) were incubated alone (solid bar) or with (speckled bar) a 100 ng/mL concentration of pertussis toxin (PTX) in N2A cells for 24 hours. A-B) Results are mean±SE.

FIG. 24A shows the trajectory of body weight change in Zucker diabetic fatty rats given saline. FIG. 24B shows the trajectory of body weight change in Zucker diabetic fatty rats given peptide injections (SEQ ID NO: 2). Solid bars indicate peptide (2 mg/kg) or saline, alternate days for 7 days.

FIG. 25A shows that beginning at 11-weeks of age, the two groups of ZDF rats did not differ significantly in their baseline body weight determined at 9 weeks of age. FIG. 25B shows the two groups of ZDF rats differed significantly in their baseline mean random blood glucose concentration.

FIG. 26A shows age-associated changes in body mass. FIG. 26B shows age-associated changes in blood glucose.

DETAILED DESCRIPTION

Figure 1:
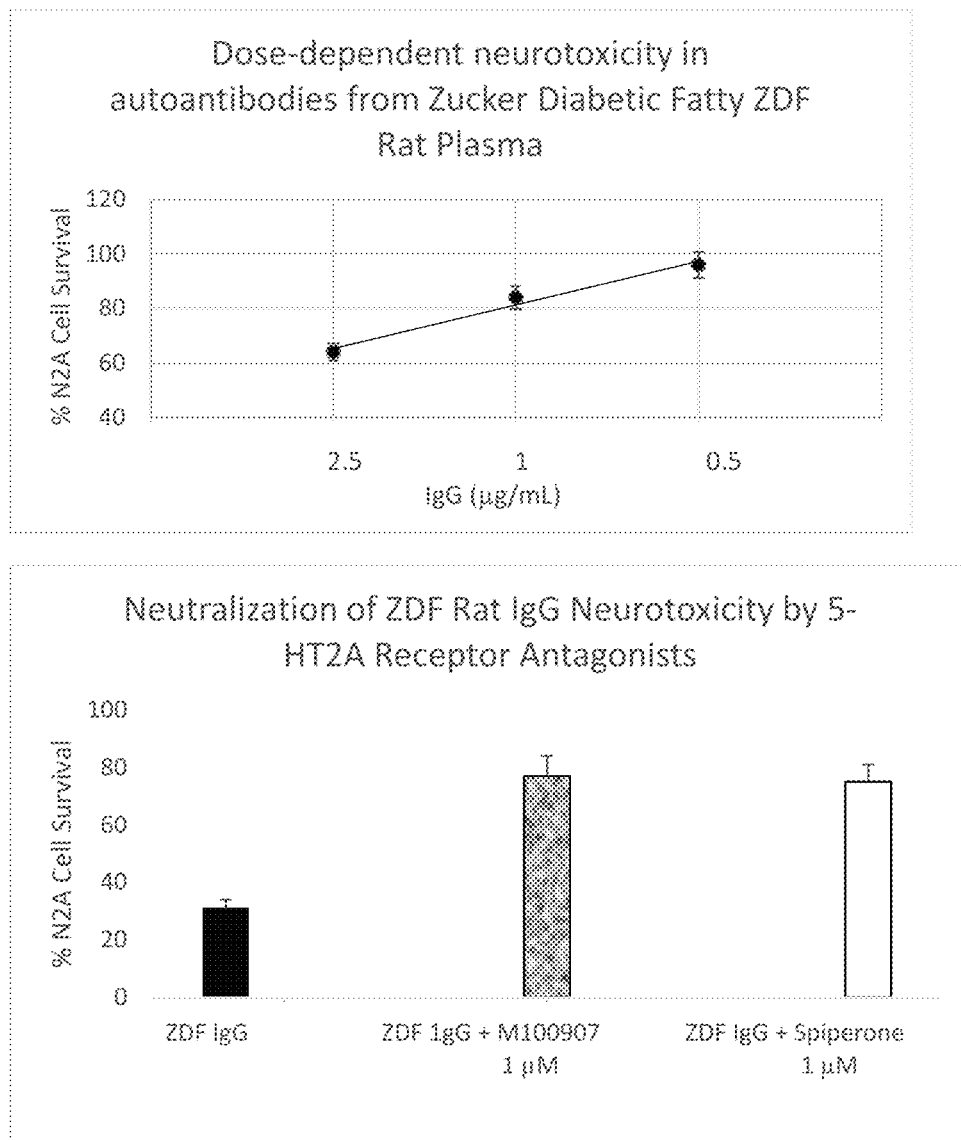
FIG. 1 shows dose-dependent neurotoxicity in the protein G eluate fraction of ZDF rat plasma (top panel), and significant protection against IgG autoantibody-induced neurotoxicity by co-incubation with selective and/or potent 5-HT2A receptor antagonists, M100907 and spiperone (bottom panel).

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment, such as, for example, prior to the administering step.

As used herein, the term "comprising" can include the aspects "consisting of" and "consisting essentially of."

As used herein the terms "amino acid" and "amino acid identity" refers to one of the 20 naturally occurring amino acids or any non-natural analogues that may be in any of the antibodies, variants, or fragments disclosed. Thus "amino acid" as used herein means both naturally occurring and synthetic amino acids. For example, homophenylalanine, citrulline and norleucine are considered amino acids for the purposes of the invention. "Amino acid" also includes amino acid residues such as proline and hydroxyproline. The side chain may be in either the (R) or the (S) configuration. In some aspects, the amino acids are in the D- or L-configuration. If non-naturally occurring side chains are used, non-amino acid substituents may be used, for example to prevent or retard in vivo degradation.

"Inhibit," "inhibiting" and "inhibition" mean to diminish or decrease an activity, level, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in some aspects, the inhibition or reduction can be a 10, 20, 30, 40, 50, 60, 70, 80, 90, 100%, or any amount of reduction in between as compared to native or control levels. In some aspects, the inhibition or reduction is 10-20, 20-30, 30-40, 40-50, 50-60, 60-70, 70-80, 80-90, or 90-100% as compared to native or control levels. In some aspects, the inhibition or reduction is 0-25, 25-50, 50-75, or 75-100% as compared to native or control levels.

"Treatment" and "treating" refer to administration or application of a therapeutic agent (e.g., a decoy peptide or polypeptide described herein) to a subject or performance of a procedure or modality on a subject for the purpose of obtaining a therapeutic benefit of a disease or health-related condition. For example, a treatment may include administration of a pharmaceutically effective amount of a decoy peptide or polypeptide that inhibits the binding of 5-HT2A autoantibodies to a second extracellular loop region of the 5-HT2A receptor.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. For example, the disease, disorder, and/or condition can be neurologic disease or disorder or microvascular disease or disorder or a neurodegenerative disease or disorder. In some aspects, the subject has type 2 diabetes, microvascular angiopathy, diabetic kidney disease, Parkinson's disease, dementia, major depressive disorder, obesity, refractory hypertension, essential hypertension or has had a stroke or a traumatic brain injury or a combination thereof.

The term "fragment" can refer to a portion (e.g., at least 4, 5, 6, 7, 8, 9, 10, 11, 12, 13, 14, 15, 16, 17, etc. amino acids) of a peptide that is substantially identical to a reference peptide and retains the biological activity of the reference. In some aspects, the fragment or portion retains at least 50%, 75%, 80%, 85%, 90%, 95% or 99% of the biological activity of the reference peptide described herein. Further, a fragment of a referenced peptide can be a continuous or contiguous portion of the referenced polypeptide (e.g., a fragment of a peptide that is ten amino acids long can be any 2-9 contiguous residues within that peptide).

A "variant" can mean a difference in some way from the reference sequence other than just a simple deletion of an N- and/or C-terminal amino acid residue or residues. Where the variant includes a substitution of an amino acid residue, the substitution can be considered conservative or non-conservative. Conservative substitutions are those within the following groups: Ser, Thr, and Cys; Leu, ILe, and Val; Glu and Asp; Lys and Arg; Phe, Tyr, and Trp; and Gln, Asn, Glu, Asp, and His. Variants can include at least one substitution and/or at least one addition, there may also be at least one deletion. Variants can also include one or more non-naturally occurring residues. For example, they may include selenocysteine (e.g., seleno-L-cysteine) at any position, including in the place of cysteine. Many other "unnatural" amino acid substitutes are known in the art and are available from commercial sources. Examples of non-naturally occurring amino acids include D-amino acids, amino acid residues having an acetylaminomethyl group attached to a sulfur atom of a cysteine, a pegylated amino acid, and omega amino acids of the formula $NH_2(CH_2)_nCOOH$ wherein n is 2-6 neutral, nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties of proline.

As used herein, the term "prevent" or "preventing" refers to preventing in whole or in part, or ameliorating or controlling.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

Diabetes is associated with a substantially increased risk of certain neurovascular and neurodegenerative complications, e.g., stroke, dementia, Parkinson's disease, major depressive disorder (Hu G, et al, *Diabetes Care* 2007; 30(4): 842-847), through complex and as yet poorly-defined mechanisms. Activation of 5-HT2A receptor IgG autoantibodies in plasma or serum from older adult diabetes suffering with major depressive disorder (Zimering M B, *J Endocrinol Diabetes*. 2018; 5(2)), Parkinson's disease or dementia (Zimering M B, *J Endocrinol Diabetes*. 2017; 4(4)), was identified. Acute neurite retraction and accelerated mouse neuroblastoma N2a cell death induced by the autoantibodies in cell culture was partially or completely prevented by co-incubation (of IgG autoantibodies) with selective antagonists of the 5-HT2A receptor (Zimering M B, *J Endocrinol Diabetes*. 2018; 5(2); and Zimering M B, *J Endocrinol Diabetes*. 2017; 4(4)).

Zucker fatty rats have a mutated leptin receptor (Phillips et al., 1996) leading to hyperphagia (Kowalski et al., 1998) with obesity apparent from around 4 weeks of age (Wang et al., 2014). They are hyperinsulinemic (Trimble et al., 1986) and have poor glucose tolerance (Triscari et al., 1979) although are not overtly diabetic. The Zucker diabetic fatty (ZDF) rat is a substrain of the Zucker fatty rat, which was derived from hyperglycemic Zucker fatty rats to gain a model with diabetic features (Peterson et al., 1990). It is severely insulin resistant and males become overtly diabetic at 8-10 weeks, which is due to an inability of beta cells to compensate for insulin resistance, which is associated with changes in islet morphology (Tokuyama et al., 1995). Females do not tend to develop overt diabetes but diabetes can be induced by feeding a high-fat diet (Corsetti et al., 2000). As disclosed herein, the Zucker rat strain can be used to study the bioactivity of the 5-HT2AR autoantibodies. The 5-HT2A receptor is present in both Zucker diabetic fatty rats and in lean Zucker rats at early ages, however, the 5-HT2AR autoantibodies persists into mature adulthood (e.g., 25 weeks of age). The heterozygous lean (fa/+) Zucker rat has twice as high level of 5-HT2AR autoantibody as in ZDF rat. The presence of the 5-HT2AR autoantibody at some stage of development in the three Zucker subtypes: (fatty, diabetic), (lean heterozygous), and (lean lacking a known leptin receptor mutation) suggests 5-HT2AR autoantibody is a Zucker strain 'trait.' The Zucker lean rat described herein and used in the Examples described herein lack a known leptin receptor mutation. As the neurotoxic bioactivity of the 5-HT2AR autoantibody in ZDF rats have properties that resemble those of the agonist 5-HT2AR-targeting autoantibody in humans, the ZDF rat model can be used to study the effects of the compositions (e.g. decoy peptides) disclosed herein.

The second extracellular loop region of several different G-protein coupled receptors lies adjacent to the receptors' orthosteric binding pocket (Wacker D, et al. *Cell.* 2017; 168(3):377-389). For example, the second extracellular loop region of the 5-HT2A receptor is located near the orthosteric binding pocket. Autoantibody binding in this region of the second extracellular loop may induce a conformational change causing receptor activation. In subsets of human dilated cardiomyopathy (Holthoff H P, et al. *Circ Res.* 2012; 111(6):675-84) or in eclampsia (Dechend R, et al., *Hypertension.* 2005; 45(4):742-6), spontaneously-occurring autoantibodies which targeted the second extracellular loop region of the beta-1-adrenergic or the angiotensin 2, type 1 receptor, respectively, caused G-protein coupled receptor activation. Described herein are the results of a study that tested whether IgG autoantibodies in older adult diabetics having angiopathic and/or neurodegenerative complications causes 5-HT2A receptor activation via binding to the second extracellular loop region of the 5-HT2A receptor.

The 5-HT2A receptor is highly expressed in specific brain regions underlying cognition, perception and mood regulation (Xu T, et al., *Brain Res Bull.* 2000; 51(6):499-505). It is also expressed on vascular smooth muscle cells where it plays a role in the regulation of arterial vascular tone (Alsip N, L, et al., *J Vasc Res* 1991; 28:537-541). Autoantibodies capable of targeting the 5-HT2A receptor in the central nervous system and the peripheral vasculature could serve as a biomarker for many disease complications associated with refractory hypertension (e.g., stroke, chronic kidney disease) and/or neurodegeneration (dementia, Parkinson's disease, macular degeneration, retinal degeneration).

Compositions

Disclosed herein are compositions, including pharmaceutical compositions capable of inhibiting autoantibodies from binding to the second extracellular loop region of the 5-hydroxytryptamine 2A (5-HT2A) receptor and activating the 5-HT2A receptor. Also, disclosed herein are compositions capable of preventing or reducing the risk of a neurologic disease or a microvascular disease in a subject. In some aspects, the subject has type 2 diabetes, microvascular angiopathy, diabetic kidney disease, Parkinson's disease, dementia, major depressive disorder, obesity, refractory hypertension, essential hypertension or has had a stroke or a traumatic brain injury or a combination thereof. In some aspects, the subject has type 2 diabetes. In some aspects, the subject does not have or has not been diagnosed with type 2 diabetes, microvascular angiopathy, diabetic kidney disease, Parkinson's disease, dementia, major depressive disorder, obesity, refractory hypertension, essential hypertension or has had a stroke or a traumatic brain injury or a combination thereof. In some aspects, the compositions disclosed herein are capable of preventing or reducing cognitive decline (cognitive dysfunction including changes in memory), mood, or one or symptoms associated with depression in a subject. In some aspects, the subject has type 2 diabetes and a traumatic brain injury. In some aspects, the subject was diagnosed with type 2 diabetes before the traumatic brain injury. In some aspects, the subject has a traumatic brain injury. In some aspects, the subject does not have or has not been diagnosed with type 2 diabetes.

Disclosed herein are decoy peptides or polypeptides that can comprise or consist of the amino acid sequence of QDDSKVFKEGSCLLADDN (SEQ ID NO: 1), or a fragment thereof. In some aspects, the fragment of SEQ ID NO: 1 can be between 4 and 9 amino acids in length. Disclosed herein are decoy peptides or polypeptides that can comprise or consist of the amino acid sequence of QDDSKVFKEGSCLLADDN (SEQ ID NO: 1), or a variant thereof. In some aspects, the decoy peptide or polypeptide comprises or consists of the amino acid sequence of SCLLADDN (SEQ ID NO: 2), QDDSKVF (SEQ ID NO: 3), or VFKEGSC (SEQ ID NO: 4). In some aspects, the decoy peptide or polypeptide comprises or consists of the amino acid sequence of SCLLADDN (SEQ ID NO: 2), QDDSKVF (SEQ ID NO: 3), VFKEGSC (SEQ ID NO: 4) or variants thereof. In some aspects, the decoy peptide or polypeptide can inhibit the binding of 5-HT2A receptor autoantibodies to a second extracellular loop region of the 5-HT2A receptor. In some aspects, the decoy peptide or polypeptide can inhibit the binding of 5-HT2A receptor autoantibodies to a second extracellular loop region of the 5-HT2A receptor by competitive inhibition. In some aspects, the decoy peptide or polypeptide can inhibit the binding of 5-HT2A IgG receptor autoantibodies to a second extracellular loop region of the 5-HT2A receptor. In some aspects, the decoy peptide or polypeptide can inhibit the binding of a 5-HT2A IgG receptor autoantibodies to a second extracellular loop region of the 5-HT2A receptor by competitive inhibition. In some aspects, the decoy peptide or polypeptide can bind to the 5-HT2A receptor autoantibody. In some aspects, the decoy peptide or polypeptide can bind to the 5-HT2A receptor IgG autoantibody, Disclosed herein are decoy peptides or polypeptides that can comprise fragments of QDDSKVFKEGSCLLADDN (SEQ ID NO: 1). In some aspects, the fragments thereof can comprise a sequence having at least 20%, 30%, 40%, 50%, 60%, 70%, 80%, 90%, 95%, 98%, 99% identity to SEQ ID NO: 1. In some aspects, the fragment or portion retains at least 50%, 75%, 80%, 85%, 90%, 95% or 99% of the biological activity of the reference protein described herein.

Disclosed herein are decoy peptides or polypeptides that can comprise variants of QDDSKVFKEGSCLLADDN (SEQ ID NO: 1). In some aspects, the variants can comprise a sequence having at least 20%, 30%, 40%, 50%, 60%, 70%, 80%, 90%, 95%, 98%, 99% identity to SEQ ID NO: 1. In some aspects, the variants retains at least 50%, 75%, 80%, 85%, 90%, 95% or 99% of the biological activity of the reference protein described herein.

Disclosed herein are decoy peptides or polypeptides that can comprise variants of SCLLADDN (SEQ ID NO: 2), QDDSKVF (SEQ ID NO: 3), or VFKEGSC (SEQ ID NO: 4). In some aspects, the variants can comprise a sequence having at least 20%, 30%, 40%, 50%, 60%, 70%, 80%, 90%, 95%, 98%, 99% identity to SEQ ID NO: 1, SEQ ID NO: 2, SEQ ID NO: 3 or SEQ ID NO: 4. In some aspects, the variants retains at least 50%, 75%, 80%, 85%, 90%, 95% or 99% of the biological activity of the reference protein described herein.

As used herein, the term "peptide" refers to a linear molecule formed by binding amino acid residues to each other via peptide bonds. As used herein, the term "polypeptide" refers to a polymer of (the same or different) amino acids bound to each other via peptide bonds.

As used herein, the term "decoy peptide or polypeptide" refers to a peptide or polypeptide designed to contain a partial peptide sequence in the second extracellular loop region of the 5-HT2A receptor, and the decoy peptide or polypeptide can block the action of 5-HT2A receptor autoantibodies by binding to the 5-HT2A receptor autoantibodies. In some aspects, the 5-HT2A receptor autoantibodies can be IgG autoantibodies. For example, in some aspects, the decoy peptide or polypeptide can compete with the 5-HT2A receptor present, for instance, on cell surfaces of neurons and vascular cells, for binding to the soluble 5-HT2A receptor autoantibodies or 5-HT2A receptor IgG autoantibodies.

The term "competitive inhibition" as used herein with reference to a decoy peptide or polypeptide can refer to an inhibition of the binding of 5-HT2A receptor autoantibodies to the 5-HT2A receptor by binding to the 5-HT2A receptor autoantibodies. In some aspects, the decoy peptides or polypeptides disclosed herein can bind to the 5-HT2A receptor autoantibodies and as such that it competes with the second extracellular loop region of the 5-HT2A receptor. The 5-HT2A receptor is the targeting region for the 5-HT2A receptor autoantibodies present in the circulation.

In some aspects, the decoy peptide or polypeptide can be of any length so long as the binding of the 5-HT2A receptor autoantibodies to the second extracellular loop region of the 5-HT2A receptor is blocked or inhibited.

In some aspects, the decoy peptides or polypeptides described herein can further comprise 1, 2, 3, 4, 5, 10, 15, 20, 25, 30, 35, 40, 45, 50 amino acid residues at the N-terminal end of the disclosed decoy peptides or polypeptides. In some aspects, the decoy peptides or polypeptides described herein can further comprise 1, 2, 3, 4, 5, 10, 15, 20, 25, 30, 35, 40, 45, 50 amino acid residues at the C-terminal end of the disclosed decoy peptides or polypeptides disclosed herein. In some aspects, the amino acid residues that can be present at either the N-terminal end or the C-terminal end of any of the decoy peptides or polypeptides disclosed herein can be unimportant for inhibiting the binding of the 5-HT2A receptor autoantibodies which bind to the second extracellular loop region of the 5-HT2A receptor. In some aspects, the amino acid residues added to the N-terminal end or the C-terminal end of the decoy peptides or polypeptides disclosed herein may prevent ubiquitination, improve stability, help maintain the three dimensional structure of the peptide, or a combination thereof.

In some aspects, the decoy peptides or polypeptides disclosed herein can further comprise a peptide or polypeptide having one or more amino acid residues with a modified side chain. In some aspects, one or more amino acids of any of the decoy peptides or polypeptides disclosed here can have a modified side chain. Examples of side chain modifications include but are not limited to modifications of amino acid groups, such as reductive alkylation; amidination with methylacetimidate; acylation with acetic anhydride; carbamolyation of amino groups with cynate; trinitrobenzylation of amino acid with 2,4,6-trinitrobenzene sulfonic acid (TNBS); alkylation of amino groups with succinic anhydride; and pyridoxylation with pridoxal-5-phosphate followed by reduction with $NaBH_4$.

In some aspects, the guanidine group of the arginine residue may be modified by the formation of a heterocyclic condensate using a reagent, such as 2, 3-butanedione, phenylglyoxal, and glyoxal. In some aspects, the carboxyl group may be modified by carbodiimide activation via O-acylisourea formation, followed by subsequent derivatization, for example, to a corresponding amide.

In some aspects, the sulfhydryl group may be modified by methods, such as carboxymethylation with iodoacetic acid or iodoacetamide; performic acid oxidation with cysteic acid; formation of mixed disulfides by other thiol compounds; a reaction by maleimide, maleic anhydride, or other substituted maleimide; formation of mercury derivatives using 4-chloromercuribenzoate, 4-chloromercuriphenylsulfonic acid, phenylmercury chloride, 2-chloromercuri-4-nitrophenol, and other mercurial agents; and carbamolyation with cyanate at alkaline pH. In addition, the sulfhydryl group of cysteine may be substituted with a selenium equivalent, whereby a diselenium bond may be formed instead of at least one disulfide bonding site in the peptide.

In some aspects, the tryptophan residue may be modified by, for example, oxidation with N-bromosuccinimide or alkylation of the indole ring by 2-hydroxy-5-nitrobenzyl bromide or sulfonyl halide. Meanwhile, the tyrosine residue may be modified by nitration using tetranitromethane to form a 3-nitrotyrosine derivative.

In some aspects, the modification of the imidazole ring of the histidine residue may be accomplished by alkylation with an iodoacetic acid derivative or N-carbethoxylation with diethylpyrocarbonate.

In some aspects, the proline residue may be modified by, for example, hydroxylation at the 4-position.

In some aspects, the decoy peptides or polypeptides described herein can be further modified to improve stability. In some aspects, any of the amino acid residues of the decoy peptides or polypeptides described herein can be modified to improve stability. In some aspects, decoy peptide or polypeptide can have at least one amino acid residue that has an acetyl group, a fluorenylmethoxy carbonyl group, a formyl group, a palmitoyl group, a myristyl group, a stearyl group, or polyethylene glycol. In some aspects, an acetyl protective group can be bound to the decoy peptide or polypeptide described herein.

As used herein, the term "stability" refers to storage stability (e.g., room-temperature stability) as well as in vivo stability. The foregoing protective group can protect the decoy peptides or polypeptides described herein from the attack of protein cleavage enzymes in vivo.

As used herein, the term "decoy peptide or polypeptide" can also be used to include functional equivalents of the decoy peptides or polypeptides described herein. As used herein, the term "functional equivalents" can refer to amino acid sequence variants having an amino acid substitution, addition, or deletion in some of the amino acid sequence of the decoy peptide or polypeptide while simultaneously having similar or improved biological activity, compared with the decoy peptide or polypeptide as described herein. In some aspects, the amino acid substitution can be a conservative substitution. Examples of the naturally occurring amino acid conservative substitution include, for example, aliphatic amino acids (Gly, Ala, and Pro), hydrophobic amino acids (Ile, Leu, and Val), aromatic amino acids (Phe, Tyr, and Trp), acidic amino acids (Asp and Glu), basic amino acids (His, Lys, Arg, Gln, and Asn), and sulfur-containing amino acids (Cys and Met). In some aspects, the amino acid deletion can be located in a region that is not directly involved in the activity of the decoy peptide and polypeptide disclosed herein.

In some aspects, the amino acid sequence of the decoy peptides or polypeptides described herein can include a peptide sequence that has substantial identity to any of the sequences of the decoy peptides or polypeptides disclosed herein. As used herein, the term "substantial identity" means that two amino acid sequences, when optimally aligned and then analyzed by an algorithm normally used in the art, such as BLAST, GAP, or BESTFIT, or by visual inspection, share at least about 60%, 70%, 80%, 85%, 90%, or 95% sequence identity. Methods of alignment for sequence comparison are known in the art.

In some aspects, the amino acid sequence of the decoy peptides or polypeptides described herein can include a peptide sequence that has some degree of identity or homology to any of sequences of the decoy peptides or polypeptides disclosed herein. The degree of identity can vary and be determined by methods known to one of ordinary skill in the art. The terms "homology" and "identity" each refer to sequence similarity between two polypeptide sequences. Homology and identity can each be determined by comparing a position in each sequence which can be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. The decoy peptides or polypeptides described herein can have at least or about 25%, 50%, 65%, 75%, 80%, 85%, 90%, 95%, 96%, 97%, 98%, or 99% identity or homology to the decoy peptide or polypeptide, wherein the decoy peptide or polypeptide is one or more of SEQ ID NOs: 1-4.

In some aspects, the decoy peptides or polypeptides described herein can be further conjugated to an Fc fragment of immunoglobulin G. In some aspects, the Fc fragment of immunoglobulin G can bind to (and remove) bound 5-HT2A receptor autoantibodies on cells.

In some aspects, the decoy peptides or polypeptides described herein can be part of a scaffold protein. Disclosed herein are scaffold proteins comprising: a SH3 (src homolog3), SH2 (src homolog2), PDZ, or GTPase-binding domain (GBD) and a heterologous peptide. In some aspects, the heterologous peptide can be inserted or connected to one or more of a SH3 (src homolog3), SH2 (src homolog2), PDZ, or GTPase-binding domain (GBD). In some aspects, the heterologous peptide can be one or more of the decoy peptides or polypeptides disclosed herein. In some aspects, the heterologous peptide can comprise or consist of one or more decoy peptides comprising the sequence of QDD-SKVFKEGSCLLADDN (SEQ ID NO: 1), or a fragment thereof, SCLLADDN (SEQ ID NO: 2), QDDSKVF (SEQ ID NO: 3), or VFKEGSC (SEQ ID NO: 4). In some aspects, the heterologous peptide can comprise or consist of one or more decoy peptides comprising a variant of the sequence of QDDSKVFKEGSCLLADDN (SEQ ID NO: 1), SCL-LADDN (SEQ ID NO: 2), QDDSKVF (SEQ ID NO: 3), or VFKEGSC (SEQ ID NO: 4). In some aspects, the scaffold protein is capable of inhibiting the binding of 5-HT2A receptor autoantibodies to a second extracellular loop region of the 5-HT2A receptor. In some aspects, the scaffold protein can inhibit the binding of 5-HT2A receptor autoantibodies to a second extracellular loop region of the 5-HT2A receptor by competitive inhibition. In some aspects, the heterologous peptide of the scaffold can bind to PDZ via the carboxy terminal region of the decoy peptide or polypeptide. In some aspects, the heterologous peptide of the scaffold can be bound to SH3, SH2 or PDZ via a linker. In some aspects, the linker can be positioned between SH3, SH2 or PDZ and the N-terminus of the heterologous peptide. In some aspects, the linker can be designed to comprise the consensus motif of SH3, SH2 or PDZ. For example, PDZ targets the consensus motif Glu-(Ser/Thr)-Xaa-Val/Ile (SEQ ID NO: 7, wherein Xaa can represent any amino acid. SH3, SH2, PDZ or GBD can bind to the linker-heterologous peptide via the condense motif present in the linker.

Pharmaceutical Compositions

As disclosed herein, are pharmaceutical compositions, comprising one or more of the decoy peptides or polypeptides described herein. Also disclosed herein, are pharmaceutical compositions, comprising one or more of the decoy peptides or polypeptides described herein and a pharmaceutical acceptable carrier. Further disclosed herein are pharmaceutical compositions for reducing or preventing acute neurite retraction or preventing accelerated neuron loss. Also disclosed herein are pharmaceutical compositions for reducing the risk of a neurologic disease or disorder or microvascular disease or disorder or a neurodegenerative disease or disorder. In some aspects, the pharmaceutical compositions can comprise: a) a therapeutically effective amount of one or more of the decoy peptides or polypeptides described herein; and b) a pharmaceutically acceptable carrier. In some aspects, the decoy peptides described herein can inhibit the binding of 5-HT2A receptor autoantibodies to a second extracellular loop region of the 5-HT2A receptor. In some aspects, the decoy peptides described herein can inhibit the binding of 5-HT2A receptor autoantibodies to a second extracellular loop region of the 5-HT2A receptor by competitive inhibition.

The pharmaceutical compositions described above can be formulated to include a therapeutically effective amount of a decoy peptide of polypeptide. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a type of neurologic disease or disorder or microvascular disease or disorder.

The pharmaceutical compositions described herein can be administered to the subject (e.g., a human patient) in an amount sufficient to delay, reduce, or preferably prevent the onset of clinical disease. Accordingly, in some aspects, the patient can be a human patient. In therapeutic applications, compositions can be administered to a subject (e.g., a human patient) already with or diagnosed with type 2 diabetes (or to a subject that is not diagnosed with type 2 diabetes or to a subject that does not have type 2 diabetes) in an amount sufficient to at least partially improve a sign or symptom or to inhibit the progression of (and preferably arrest) the symptoms of the condition, its complications, and consequences (e.g., developing a neurologic disease or disorder or microvascular disease or disorder or neurodegenerative disease or disorder). In some aspects, the compositions can be administered to a subject (e.g., a human patient) already with or diagnosed with a traumatic brain injury with or without a diagnosis of type 2 diabetes in an amount sufficient to at least partially improve a sign or symptom or to inhibit the progression of (and preferably arrest) the symptoms of the condition, its complications, and consequences (e.g., developing a neurologic disease or disorder or microvascular disease or disorder or a neurodegenerative disorder). An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effect amount includes amounts that provide a treatment in which the onset or progression of acute neurite retraction, accelerated neuron loss, a neurologic disease or disorder or microvascular disease or disorder or neurodegenerative disease or disorder or a symptom of the acute neurite retraction, accelerated neuron loss, a neurologic disease or disorder or microvascular disease or disorder or neurodegenerative disease or disorder is ameliorated. One or more of the symptoms can be less severe. In some aspects, recovery can be accelerated in an individual who has been treated with one or more of the compositions disclosed herein.

In some aspects, the pharmaceutical composition can be formulated for intravenous administration. In some aspects, the pharmaceutical composition can be formulated for subcutaneous, intranasal, or oral administration. In some aspects, the compositions of the present disclosure also contain a therapeutically effective amount of a 5-HT2A receptor antagonist. In some aspects, the 5-HT2A receptor antagonist can be a peptide. In some aspects, the 5-HT2A receptor antagonist can be ketanserin or volinanserin (also known as MDL—100,907). The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the decoy peptide. Thus, compositions can be prepared for parenteral administration that includes the decoy peptides or polypeptides dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

Methods of Treatment

Disclosed herein are methods of reducing or preventing acute neurite retraction in a subject. In some aspects, the methods can comprise: administering to a subject a therapeutically effective amount of one or more decoy peptides or polypeptides disclosed herein. In some aspects, the methods can further comprise: administering a therapeutically effective amount of one or more decoy peptides or polypeptides disclosed herein and a pharmaceutically acceptable carrier.

Disclosed herein are methods of preventing accelerated neuron loss in a subject. In some aspects, the methods can comprise: administering to a subject a therapeutically effective amount of one or more decoy peptides or polypeptides disclosed herein. In some aspects, the methods can further comprise: administering a therapeutically effective amount of one or more decoy peptides or polypeptides disclosed herein and a pharmaceutically acceptable carrier.

Disclosed herein are methods of reducing the risk of a neurologic disease or disorder or microvascular disease or disorder in a subject. In some aspects, the methods can comprise: administering to a subject a therapeutically effective amount of one or more of the decoy peptides or polypeptides described herein. In some aspects, the methods can further comprise: administering a therapeutically effective amount of one or more decoy peptides or polypeptides disclosed herein and a pharmaceutically acceptable carrier.

Disclosed herein are methods of preventing or reducing cognitive decline (cognitive dysfunction including changes in memory), mood or one or symptoms associated with depression in a subject. In some aspects, the methods can comprise: administering to a subject a therapeutically effective amount of one or more of the decoy peptides or polypeptides described herein. In some aspects, the methods can further comprise: administering a therapeutically effective amount of one or more decoy peptides or polypeptides disclosed herein and a pharmaceutically acceptable carrier. In some aspects, the subject has type 2 diabetes. In some aspects, the subject has type 2 diabetes and a traumatic injury. In some aspects, the subject was diagnosed with type 2 diabetes before the traumatic brain injury. In some aspects, the subject has a traumatic brain injury. In some aspects, the subject does not have or has not been diagnosed with type 2 diabetes. In some aspects, the subject does not have or has not been diagnosed with a traumatic brain injury. In some aspects, the subject has neither type 2 diabetes nor traumatic brain injury or has been diagnosed with type 2 diabetes or a traumatic brain injury. In some aspects, the subject has essential hypertension or obesity.

Disclosed herein are methods of inducing sedation in a subject. In some aspects, the methods can comprise: administering to a subject a therapeutically effective amount of one or more of the decoy peptides or polypeptides described herein. In some aspects, the methods can further comprise: administering a therapeutically effective amount of one or more decoy peptides or polypeptides disclosed herein and a pharmaceutically acceptable carrier. In some aspects, a therapeutically effective amount of SCLLADDN (SEQ ID NO: 2) or a composition comprising or consisting of SCLLADDN (SEQ ID NO: 2) can be administered to the subject. In some aspects, a therapeutically effective amount of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof or a composition comprising or consisting of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof can be administered to the subject.

Disclosed herein are methods of reducing weight gain in a subject. In some aspects, the methods can comprise: administering to a subject a therapeutically effective amount of one or more of the decoy peptides or polypeptides described herein. In some aspects, the methods can further comprise: administering a therapeutically effective amount of one or more decoy peptides or polypeptides disclosed herein and a pharmaceutically acceptable carrier. In some aspects, a therapeutically effective amount of SCLLADDN (SEQ ID NO: 2) or a composition comprising or consisting of SCLLADDN (SEQ ID NO: 2) can be administered to the subject. In some aspects, a therapeutically effective amount of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof or a composition comprising or consisting of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof can be administered to the subject. In some aspects, the subject is diabetic and obese. In some aspects, the subject does not have type 2 diabetes. In some aspects, the subject does not have or has not been diagnosed with type 2 diabetes. In some aspects, the subject is obese. In some aspects, reducing weight gain can be independent of blood glucose concentrations.

Disclosed herein are methods of promoting or inducing weight loss in a subject. In some aspects, the methods can comprise: administering to a subject a therapeutically effective amount of one or more of the decoy peptides or polypeptides described herein. In some aspects, the methods can further comprise: administering a therapeutically effective amount of one or more decoy peptides or polypeptides disclosed herein and a pharmaceutically acceptable carrier. In some aspects, a therapeutically effective amount of SCLLADDN (SEQ ID NO: 2) or a composition comprising or consisting of SCLLADDN (SEQ ID NO: 2) can be administered to the subject. In some aspects, a therapeutically effective amount of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof or a composition comprising or consisting of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof can be administered to the subject. In some aspects, the subject is diabetic and obese. In some aspects, the subject is not diabetic. In some aspects, the subject is obese. In some aspects, weight loss is not related to and is independent from changes in blood glucose concentrations.

Disclosed herein are methods of improving short term memory in a subject. Disclosed herein are methods of improving short term recall in a subject. Disclosed herein are methods of improving spatial memory in a subject. In some aspects, the methods can comprise: administering to a subject a therapeutically effective amount of one or more of the decoy peptides or polypeptides described herein. In some aspects, the methods can further comprise: administering a therapeutically effective amount of one or more decoy peptides or polypeptides disclosed herein and a pharmaceutically acceptable carrier. In some aspects, a therapeutically effective amount of SCLLADDN (SEQ ID NO: 2) or a composition comprising or consisting of SCLLADDN (SEQ ID NO: 2) can be administered to the subject. In some aspects, a therapeutically effective amount of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof or a composition comprising or consisting of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof can be administered to the subject. In some aspects, the subject is diabetic and obese. In some aspects, the subject has type 2 diabetes. In some aspects, the subject is obese. In some aspects, the subject has type 2 diabetes and can be obese. In some aspects, the subject has neither type 2 diabetes nor traumatic brain injury or has been diagnosed with type 2 diabetes or a traumatic brain injury. In some aspects, the subject has neither type 2 diabetes nor is obese or has been diagnosed with type 2 diabetes or obesity.

Disclosed herein are methods of ameliorating a symptom of dementia, Alzheimer's disease or a neurodegenerative disease in a subject. In some aspects, the symptom can be short term memory loss. In some aspects, the methods can comprise: administering to a subject a therapeutically effective amount of one or more of the decoy peptides or polypeptides described herein. In some aspects, the methods can further comprise: administering a therapeutically effective amount of one or more decoy peptides or polypeptides disclosed herein and a pharmaceutically acceptable carrier. In some aspects, a therapeutically effective amount of SCLLADDN (SEQ ID NO: 2) or a composition comprising or consisting of SCLLADDN (SEQ ID NO: 2) can be administered to the subject. In some aspects, a therapeutically effective amount of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof or a composition comprising or consisting of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof can be administered to the subject. In some aspects, the subject is diabetic and obese. In some aspects, the subject has type 2 diabetes. In some aspects, the subject is obese. In some aspects, the subject has type 2 diabetes and can be obese. In some aspects, the subject has neither type 2 diabetes nor traumatic brain injury or has been diagnosed with type 2 diabetes or a traumatic brain injury. In some aspects, the subject has neither type 2 diabetes nor is obese or has been diagnosed with type 2 diabetes or obesity.

Disclosed herein are methods of preventing or reducing one or more symptoms of retinal degeneration or the risk of developing retinal degeneration in a subject. In some aspects, the methods can comprise: administering to a subject a therapeutically effective amount of one or more of the decoy peptides or polypeptides described herein. In some aspects, the methods can further comprise: administering a therapeutically effective amount of one or more decoy peptides or polypeptides disclosed herein and a pharmaceutically acceptable carrier. In some aspects, a therapeutically effective amount of SCLLADDN (SEQ ID NO: 2) or a composition comprising or consisting of SCLLADDN (SEQ ID NO: 2) can be administered to the subject. In some aspects, a therapeutically effective amount of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof or a composition comprising or consisting of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof can be administered to the subject.

Disclosed herein are methods of lowering blood pressure or lowering hypertension in a subject. In some aspects, the methods can comprise: administering to a subject a therapeutically effective amount of one or more of the decoy peptides or polypeptides described herein. In some aspects, the methods can further comprise: administering a therapeutically effective amount of one or more decoy peptides or polypeptides disclosed herein and a pharmaceutically acceptable carrier. In some aspects, a therapeutically effective amount of SCLLADDN (SEQ ID NO: 2) or a composition comprising or consisting of SCLLADDN (SEQ ID NO: 2) can be administered to the subject. In some aspects, a therapeutically effective amount of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof or a composition comprising or consisting of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof can be administered to the subject. In some aspects, the subject is diabetic and obese. In some aspects, the subject has type 2 diabetes. In some aspects, the subject is obese. In some aspects, the subject is not obese. In some aspects, the subject does not have or has not been diagnosed with type 2 diabetes. In some aspects, the subject can be have mild or high blood pressure. In some aspects, the subject can be have mild or high blood pressure and has not been diagnosed with any known disease, disorder or condition.

Blood pressure is the force exerted by the bloodstream on the artery walls. Normal blood pressure is considered to be 120 systolic and 80 diastolic. Hypertension refers to a disorder that can be characterized by an elevation of the systolic blood pressure to 140 and above and/or an elevation of the diastolic blood pressure to 90 and above. With hypertension, there is either an increase in the total peripheral vascular resistance such as is due to vasoconstriction, or an increase in cardiac output, or both. These conditions produce an elevation in blood pressure because blood pressure is equal to flow times resistance. Many factors can contribute to high blood pressure including but not limited to stress, diet and lifestyle, as well as kidney complaints, hormonal disturbances and circulatory disorders. An untreated hypertensive patient is at great risk of developing left ventricular failure, myocardial infarction, cerebral hemorrhage or renal failure. Hypertension can also be a risk factor for stroke and coronary atherosclerosis. Currently, hypertensive patients are treated with drug therapy that includes the use of diuretics, beta-blockers, ACE inhibitors, angiotensin antagonists, calcium channel blockers, alpha-blockers, alpha-beta-blockers, nervous system inhibitors, and vasodilators. Essential hypertension is high blood pressure that doesn't have a known secondary cause. Refractory hypertension is defined as uncontrolled blood pressure despite use of five or more antihypertensive agents of different classes.

Disclosed herein are methods of preventing or reducing one or more symptoms of kidney disease or the risk of developing kidney disease in a subject. In some aspects, the kidney disease can be diabetic kidney disease. In some aspects, the methods can comprise: administering to a subject a therapeutically effective amount of one or more of the decoy peptides or polypeptides described herein. In some aspects, the methods can further comprise: administering a therapeutically effective amount of one or more decoy peptides or polypeptides disclosed herein and a pharmaceutically acceptable carrier. In some aspects, a therapeutically effective amount of SCLLADDN (SEQ ID NO: 2) or a composition comprising or consisting of SCLLADDN (SEQ ID NO: 2) can be administered to the subject. In some aspects, a therapeutically effective amount of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof or a composition comprising or consisting of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof can be administered to the subject.

Also disclosed herein are methods of identifying a subject at risk for developing a neurodegenerative disease. In some aspects, the subject has type 2 diabetes, hypertension, or obesity. In some aspects, the subject does not have type 2 diabetes or has not been diagnosed with type 2 diabetes. In some aspects, the subject does not have hypertension or has not been diagnosed with hypertension. In some aspects, the subject is not obese. In some aspects, the subject has a traumatic brain injury. In some aspects, the subject has a traumatic brain injury and type 2 diabetes. In some aspects, the subject has a traumatic brain injury, type 2 diabetes and obesity. In some aspects, subject does not have or has been diagnosed with any of traumatic brain injury, type 2 diabetes or obesity. In some aspects, the method comprise: a) obtaining or having obtained a sample from the subject, wherein the sample can comprise one or more 5-HT2A receptor autoantibodies; b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more of the decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); and d) identifying the subject at risk for developing a neurodegenerative disease when the level of binding in step c) is higher when compared to the level of binding in a reference sample. In some aspects, the method can further comprise administering to the subject a therapeutically effective amount of a 5-HT2A receptor antagonist. In some aspects, the method can further comprise administering to the subject a therapeutically effective amount of one or more of the decoy peptides or polypeptides disclosed herein. In some aspects, the sample can be plasma or serum. In some aspects, the level of binding of 5-HT2A receptor autoantibodies to one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4) can be determined by ELISA. In some aspects, the 5-HT2A receptor antagonist can inhibit the binding of 5-HT2A receptor autoantibodies to a second extracellular loop region of the 5-HT2A receptor. In some aspects, the 5-HT2A receptor antagonist can inhibit the binding of 5-HT2A receptor autoantibodies to a second extracellular loop region of the 5-HT2A receptor by competitive inhibition. In some aspects, the 5-HT2A receptor antagonist can be a decoy peptide or polypeptide. In some aspects, the decoy peptide can inhibit the binding of 5-HT2A receptor autoantibodies to a second extracellular loop region of the 5-HT2A receptor. In some aspects, the decoy peptide can inhibit the binding of 5-HT2A receptor autoantibodies to a second extracellular loop region of the 5-HT2A receptor by competitive inhibition. In some aspects, the subject can be identified in need of treatment before the administration step. In some aspects, the subject can be human. In some aspects, the method can further comprise administering to the subject ketanserin or volinanserin (also known as MDL—100,907).

Disclosed herein are methods of treating a subject at risk for developing a neurodegenerative disease or preventing or ameliorating a symptom of neurodegenerative disease in a subject. In some aspects, the subject has type 2 diabetes, refractory hypertension, essential hypertension, or obesity. In some aspects, the subject does not have or has not been diagnosed with type 2 diabetes, refractory hypertension, essential hypertension or obesity. In some aspects, the subject has a traumatic brain injury. In some aspects, the subject has a traumatic brain injury and type 2 diabetes. In some aspects, the methods can comprise: a) obtaining or having obtained a sample from the subject, wherein the sample can comprise one or more 5-HT2A receptor autoantibodies; b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more of the decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); d) identifying the subject at risk for developing a neurodegenerative disease when the level of binding in step c) is higher when compared to the level of binding in a reference sample; and e) administering to the subject a therapeutically effective amount of a 5-HT2A receptor antagonist. In some aspects, step e) can comprise administering to the subject a therapeutically effective amount of a decoy peptide or polypeptide disclosed herein. In some aspects, the sample can be plasma or serum. In some aspects, the level of binding of 5-HT2A receptor autoantibodies to one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4) can be determined by ELISA. In some aspects, the -HT2A receptor antagonist can inhibit the binding of 5-HT2A receptor autoantibodies to a second extracellular loop region of the 5-HT2A receptor. In some aspects, the 5-HT2A receptor antagonist can inhibit the binding of 5-HT2A receptor autoantibodies to a second extracellular loop region of the 5-HT2A receptor by competitive inhibition. In some aspects, the 5-HT2A receptor antagonist can be a decoy peptide or polypeptide. In some aspects, the decoy peptide can inhibit the binding of 5-HT2A receptor autoantibodies to a second extracellular loop region of the 5-HT2A receptor. In some aspects, the decoy peptide can inhibit the binding of 5-HT2A receptor autoantibodies to a second extracellular loop region of the 5-HT2A receptor by competitive inhibition. In some aspects, the subject can be identified in need of treatment before the administration step. In some aspects, the subject can be human. In some aspects, the method can further comprise administering to the subject ketanserin or volinanserin (also known as MDL—100,907).

Also disclosed herein are methods of identifying a subject at risk for or developing retinal degeneration. In some aspects, the subject has type 2 diabetes, essential hypertension, or obesity. In some aspects, the subject does not have or has not been diagnosed with type 2 diabetes, essential hypertension or obesity. In some aspects, the methods can comprise: a) obtaining or having obtained a sample from the subject, wherein the sample can comprise one or more 5-HT2A receptor autoantibodies; b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); and d) identifying the subject at risk for developing a retinal degeneration when the level of binding in step c) is higher when compared to the level of binding in a reference sample. In some aspects, the method can further comprise administering to the subject a therapeutically effective amount of a 5-HT2A receptor antagonist. In some aspects, the method can further comprise administering to the subject a therapeutically effective amount of one or more of the decoy peptides or polypeptides disclosed herein. In some aspects, the sample can be plasma or serum. In some aspects, the level of binding of 5-HT2A receptor autoantibodies to the one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4) can be determined by ELISA. In some aspects, the 5-HT2A receptor antagonist can inhibit the binding of 5-HT2A receptor autoantibodies to a second extracellular loop region of the 5-HT2A receptor. In some aspects, the 5-HT2A receptor antagonist can inhibit the binding of 5-HT2A receptor autoantibodies to a second extracellular loop region of the 5-HT2A receptor by competitive inhibition. In some aspects, the 5-HT2A receptor antagonist can be a decoy peptide or polypeptide. In some aspects, the decoy peptide can inhibit the binding of 5-HT2A receptor autoantibodies to a second extracellular loop region of the 5-HT2A receptor. In some aspects, the decoy peptide can inhibit the binding of 5-HT2A receptor autoantibodies to a second extracellular loop region of the 5-HT2A receptor by competitive inhibition. In some aspects, the subject can be identified in need of treatment before the administration step. In some aspects, the subject can be human. In some aspects, the method can further comprise administering to the subject ketanserin or volinanserin (also known as MDL—100,907).

Disclosed herein are methods of treating a subject having or at risk for developing retinal degeneration. In some aspects, the subject has type 2 diabetes. In some aspects, the subject has type 2 diabetes, essential hypertension, or obesity. In some aspects, the subject does not have or has not been diagnosed with type 2 diabetes, essential hypertension or obesity. In some aspects, the methods can comprise: a) obtaining or having obtained a sample from the subject, wherein the sample can comprise one or more 5-HT2A receptor autoantibodies; b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more of the decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); d) identifying the subject at risk for developing a retinal degeneration when the level of binding in step c) is higher when compared to the level of binding in a reference sample; and e) administering to the subject a therapeutically effective amount of a 5-HT2A receptor antagonist. In some aspects, step e) can comprise administering to the subject a therapeutically effective amount of a decoy peptide or polypeptide disclosed herein. In some aspects, the sample can be plasma or serum. In some aspects, the level of binding of 5-HT2A receptor autoantibodies to the one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4) can be determined by ELISA. In some aspects, the -HT2A receptor antagonist can inhibit the binding of 5-HT2A receptor autoantibodies to a second extracellular loop region of the 5-HT2A receptor. In some aspects, the 5-HT2A receptor antagonist can inhibit the binding of 5-HT2A receptor autoantibodies to a second extracellular loop region of the 5-HT2A receptor by competitive inhibition. In some aspects, the 5-HT2A receptor antagonist can be a decoy peptide or polypeptide. In some aspects, the decoy peptide can inhibit the binding of 5-HT2A receptor autoantibodies to a second extracellular loop region of the 5-HT2A receptor. In some aspects, the decoy peptide can inhibit the binding of 5-HT2A receptor autoantibodies to a second extracellular loop region of the 5-HT2A receptor by competitive inhibition. In some aspects, the subject can be identified in need of treatment before the administration step. In some aspects, the subject can be human. In some aspects, the method can further comprise administering to the subject ketanserin or volinanserin (also known as MDL—100,907).

Disclosed herein are methods of treating a subject having or at risk for kidney disease, kidney dysfunction or kidney failure. In some aspects, the subject has type 2 diabetes or refractory hypertension. In some aspects, the methods can comprise: a) obtaining or having obtained a sample from the subject, wherein the sample can comprise one or more 5-HT2A receptor autoantibodies; b) contacting the sample of step a) with one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); c) determining the level of binding of the 5-HT2A receptor autoantibodies to the one or more of the decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4); d) identifying the subject at risk for kidney disease, kidney dysfunction or kidney failure when the level of binding in step c) is higher when compared to the level of binding in a reference sample; and e) administering to the subject a therapeutically effective amount of a 5-HT2A receptor antagonist. In some aspects, step e) can comprise administering to the subject a therapeutically effective amount of a decoy peptide or polypeptide disclosed herein. In some aspects, the sample can be plasma or serum. In some aspects, the level of binding of 5-HT2A receptor autoantibodies to the one or more decoy peptides comprising the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4) can be determined by ELISA. In some aspects, the -HT2A receptor antagonist can inhibit the binding of 5-HT2A receptor autoantibodies to a second extracellular loop region of the 5-HT2A receptor. In some aspects, the 5-HT2A receptor antagonist can inhibit the binding of 5-HT2A receptor autoantibodies to a second extracellular loop region of the 5-HT2A receptor by competitive inhibition. In some aspects, the 5-HT2A receptor antagonist can be a decoy peptide or polypeptide. In some aspects, the decoy peptide can inhibit the binding of 5-HT2A receptor autoantibodies to a second extracellular loop region of the 5-HT2A receptor. In some aspects, the decoy peptide can inhibit the binding of 5-HT2A receptor autoantibodies to a second extracellular loop region of the 5-HT2A receptor by competitive inhibition. In some aspects, the subject can be identified in need of treatment before the administration step. In some aspects, the subject can be human. In some aspects, the method can further comprise administering to the subject ketanserin or volinanserin (also known as MDL—100,907).

In some aspects of the methods disclosed herein, the decoy peptides or polypeptides described herein can be part of a scaffold protein. In any of the methods disclosed herein, the scaffold protein can comprise a SH3 (src homolog3), SH2 (src homolog2), PDZ, or GTPase-binding domain (GBD) and a heterologous peptide. In some aspects, the heterologous peptide can be inserted or connected to one or more of a SH3 (src homolog3), SH2 (src homolog2), PDZ, or GTPase-binding domain (GBD). In some aspects, the heterologous peptide can be one or more of the decoy peptides or polypeptides disclosed herein. In some aspects, the heterologous peptide can comprise or consist of one or more decoy peptides comprising the sequence of QDDSKVFKEGSCLLADDN (SEQ ID NO: 1), or a fragment thereof, SCLLADDN (SEQ ID NO: 2), QDDSKVF (SEQ ID NO: 3), or VFKEGSC (SEQ ID NO: 4). In some aspects, the heterologous peptide can comprise or consist of one or more decoy peptides comprising a variant of the sequence of QDDSKVFKEGSCLLADDN (SEQ ID NO: 1), SCLLADDN (SEQ ID NO: 2), QDDSKVF (SEQ ID NO: 3), or VFKEGSC (SEQ ID NO: 4). In some aspects, the method can comprise administering a composition that can be formulated for intravenous, subcutaneous, intranasal or oral administration.

In some aspects, the 5-HT2A receptor antagonist can be any of the decoy peptides or polypeptides disclosed herein. In some aspects, the 5-HT2A receptor antagonist can be SCLLADDN (SEQ ID NO: 2). In some aspects, the 5-HT2A receptor antagonist can be QDDSKVFKEGSCLLADDN (SEQ ID NO: 1) or a fragment thereof. In some aspects, the 5-HT2A receptor antagonist can be QDDSKVF (SEQ ID NO: 3). In some aspects, the 5-HT2A receptor antagonist can be VFKEGSC (SEQ ID NO: 4).

In some aspects, the level of binding of the 5-HT2A receptor autoantibodies in the sample can be increased or higher when compared to the level of binding of 5-HT2A receptor autoantibodies in a control or reference sample. In some aspects, a sample from a subject can be identified as being in need of treatment when the level of binding of the 5-HT2A receptor autoantibodies in the sample can be increased or higher when compared to the level of binding of 5-HT2A receptor autoantibodies in a control or reference sample. In some aspects, the sample from the subject can be identified as being at risk for developing a neurodegenerative disease, retinal degeneration, or kidney disease, kidney dysfunction or kidney failure. In some aspects, the control or reference sample can be from an age-matched sample. In some aspects, the sample can be from one or more subjects that do have or are known to not be at risk for developing a neurodegenerative disease or retinal degeneration.

As used herein, the terms, "reference," "reference expression," "reference sample," "reference value," "control," "control sample" and the like, when used in the context of a sample or expression level of the binding of 5HT2A receptor autoantibodies to one or more of the decoy peptides disclosed herein refers to a reference standard wherein the reference is expressed at a constant level, and is unaffected by the experimental conditions, and is indicative of the level in a sample of a predetermined disease status (e.g., not suffering from a neurodegenerative disease, type 2 diabetes, retinal degeneration) or whether a subject (or disease) will respond to a therapeutic agent or treatment. The reference value can be a predetermined standard value or a range of predetermined standard values, representing no illness, or a predetermined type or severity of illness or representing the likelihood a disease, disorder or condition will be responsive to a particular type of therapeutic agent or treatment.

Reference expression can be the level of the binding of 5HT2A receptor autoantibodies to one or more of the decoy peptides disclosed herein in a reference sample from a subject, or a pool of subjects, not suffering from disease, disorder or condition (e.g., a neurodegenerative disease, refractory hypertension, retinal degeneration), with a known response (or lack thereof) to a particular treatment or known to be at risk for having or developing a disease, disorder or condition (e.g., a neurodegenerative disease, refractory hypertension, retinal degeneration). In some aspects, the reference value can be taken a different time point than to which it is being compared.

As used herein, a "reference value" can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the individual before administration of or exposure to a particular therapeutic agent, but at an earlier point in time, or a value obtained from a sample from a subject other than the individual being tested, or a "normal" individual, that is an individual not diagnosed with any of the diseases, disorders or conditions described herein. The reference value can be based on a large number of samples, such as from subjects with any of the diseases, disorders or conditions described herein or normal individuals or based on a pool of samples including or excluding the sample to be tested. The reference value can also be based on a sample from subjects with any of the diseases, disorders or conditions described herein other than the individual being tested, or a "normal" individual that is an individual not diagnosed with any of the diseases, disorders or conditions described herein that has not or has been administered or exposed to a particular therapeutic agent.

The reference level used for comparison with the measured level for the binding of 5HT2A receptor autoantibodies to any of the decoy peptides disclosed herein can vary, depending the method begin practiced, as will be understood by one of ordinary skill in the art. For methods for determining the likelihood a disease, disorder or condition (e.g., a neurodegenerative disease, type 2 diabetes, retinal degeneration), a subject or a sample will be responsive to a particular type of therapeutic agent or treatment, the "reference level" is typically a predetermined reference level, such as an average of levels obtained from a population that has either been exposed or has not been exposed to particular type of therapeutic agent or treatment, but in some instances, the reference level can be a mean or median level from a group of individuals that are responders or non-responders. In some instances, the predetermined reference level can be derived from (e.g., is the mean or median of) levels obtained from an age-matched population.

Age-matched populations (from which reference values may be obtained) can be populations that are the same age as the individual being tested, but approximately age-matched populations are also acceptable. Approximately age-matched populations may be within 1, 2, 3, 4, or 5 years of the age of the individual tested, or may be groups of different ages which encompass the age of the individual being tested. Approximately age-matched populations may be in 2, 3, 4, 5, 6, 7, 8, 9, or 10 year increments (e.g. a "5 year increment" group which serves as the source for reference values for a 62 year old individual might include 58-62 year old individuals, 59-63 year old individuals, 60-64 year old individuals, 61-65 year old individuals, or 62-66 year old individuals).

Determining the level of binding of the 5-HT2A receptor autoantibodies to one or more of the decoy peptides disclosed herein can include determining whether the binding of the 5-HT2A receptor autoantibodies to one or more of the decoy peptides disclosed herein is increased as compared to a control or reference sample or a sample that has been contacted, administered or exposed to a particular therapeutic agent or treatment, decreased compared to a control or reference sample or a sample that has been contacted, administered or exposed to a particular therapeutic agent or treatment, or unchanged compared to a control or reference sample or a sample that has been contacted, administered or exposed to a particular therapeutic agent or treatment. As used herein, the terms, "increased" or "increased expression level" or "increased level of expression" or "increased amount of protein" or "high" or "higher level" or "higher expression level" refers to an amount of binding of the 5-HT2A receptor autoantibodies to one or more of the decoy peptides disclosed herein that is expressed wherein the measure of the quantity of the binding of the 5-HT2A receptor autoantibodies to one or more of the decoy peptides disclosed herein exhibits an increased level of expression when compared to a reference sample or "normal" control or a sample that has been contacted, administered or exposed to a particular therapeutic agent or treatment. An "increased expression level" or "higher expression level" refers to an increase in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more. As used herein, the terms "decreased," "decreased level of expression," or "decreased expression level" or "decreased amount of protein" or "low" or "lower level" or "lower expression level" refers to an amount of binding of the 5-HT2A receptor autoantibodies to one or more of the decoy peptides disclosed herein that is expressed wherein the measure of the quantity of the binding of the 5-HT2A receptor autoantibodies to one or more of the decoy peptides disclosed herein exhibits a decreased level of expression when compared to a reference sample or "normal" control or a sample that has been contacted, administered or exposed to a particular therapeutic agent or treatment. A "decreased level of expression" or "lower expression level" refers to a decrease in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more.

The level of binding of the 5-HT2A receptor autoantibodies to one or more of the decoy peptides disclosed herein disclosed herein can be a measure, for example, per unit weight or volume. In some aspects, the expression level can be a ratio (e.g., the amount of binding of the 5-HT2A receptor autoantibodies to one or more of the decoy peptides disclosed herein in a sample relative to the amount of the binding of the 5-HT2A receptor autoantibodies to one or more of the decoy peptides disclosed herein of a reference value or in a reference sample that may have been or may have not been also contacted with a therapeutic agent).

The method of comparing a measured value and a reference value or a measured value before and after contact with a therapeutic agent can be carried out in any convenient manner appropriate to the type of measured value (e.g., the binding of the 5-HT2A receptor autoantibodies to one or more of the decoy peptides disclosed herein). For example, 'measuring' can be performed using quantitative or qualitative measurement techniques, and the mode of comparing a measured value and a reference value can vary depending on the measurement technology employed. For example, the measured values used in the methods described herein can be quantitative values (e.g., quantitative measurements of concentration, such as nanograms of the 5HT2A receptor autoantibodies per milliliter of sample, or absolute amount). As with qualitative measurements, the comparison can be made by inspecting the numerical data, by inspecting representations of the data (e.g., inspecting graphical representations such as bar or line graphs).

In some aspects, the level of binding of 5-HT2A receptor autoantibodies can be determined by various analysis methods. For example, the binding of 5-HT2A receptor autoantibodies can be determined in various immunoassay formats. These immunological analysis methods may be carried out according to various quantitative immunoassay protocols that have been developed in the prior art. Examples of the immunoassay format include radioactive immunoassay, radioactive immunoprecipitation, immunoprecipitation, enzyme-linked immunosorbent assay (ELISA), captured-ELISA, inhibition or competition analysis, sandwich assay, immunofluorescent staining, and immunoaffinity purification, but are not limited thereto.

Disclosed herein are methods of competitively inhibiting the binding of 5-HT2A receptor autoantibodies to a second extracellular loop region of the 5-HT2A receptor. In some aspects, the method can comprise: administering to a subject a therapeutically effective amount of a peptide comprising or consisting of the amino acid sequence of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1) or a fragment thereof. In some aspects, the method can comprise: administering to a subject a therapeutically effective amount of a peptide comprising or consisting of a variant of the amino acid sequence of SCLLADDN (SEQ ID NO: 2), QDDSKVF (SEQ ID NO: 3), VFKEGSC (SEQ ID NO: 4) or QDDSKVFKEGSCLLADDN (SEQ ID NO: 1). In some aspects, the subject can be identified in need of treatment before the administration step. In some aspects, the subject can be human. In some aspects, the method can further comprise administering to the subject ketanserin or volinanserin (also known as MDL—100,907). In some aspects, the subject can be at risk for developing retinal degeneration, kidney disease, a neurologic disease or disorder, kidney dysfunction, kidney failure, a microvascular disease or disorder, or a neurodegenerative disease or disorder. In some aspects, the neurologic disease or disorder can be a neuropathy, open angle glaucoma, dementia, major depressive disorder, Parkinson's disease, dementia or a combination thereof. In some aspects, the microvascular disease or disorder can be a stroke or kidney failure. In some aspects, the subject has type 2 diabetes. In some aspects, the subject has a traumatic brain injury. In some aspects, the subject has type 2 diabetes, hypertension or obesity or has been diagnosed with type 2 diabetes or hypertension. In some aspects, the subject does not have or has not been diagnosed with type 2 diabetes, hypertension or obesity. In some aspects, the subject has type 2 diabetes and a traumatic brain injury. In some aspects, the subject has obesity. In some aspects, the subject has refractory hypertension or essential hypertension.

Disclosed herein are methods of competitively inhibiting the binding of 5-HT2A receptor autoantibodies to a second extracellular loop region of the 5-HT2A receptor. In some aspects, the method can comprise: administering to a subject a therapeutically effective amount of any of decoy peptide or polypeptides disclosed herein. In some aspects, the methods can comprise: administering to a subject a therapeutically effective amount of any of the compositions disclosed herein. In some aspects, the subject can be identified in need of treatment before the administration step. In some aspects, the subject can be human. In some aspects, the method can further comprise administering to the subject ketanserin or volinanserin (also known as MDL—100,907). In some aspects, the subject can be at risk for developing retinal degeneration, kidney disease, kidney dysfunction, kidney failure, a neurologic disease or disorder, or a microvascular disease or disorder, or a neurodegenerative disease or disorder. In some aspects, the subject can be at risk for developing kidney dysfunction or kidney failure. In some aspects, the neurologic disease or disorder can be a neuropathy, open angle glaucoma, dementia, major depressive disorder, Parkinson's disease or a combination thereof. In some aspects, the microvascular disease or disorder can be a stroke or kidney dysfunction or kidney failure. In some aspects, the subject has type 2 diabetes. In some aspects, the subject has or has been diagnosed with type 2 diabetes, essential hypertension, or obesity. In some aspects, the subject does not have or has not been diagnosed with type 2 diabetes, essential hypertension or obesity. In some aspects, the subject has a traumatic brain injury. In some aspects, the subject has type 2 diabetes and a traumatic brain injury. In some aspects, the subject has obesity. In some aspects, the subject has refractory hypertension or essential hypertension.

In some aspects, the subject can be identified as being in need of treatment before the administration step. In some aspects, the subject can have type 2 diabetes, a traumatic brain microvascular angiopathy (including diabetic or hypertensive nephropathy), Parkinson's disease, dementia, major depressive disorder, schizophrenia, retinitis pigmentosa, refractory hypertension, essential hypertension, hypertension, mild cognitive dysfunction, primary open angle glaucoma, obesity or has had a stroke or a combination thereof. In some aspects, the subject is not obese. In some aspects, the subject does not have type 2 diabetes. In some aspects, the subject does not have a traumatic brain injury.

In some aspects, the neurologic disease or disorder can be a neuropathy, open angle glaucoma, dementia, major depressive disorder, Parkinson's disease or a combination thereof.

In some aspects, the microvascular disease or disorder can be a stroke. In some aspects, the microvascular disease or disorder can be age-related macular degeneration, diabetic macular edema, diabetic nephropathy, hypertensive nephropathy.

In some aspects, the refractory hypertension can be associated with stroke or chronic kidney disease. In some aspects, the neurodegenerative disease can be dementia, Parkinson's disease, macular degeneration, or retinal degeneration.

In some aspects, in any of the methods disclosed herein, the methods can further comprise: administering a therapeutically effective amount of one or more decoy peptides or polypeptides disclosed herein. In some aspects, the one or more decoy peptides or polypeptides disclosed herein can be administered along with a pharmaceutically acceptable carrier.

In some aspects, any of the decoy peptides or polypeptides disclosed herein can be delivered or administered to a subject by direct injection into the eye, for example, to treat retinal degenerative disorder; by direct or local injection into the brain or cerebrospinal fluid, for example, to treat brain a neurodegenerative disorder; and by direct injection into an occluded arterial region via intra-arterial catheter, for example, in an acute stroke setting, Amounts effective for these uses can depend on the severity of the condition, disease or disorder or the severity of the risk of the condition, disease or disorder, and the weight and general state and health of the subject, but generally range from about 0.05 µg to about 1000 µg (e.g., 0.5-100 µg) or 0.5 mg/kg to about 3 mg/kg per body weight per subject of an equivalent amount of the decoy peptide per dose per subject. Suitable regimes for initial administration and booster administrations are typified by an initial administration followed by repeated doses at one or more hourly, daily, weekly, or monthly intervals by a subsequent administration. For example, a subject can receive any of decoy peptides or polypeptides described herein in the range of about 0.05 to 1,000 µg or 0.5 to 3.0 mg/kg body weight equivalent dose per dose one or more times per week (e.g., 2, 3, 4, 5, 6, or 7 or more times per week). For example, a subject can receive 0.1 to 2,500 µg (e.g., 2,000, 1,500, 1,000, 500, 100, 10, 1, 0.5, or 0.1 µg) dose per week. In some aspects, a subject can receive 0.5 to 3.0 mg/kg daily (e.g., 3.5 to 21 mg/kg body weight). In some aspects, a subject can receive 0.5 to 3.0 mg/kg (e.g., 3.5 to 21 mg/kg body weight) daily dose per week. In some aspects, a subject can receive 0.5 to 3.0 mg/kg (e.g., 3.5 to 21 mg/kg body weight) per dose for one or more does per day per week. A subject can also receive any of the decoy peptides or polypeptides described herein in the range of 0.1 to 3,000 µg per dose once every two or three weeks. In some aspects, a subject can also receive any of the decoy peptides or polypeptides described herein in the range of 0.5 to 3.0 mg/kg body weight per dose once every two or three weeks. A subject can also receive 2 mg/kg every week (with the weight calculated based on the weight of the decoy peptide or polypeptide described herein and the weight in kg calculated based on the weight of the subject).

The total effective amount of decoy peptide or polypeptide in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of one or more of the decoy peptides or polypeptides present within the compositions described herein and used in the methods as disclosed herein applied to mammals (e.g., humans) can be determined by one of ordinary skill in the art with consideration of individual differences in age, weight, and other general conditions (as mentioned above).

EXAMPLES

Example 1: Compositions of Matter that are Neuroprotective Against Plasma IgG Autoantibodies Mediating Serotonin 2A Receptor Toxicity in Diverse Neurodegenerative Disorders Abstract. Aims: To test whether IgG autoantibodies in subsets of diabetes having neurovascular complications bind to a synthetic peptide comprised of the second extracellular loop region of the human 5-hydroxytryptamine 2A receptor.

Methods: Plasma or serum from fifty-six older adults with (n=49) or without (n=7) type 2 diabetes was subjected to Protein-A affinity chromatography to obtain IgG autoantibodies. Binding to a synthetic 18-meric linear synthetic peptide (SEQ ID NO: 1) corresponding to the second extracellular loop of the 5-hydroxytryptamine 2A receptor was tested in a $1/40^{th}$ or higher dilution of the protein-A eluates. Mean acute neurite retraction (5 minutes) or cell survival (16-24 hours) was determined in mouse N2A neuroblastoma cells incubated with IgG autoantibodies in the presence or absence of three short, linear overlapping peptides comprising the second extracellular loop of the human 5-hydroxytryptamine 2A receptor (SEQ ID NOs: 2, 3 and 4).

Results: Increased binding to the linear synthetic peptide comprising the 5-hydroxytryptamine 2A receptor's second extracellular loop was significantly increased in subsets of older adults with diabetes and microvascular complications and in diabetes with Parkinson's disease, dementia, cerebrovascular accident, major depressive disorder, schizophrenia compared to binding in autoantibodies from age-matched diabetes without microvascular complications. Highest binding was observed in patients with a co-morbid systemic autoimmune disease. A short linear synthetic peptide corresponding to a subregion of the second extracellular loop of the 5-hydroxytryptamine 2A receptor significantly prevented acute neurite retraction and accelerated N2A cell loss mediated by diabetic neurovascular pathologies autoantibodies.

Conclusion: Diabetes with microvascular complications and/or neurovascular and neuropsychiatric complications harbor circulating autoantibodies (e.g., 5-HT2A receptors autoantibodies) which bind to the second extracellular loop region of the 5-hydroxytryptamine 2A receptor causing long-lasting receptor activation leading to neurite retraction and accelerated N2A neuroblastoma cell loss.

Participants and Methods. Participants. Men and women enrolled in the Diabetes or Endocrinology clinics at the Veterans Affairs New Jersey Healthcare System, East Orange and Lyons N.J. participated.

Patient subgroups. Patient 1: A 57-year-old man with morbid obesity, type 2 diabetes, stage 3 chronic kidney disease (CKD) and refractory hypertension who suffered a branch retinal vein occlusion and transient ischemic attack (TIA). He underwent renal biopsy which revealed hypertensive glomerulosclerosis (FIG. 14). Patient 2: A 72-year-old man with twenty-year history of type 2 diabetes, discoid lupus erythematosus, and adult onset retinitis pigmentosa who had also suffered with a central retinal artery occlusion. Patient 3: An 81 year-old-man who suffered with autoimmune thyroid disease and juvenile-onset retinitis pigmentosa (Stargardt disease). He has a ten-year history of type 2 diabetes without microvascular complications. Family history is positive for Stargardt disease in one brother.

Blood drawing. Blood was drawn in the morning in fasted participants. Protein-A Affinity Chromatography. Protein A affinity chromatography was carried out (Zimering M B. *J Endocrinol Diabetes.* 2018; 5(2)).

Synthetic peptide synthesis. A synthetic peptide having the amino acid sequence QDDSKVFKEGSCLLADDN (SEQ ID NO: 1), also referred herein as Q . . . N-18 or peptide 1, was synthesized at Lifetein Inc. and had ≥92% purity (Hillsborough, N.J.). Q . . . N-18 has an amino acid sequence that corresponds to the region of the human 5-HT2A receptor comprising the second extracellular loop (ECL2). Three shorter overlapping peptides (peptide 2; SEQ ID NO: 2), (peptide 3; SEQ ID NO: 3), and (peptide 4; SEQ ID NO: 4) were synthesized at Lifetein, Inc and had purities>92%. The latter three peptides were used in epitope analysis of the region of Q . . . N-18 (SEQ ID NO: 1) targeted for binding by subsets of human pathologies' autoantibodies.

Enzyme linked immunosorbent assay (ELISA). Ninety-six well plates were coated with the Q . . . N-18 peptide in PBS at a concentration of 65 µg/mL for two hours at 25 degrees C. The plates were washed three times with 0.1% Triton X-100 in PBS (PBS/Triton). Next the plate was blocked with 3% BSA in PBS for 1 h. Following 3 washes with PBS/Triton, 0.5-10 µg/mL concentrations of the patient IgG antibody (obtained by protein A affinity chromatography of plasma or serum) or a control sample was added to wells in duplicate and incubated for 1 h. The plate was washed 3× in PBS/Triton. Next HRP-conjugated goat anti-human IgG (Sigma, St. Louis, Mo.) was added to each well at a 1:3000 final dilution. After 1 h incubation, the plate was washed 3× in PBS/Triton. Next 150 µL of a substrate solution containing 0.4 mg/mL ortho-phenylenediamine (Sigma, St. Louis, Mo.) and $H_2O_2$ was added to each well and the reaction was monitored for color development. After 5 min, the reaction was stopped by the addition of 50 µL 8 M $H_2SO_4$ and the optical density was read at 490 nm in a microtiter plate reader. Results are expressed as basal $OD_{490}$ compared to wells to which PBS alone was added.

Mouse neuroblastoma N2 cells. N2A cells were cultured in DMEM with 10% fetal calf serum.

N2A Acute Neurite Retraction assay. Acute neurite retraction assay was performed as described in Hu G, et al. *Diabetes Care* 2007; 30(4): 842-847.

N2 cell survival assay. Cell survival assays were carried out as described in Hu G, et al. *Diabetes Care* 2007; 30(4): 842-847.

Chemicals. Chemicals (with the exception of Q . . . N18) were from Sigma Chem Co, Inc.

Protein determinations. Protein assays were carried out as described in Hu G, et al. *Diabetes Care* 2007; 30(4): 842-847.

Results. Baseline clinical characteristics in the study patients. The baseline clinical characteristics are shown in Table 1. The study cohort included 49 older adults with type 2 diabetes and 7 older adults without diabetes. The patients without diabetes were slightly younger on average, but did not differ significantly from the diabetic patients in their mean body mass index 31.0 vs 34.9 kg/m$^2$ (Table 2). Mean binding to a linear synthetic 5HT2A receptor peptide did not differ significantly in autoantibodies from in Parkinson's disease or major depressive disorder patients with or without baseline type 2 diabetes (Table 3). These data suggests that diabetes per se may not be a risk factor for autoantibody occurrence in subsets of obese older adults with certain neurodegenerative diseases. It also suggests that the populations at risk for neurodegeneration indicated by the presence of elevated level of receptor autoantibodies may include both diabetic and nondiabetics.

Figure 14:
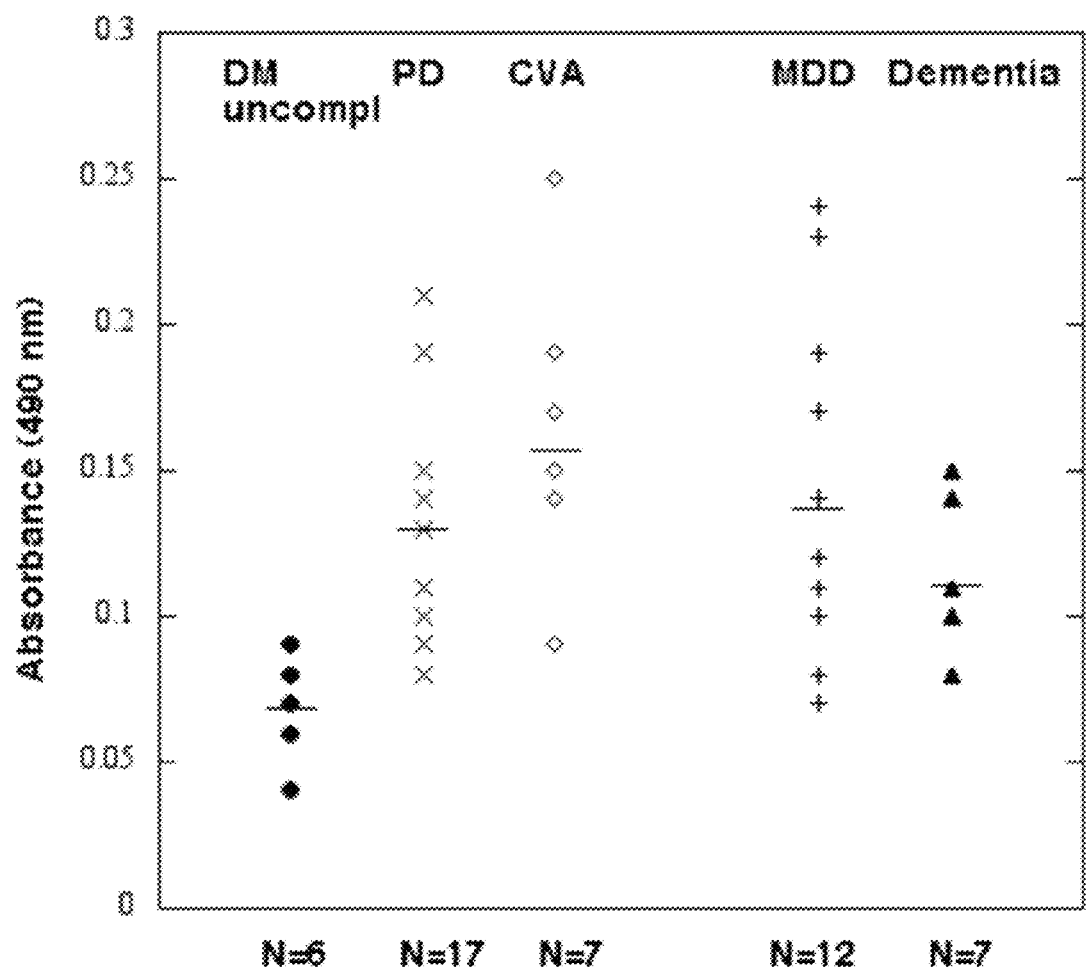
FIG. 14 shows the results of an enzyme linked immunosorbent assay using the synthetic peptide Q...N-18 (SEQ ID NO: 1) as the solid-phase antigen. Results are arbitrary absorbance units (OD) in a one-fortieth dilution of the protein-A eluate fraction of plasma or serum from patients with uncomplicated type 2 diabetes (N=6), Parkinson's disease (PD)(N=17), cerebrovascular accident (CVA)(N=7), major depressive disorder (MDD)(N=12) or dementia (N=7). Dashed line indicates background absorbance level of 0.04 absorbance units.

Increased 5-HT2A receptor synthetic peptide binding in protein-A eluates from subsets of diabetic angiopathy and/or neurovascular complications. A one-fortieth dilution of the protein-A eluate of plasma (2-8 µg/mL IgG) was tested for binding to the linear synthetic peptide Q . . . N-18. Mean binding level was significantly increased (P<0.01) in subsets of diabetes having Parkinson's disease (n=17), dementia (n=7), stroke or TIA (n=7), or major depressive disorder (n=12) compared to the mean level in age-matched older adult type 2 DM without significant angiopathy (i.e., retinopathy or nephropathy) (n=6; FIG. 14). It was also significantly increased in diabetes patients with a coexisting systemic autoimmunity condition (i.e. discoid lupus erythematosus (n=1), ankylosing spondylitis (n=1), Graves orbitopathy (n=2), rheumatoid arthritis (n=1)) (Table 4). Mean binding in the protein-A eluate fraction of T2DM plasma (IgG) was significantly increased in patients having significant retinopathy vs. no retinopathy, or diabetic nephropathy vs. no nephropathy (Table 5). There was no significant difference in plasma IgG autoantibody binding level in T2DM patients with or without atrial fibrillation, T2DM with or without obstructive sleep apnea or T2DM with or without co-morbid cancer (Table 5). Taken together, these data suggest associations among diabetic angiopathy, neurodegenerative disorders and certain systemic autoimmune diseases with increased level of IgG autoantibodies that binds to 5-HT2A receptor, second extracellular loop region, linear synthetic peptide.

Lack of association between IgG plasma autoantibody binding to 5-HT2A receptor peptide and patient age or diabetes duration. There were no significant associations between mean IgG autoantibody binding to the receptor peptide and baseline patient age, body mass index, glycosylated hemoglobin, or duration of diabetes.

Dose-dependence and titer of diabetic protein-A eluate binding to Q . . . N-18. Both titer and potency of IgG autoantibody binding to the Q . . . -N-18 linear synthetic peptide were substantially increased in subsets of diabetes suffering with recurrent stroke, diabetes with co-morbid discoid lupus erythematosus and retinitis pigmentosa, diabetes having dementia and diabetes with Parkinson's disease. The peak binding and titer were not elevated in representative older type 2 diabetes without neurodegeneration and without significant angiopathy (e.g., retinopathy and nephropathy), i.e., <2-fold above background absorbance at IgG concentrations tested between 1-2 µg/mL (Table 6).

Figure 15:
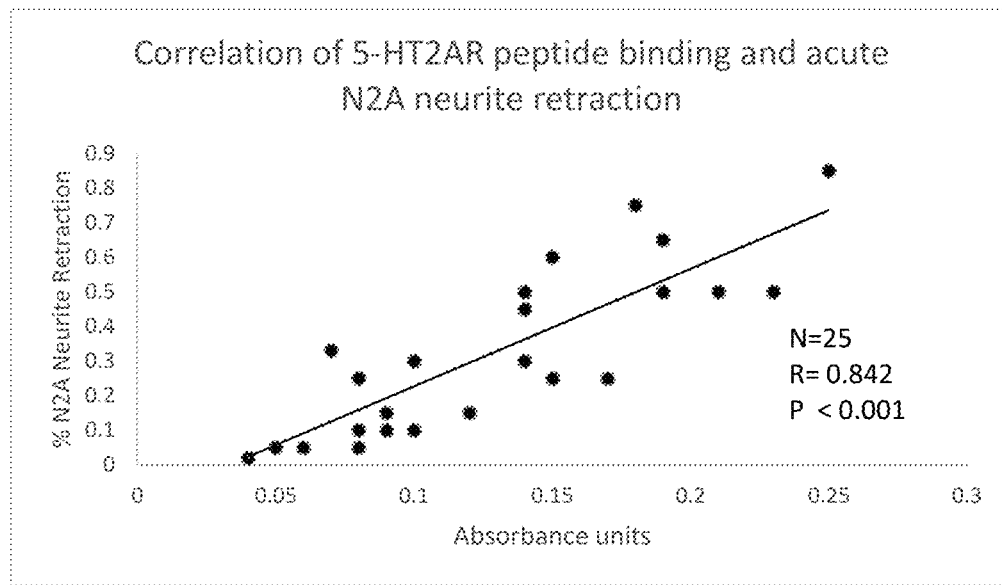
FIG. 15 shows a correlation between 5-HT2A receptor synthetic peptide binding and acute N2A neurite retraction in the protein-A eluates from twenty-five patients with neurovascular or neuropsychiatric complications. A $\frac{1}{40}^{th}$ dilution of the protein-A eluate fraction was incubated with N2A cells and acute neurite retraction was determined. Results were correlated with binding to Q...N-18 (SEQ ID NO: 1) in an ELISA using a $\frac{1}{40}^{th}$ dilution of the protein-A eluate of serum or plasma.
Figure 16:
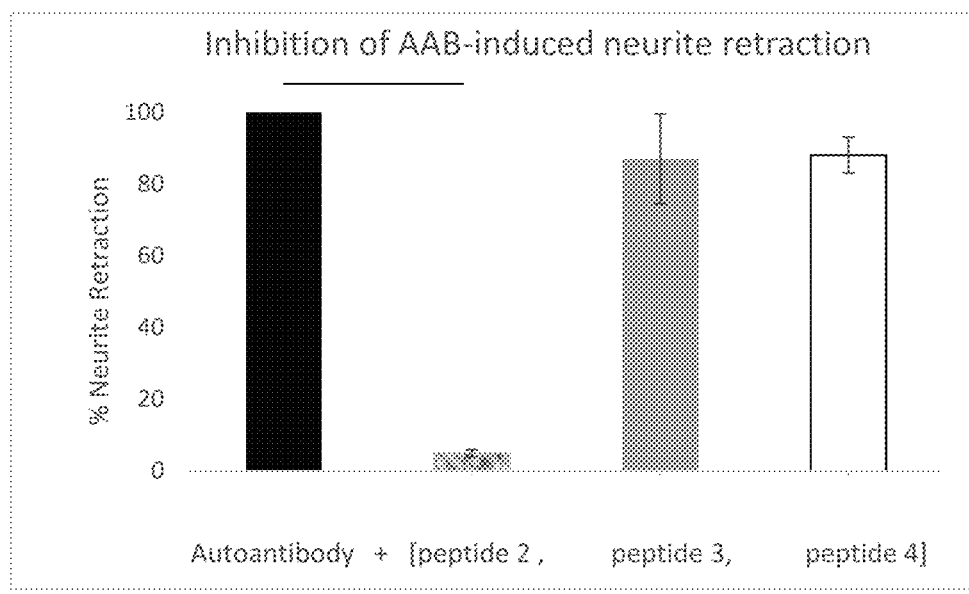
FIG. 16 shows a $\frac{1}{40}^{th}$ dilution of the plasma autoantibodies (AAB) from Pt 1 with refractory hypertension that were incubated with N2A neuroblastoma cells alone (solid bar) or in the presence of a 20 mg/mL concentration of peptide 2 (SCLLADDN; SEQ ID NO: 2), peptide 3 (QDDSKVF; SEQ ID NO: 3), or peptide 4 (VFKEGSC; SEQ ID NO: 4)(open bar). Results are (mean±SD) acute neurite retraction determined.

Correlation of receptor peptide binding with IgG autoantibody neurotoxicity (neurite retraction, N2a cell loss). A significant correlation between 5HT2A receptor synthetic peptide binding and acute N2a neurite retraction in the protein-A eluates from twenty-five patients tested (FIG. 15) was detected including representative patients from various pathologic subgroups (Table 7). High vs low receptor peptide binding subgroups of IgG were also significantly associated with dose-dependent promotion of acute N2a neurite withdrawal, (Table 8), i.e., high binders caused significantly greater neurite retraction at every dilution tested.

Higher receptor peptide binding was also significantly associated with increased IgG-induced N2a accelerated neuron loss after 24 hrs incubation (Table 9). Taken together these data suggest that IgG autoantibody binding to the linear synthetic peptide is highly correlated with IgG autoantibody-induced N2A neurite retraction and accelerated N2a neuron loss.

Soluble ECL2 peptide inhibits DM autoantibody-induced N2a neurite retraction. The 18-meric linear synthetic peptide (Q . . . N-18) dose-dependently inhibited mouse N2A neuroblastoma cell neurite retraction induced by a sixty nanomolar concentration of the protein-A eluate fraction of plasma from Patient 1 with type 2 diabetes suffering with refractory hypertension, retinal vein occlusion, and transient ischemic attack (TIA). The autoantibodies alone from Patient 1 with refractory hypertension caused 90% neurite retraction in N2a cells (Table 10). Half-maximal inhibition of autoantibody-induced acute neurite retraction occurred at a 2 µg/mL concentration of . . . Q N-18, corresponding to ~1 µM concentration of the peptide (Table 10).

Epitope mapping of region within 5-HT2A receptor, linear synthetic 5-HT2A receptor peptide targeted by autoantibodies. Next an epitope analysis was performed to determine the subregion within the 5-HT2A receptor second extracellular domain that binds to the type 2 diabetes pathologies' autoantibodies. Three overlapping short peptides were synthesized (SEQ ID NOs: 2, 3, and 4). N2a cells expressing neurites were pre-incubated with each of the peptides separately (for 5 minutes) prior to the addition of Patient 1, refraction hypertension IgG autoantibodies to determine which of the three peptides could compete for binding to the test diabetic pathologies' autoantibodies causing inhibition of IgG autoantibody-induced neurite retraction. Peptide 3 and 4 had no significant effect on Patient 1 IgG autoantibody-induced neurite withdrawal. Peptide 2 (SEQ ID NO: 2) (20 µg/mL) dose-dependently nearly completely prevented acute neurite retraction induced by Patient 1, refractory hypertension IgG autoantibodies (Table 11).

Subregion-specific 5-HT2AR, linear synthetic 5-HT2A receptor peptide protects against autoantibody neurotoxicity. A twenty microgram per milliliter concentration of Peptide 2 (SEQ ID NO: 2) nearly completely prevented (99%) IgG autoantibody-induced acute neurite withdrawal in a 50-100 nM concentration of pathologies' IgG autoantibodies in ten of ten patients tested (Table 12).

A 20 µg/mL concentration of peptide 2 (SEQ ID NO: 2) completely prevented accelerated N2a neuron loss induced by a one one-hundredth dilution of Patient 1, refractory hypertension IgG autoantibodies (Table 13). After 16 hours' incubation (at 37 degrees C.) with Patient 1 or the IgG autoantibodies from four different patients suffering with stroke, Parkinson's disease, dementia or major depressive disorder, peptide 2 (SEQ ID NO: 2) (20 µg/mL) afforded substantial neuroprotection against accelerated neuron loss (Table 14).

Taken together, these data suggest that the structure of a short linear synthetic peptide comprising a portion of the 5-HT2A receptor is stable to proteolysis and may afford neuroprotection against IgG autoantibodies prevalent in subsets of older adult type 2 diabetes having neurodegeneration, systemic autoimmunity and other significant microvascular angiopathy.

In silico test of 5-HT2A receptor peptide's binding affinity for major histocompatibility complex class II (MHC-II) molecules. The Immune Epitope Database (IEDB) and an improved prediction tool (Jensen K K, et al., *Immunology*. 2018; 154(3):394-406) was used to test whether a portion of the Peptide 2 (SEQ ID NO: 2) amino acid sequence corresponds to an 'immune epitope,' i.e., a sequence which displays significant binding affinity to one or more alleles comprising MHC class II, HLA-DR, HLA-DQ, or HLA-DP molecules. The 15-meric linear peptide sequence(s) SKVFKEGSCLLADDN (SEQ ID NO: 5) which includes Peptide 2 (SEQ ID NO: 2) (underlined) was tested for binding to MHC class II molecules. No significant high affinity binding to alleles comprising the HLA-DR or HLA-DP loci was observed. The core amino acid sequence, KEGSCLLAD (SEQ ID NO: 6) displayed significant binding affinity (i.e., $K_a$ 217 nM), to one specific HLA-DQ allele, DQA10102-DQB10602.

Discussion Type 2 diabetes is not an autoimmune disease. Yet the present data suggest humoral immune responses to the 5-hydroxytryptamine 2A receptor in subsets of older adult obese type 2 diabetes suffering with diabetic macular edema, proteinuric neuropathy. Aging, diffuse vascular injury and visceral obesity may each contribute to humoral immunity to the 5HT2A receptor. A role for chronic inflammation and hemodynamic factors is suggested by the observation of significantly increased linear synthetic 5-HT2A receptor peptide binding in subsets of patients with nephropathy and chronic kidney disease. The high prevalence of increased 5-HT2A receptor peptide binding in autoantibodies from patients suffering with Parkinson's disease (14/17), major depression (9/12), stroke (6/7), and dementia (4/7), is unlikely to represent 'non-specific binding' since autoantibody binding (in the ELISA) was significantly associated with both autoantibody-induced neurite retraction and accelerated N2A cell loss. The correlation between receptor peptide binding and neurotoxicity demonstrated herein suggests that neurovascular IgG autoantibody binding to the 5-HT2AR second extracellular loop causes receptor activation which as previously reported was positively coupled to PLC/IP3/Ca2+ and RhoA/ROCK signaling pathway activation (Zimering M B, *J Endocrinol Diabetes*. 2018; 5(2); and Zimering M B, *J Endocrinol Diabetes*. 2017; 4(4)).

The second extracellular loop region loop lies in close proximity to the orthosteric binding pocket (OBP) (Wacker D, et al. *Cell*. 2017; 168(3):377-389) and has a role in preventing normal constitutive receptor activation in biogenic and trace amine G-protein coupled receptors (GPCRs) (Michino M, et al. *Pharmacol Rev* 2015; 67:198-213). Neurovascular pathologies' autoantibodies appeared to target a conserved subregion in the second extracellular loop (Michino M, et al. *Pharmacol Rev* 2015; 67:198-213), important in promoting sustained activation of the 5HT2B and 5HT2A receptors by the hallucinogenic drug lysergic acid diethylamine (LSD) (Wacker D, et al. *Cell*. 2017; 168(3):377-389). In a recent study by Wacker et. al., the atomic structure of LSD complexed to the 5-HT2B and -2A receptors was reported. Lysergic acid diethylamine, known to have long-lasting effects in humans, exhibited unusually long residence times at the 5-HT-2B and -2A receptors, i.e., off-reaction times of ~45 minutes and ~220 minutes, respectively (Wacker D, et al. *Cell*. 2017; 168(3):377-389). Wacker and co-authors reported that amino acid residues 207-214 in 5-HT2BR form a 'lid' which blocks the opening to the orthosteric binding pocket likely accounting for LSD's prolonged off-reaction time at the receptor (Wacker D, et al. *Cell*. 2017; 168(3):377-389). Of interest, seven of the eight amino acid residues comprising the inhibitory (decoy) Peptide 2 sequence SCLLADDN (SEQ ID NO: 2) (underlined here) form the corresponding 'lid' region in the 5-HT2A receptor, including the conserved amino acid residue, leucine 229 (bolded), which is present in the three 5-HT2 (-A, -B, and -C) receptor isoforms (Michino M, et al. *Pharmacol Rev* 2015; 67:198-213). One of the striking features of the neurovascular pathologies' autoantibodies effect in N2A cells was its long duration of action, i.e. neurite retraction was irreversible after 45 minutes' or longer observation times. Serotonin or the 5HT2A receptor agonist DOI promoted neurite retraction which peaked after (3-5 minutes) and was reversible at longer times (Zimering M B, *J Endocrinol Diabetes*. 2017; 4(4)). Taken together with the structural data on the LSD bound 5-HT2R (Wacker D, et al. *Cell*. 2017; 168(3):377-389). These data suggest that neurovascular autoantibodies may be binding at an important region in the second extracellular loop involved in stabilizing a 'persistently-active' conformation of the 5HT2A receptor.

Systemic autoimmunity is associated with a wide variety of autoantibodies capable of targeting diverse autoantigens. As described herein, highest binding to the 5-HTR2AR linear synthetic peptide occurred in two patients with a systemic autoimmune condition, i.e., discoid (cutaneous) lupus erythematosus (Pt 2) or HLAB27-positive ankylosing spondylitis. Heparan sulfate proteoglycans (HSPG) are among a small group of overlapping autoantigens reported in both systemic lupus erythematosus (Shibata S, et al. *Clin Immunol Immunopathol*. 1994; 70(2):114-23) and ankylosing spondylitis (Wright C, et al., *Mol Cell Proteomics*. 2012; 11(2):M9.00384). Heparan sulfate proteoglycans are strongly anionic at physiologic pH. They are abundantly expressed in extracellular matrix and on vascular and neuronal surfaces where they have role(s) in the maintenance of tissue barriers and serve as low-affinity co-receptors for cationic 'heparin-binding' growth factors, e.g., basic fibroblast growth factor (FGF-2) (Bemfield M. et al., *Philos Trans R Soc Lond B Biol Sci* 1990; 327:171-186). Neurotoxic and endothelial cell inhibitory autoantibodies previously reported in subsets of diabetes complicated by painful neuropathy, nephropathy, macular edema or primary open angle glaucoma (Zimering M B et al., *Diabetes Res Clin Pract*. 2011; 93(1):95-105; and Zimering M B, *J Endocrinol Diabetes*. 2018; 5(2)) displayed increased affinity for heparan sulfate proteoglycan (Zimering M B et al., *Diabetes Res Clin Pract*. 2011; 93(1):95-105) or a heparin Sepharose column (Zimering M B, et al., *Metabolism* 58:393-400). Glomerular HSPG are elaborated in diabetic nephropathy (Makino H et al., *Nephron*. 1992; 61(4):415-21) and may be a target of heightened humoral autoimmunity, and, in particular, under conditions of chronic inflammation which prevail in chronic kidney disease.

The putative dominant epitope targeted by 5-HT2A receptor activating autoantibodies described herein contains a di-aspartic acid motif (SCLLA<u>DD</u>N; SEQ ID NO: 2) not present in the 5-HT2B receptor (Michino M, et al. *Pharmacol Rev* 2015; 67:198-213). It is interesting to speculate that the negative charge(s) associated with having di-aspartic acid residues in a solvent-exposed region of the receptor may provide a basis for strong electrostatic interaction with circulating IgG pathologic autoantibodies. In a prior report, neurotoxicity was enhanced eight-fold following chromatography of plasma on a dextran sulfate affinity chromatography column using IgG autoantibodies from diabetic dementia and PD dementia patients (Zimering M B, *J Endocrinol Diabetes*. 2018; 5(2)). Dextran sulfate (Liposorber) apheresis is used to lower excessive concentrations of cationic lipoprotein particles (very low density, and low-density lipoproteins) in the circulation in patients with familial hypercholesterolemia. It is possible that autoantibodies associated with neurovascular pathologies co-purified with cationic lipoprotein particles based on having similar cationic surface charge characteristics may contribute to an electrostatic interaction with anionic sulfate groups.

Prostate expresses high level of HSPG (Kosir M A, et al., *J Surg Res* 1995; 58(1):46-52), which acts as a co-receptor for several different fibroblast growth factors having important role(s) in stromal proliferation underlying prostate cancer progression (Wu X, et al., *Cancer Res*. 2001; 61(13): 5295-302). Among nine patients in the present study who had co-morbid prostate (n=8) or bladder (n=1) cancer, the mean level of 5-HT2AR autoantibody peptide binding was 0.14 AU, i.e., 3.5-fold higher than background (0.04 AU). Eight of the nine prostate or bladder cancer patients suffered with a neurodegenerative (n=5 PD, n=1 dementia) or neuropsychiatric disorder (N=1 MDD, N=1 schizophrenia). In most of these patients, the cancer diagnosis and treatment was established prior to the onset of neurologic or neuropsychiatric disease manifestations perhaps consistent with a paraneoplastic mechanism for humoral autoimmunity to 5-HT2A receptor activating autoantibodies. In a prior report, prostate cancer autoantibodies in patients suffering with fatigue/depression were highly neurotoxic and evoked large increases inward cationic current in (whole-cell patch clamped) rat hippocampal pyramidal neurons associated with long-lasting desensitization of excitatory synaptic inputs (Zimering M B et al., *Diabetes Res Clin Pract*. 2011; 93(1):95-105). Taken together with the present data, these findings suggest that 5-HT2A receptor found on cortical pyramidal neurons or in other brain regions may mediate glutamatergic excitatory post-synaptic actions in response to 5-HT2A receptor-activating autoantibodies (Aghajanian G K, et al., *Neuropharmacology*. 1997; 36(4-5):589-99).

A short linear synthetic peptide comprising a region of the second extracellular loop of the 5HT2A receptor, i.e., peptide 2 (SEQ ID NO: 2), largely prevented autoantibody-induced neurotoxicity perhaps by competing for binding to the region of the 5-HT2R targeted by a majority of the autoantibodies tested. The peptide antagonist (e.g., a decoy peptide) (SCLLADDN; SEQ ID NO: 2) retained its neuroprotective effect (against autoantibody-induced N2A cell loss) even after 16 hours' incubation time (at 37 degrees C.) in the presence of 10% fetal calf serum. A hallmark property of an autoantigen's immunodominant epitope is its ability to survive complete intracellular proteolytic processing (Kim A, et al., *Curr Opin Immunol*. 2015; 34:9-15). The data from the in silico analysis suggests that Peptide 2 having the sequence SCLLADDN (SEQ ID NO: 2) may comprise an immunodominant peptide which is specifically 'recognized' by the major histocompatibility complex class II molecular system through high affinity binding interaction with the specific HLA-DQ allele, DQA10102-DQB10602. Of interest, DQA10102-DQB10602 was previously reported to have conferred markedly increased susceptibility to narcolepsy-cataplexy in certain populations (Mignot E, et al., *Am J Hum Genet*. 2001; 68(3):686-99). Narcolepsy is a putative neurodegenerative process affecting hypocretin neurons located in the lateral hypothalamus (Nishino S, et al., *Lancet*. 2000; 355(9197):39-40). Narcolepsy incidence rates in young adults were reported to have peaked following the 2009 H1N1 influenza pandemic (Nohynek H, et al., *PLoS One*. 2012; 7(3):e33536) and related H1N1 vaccination regimes (Han F, et al., *Ann Neurol*. 2011; 70(3):410-417) suggesting molecular mimicry with certain strains of influenza viruses as one possible mechanism for T-cell driven autoimmunity in the unknown etiology of a subset of 'autoimmune' narcolepsy-cataplexy in HLA-DQ susceptible persons (Black J, III, et al., *Sleep* 2005; 28: 1191-1192).

Highest level of 5-HT2AR, second extracellular loop autoantibody binding, i.e., 6.25 times above background, occurred in an older man (Patient 2) having discoid lupus erythematosus, and near blindness secondary to central retina artery occlusion and retinitis pigmentosa. It is of interest that 5-HT2AR immunoreactivity was reported on the terminals of photoreceptors and bipolar cells in rabbit retina (Pootanakit K, et al., *Vis Neurosci*. 1999; 16: 221-230). In addition, 5-HT2AR antagonists afforded protection against light-induced photoreceptor degeneration in certain susceptible genetic strains of mice (Chen Y, et al., *J Biol Chem*. 2012; 287(7):5059-5069). Plasma autoantibodies in Patient 3, an 81 year-old-man who suffered with autoimmune thyroid disease and juvenile-onset retinitis pigmentosa (i.e., Stargardt disease), displayed significantly increased binding (2.5-fold background) in the ELISA. Taken together, these data suggest systemic autoimmunity in which humoral autoantibodies are directed against many different autoantigen epitopes, might provide a humoral-mediated mechanism contributing to retinal degeneration occurring in genetically-susceptible patients. The 5-HT2AR second extracellular loop peptide-based ELISA might be useful in screening family members of affected patients suffering with genetic forms of retinal degeneration. These data suggest that SEQ ID NO: 2 may be useful as a neuroprotective agent in retinal degeneration.

The source(s) of 5-HT2AR autoantigen in angiopathic type 2 diabetes is not known. Obese diabetes is associated with increased inflammation and the latter is associated with higher risk of thrombosis. Since 5-HT2AR is expressed on platelets, it is possible that diabetic microangiopathy predisposes to microthrombi formation at sites of inflammation which may cause 5HT2A receptor to be taken up and processed by macrophages and/or other professional antigen presenting cells. Monocytes have been reported to adhere to platelets at sites of inflammation via specific interactions not observed between platelets and other subtypes of white blood cells (Passacquale G, et al., *PLoS One.* 2011; 6(10): e25595).

The study described herein was cross-sectional and included mostly older men. A longitudinal study in diverse (unselected) populations may be useful to estimate the actual prevalence of 5-HT2AR-activating autoantibodies and whether a dose-response relationship exists between the 5HT2A receptor autoantibodies and one or more neurodegenerative disorders.

In summary, the present data provide evidence that subsets of major depressive disorder, Parkinson's disease, dementia, small vessel stroke (e.g., retinal artery occlusion), refractory hypertension, and proteinuric nephropathy (in both diabetes and obese non-diabetic older persons) harbored IgG autoantibodies (e.g., 5HT2A receptor autoantibodies) which bound to a region of the second extracellular loop of the human 5HT2A receptor (Wacker D, et al., *Cell.* 2017; 168(3):377-389) previously implicated in causing long-lasting receptor activation and for which the decoy peptide as described herein can be used as a viable treatment. Because the highest binding of the decoy peptide to the 5-HTR2A receptor autoantibody occurred in patients having discoid (cutaneous) lupus erythematosus and autoimmune retinitis pigmentosa, or in patients having HLAB27-positive ankylosing spondylitis, a composition comprising the decoy peptide as described herein may alleviate symptoms of and/or treat these diseases.

The present data are also consistent with prior reports that endothelial cell inhibitory and neurotoxic autoantibodies increased in diabetic subsets having neurologic (e.g., painful neuropathy, open angle glaucoma, dementia, major depressive disorder, Parkinson's disease) and/or microvascular complications (Zimering M B, *J Endocrinol Diab* 2017; 4(4): 1-10; and Zimering M B, *J Endocrinol Diab* 2018; 5(2): 1-11). Autoantibody binding to a linear synthetic peptide corresponding to the second extracellular loop of human 5HT2AR was significantly correlated with preventing both autoantibody-induced neurite retraction and accelerated N2A cell loss suggesting that autoantibody binding induces 5-HT2A receptor activation as was previously shown to positively couple to PLC/IP3/Ca2+ pathway and RhoA/ROCK activation (Zimering M B, et al. (2016) *J Endocrinol Diab* 3(1): 1-14; Zimering M B, et al. (2015) *J Endocrinol Diab* 2015; 2(2): 11; Zimering M B, et al., (2013) *Front. Endocrinol.* 4:58; Zimering M B. *Endocr Pract.* 2010, 16(5): 842-850; Zimering M B, et al., *Diabetes Res Clin Pract.* 93(1): 95-105, 2011; Zimering M B, et al., *Metabolism,* 58(6), 882-887, 2009; Zimering M B, et al., *J Clin Endo Metab,* 94(6), 2171-2177, 2009; and Zimering M B, et al., *Front. Endocrinol.* 2014; doi: 10.3389/fendo.2014.00128).

TABLE 1

Baseline clinical characteristics in the 56 study patients

| Risk factor | Mean (SD) | N |
| --- | --- | --- |
| Age | 68.3 (9.0) | 56 |
| Non-diabetes * | 61.8 (10.8) | 7 |
| Type 2 Diabetes | | 49 |
| Body mass index | 34.9 (6.8) | 49 |
| Glycosylated hemoglobin | 8.0 (1.6) | 49 |
| Duration of diabetes (years) | 15.4 (8.2) | 49 |

* Major depressive disorder (n = 2), Parkinson's disease (n = 33), Schizophrenia (n = 11), Graves ophthalmopathy (n = 1)

TABLE 2

Comparison of age and body mass index in diabetic and non-diabetic patients

| | Diabetes (n = 49) | No Diabetes (n = 7) | P-value |
| --- | --- | --- | --- |
| Age | 69.0 (7.2) | 61.8 (10.8) | 0.04 |
| BMI | 34.9 (6.8) | 31.0 (3.0) | 0.26 |

Results are mean +/(SD)

TABLE 3

Mean 5-HT2A receptor peptide binding in diabetic vs nondiabetic patients having Parkinson's disease or major depressive disorder

| Neurodegeneration | Diabetes | No Diabetes | P-value |
| --- | --- | --- | --- |
| Parkinson's disease | 0.13 (0.04) [14] | 0.13 (0.05) [3] | 0.85 |
| Major depression | 0.16 (0.06) [9] | 0.12 (0.04) [2] | 0.32 |

TABLE 4

Mean 5-HT2A receptor peptide binding in type 2 diabetes without angiopathy vs. diabetes with a neurodegenerative disorders or a co-morbid systemic autoimmune condition^^

| | Mean receptor peptide binding. | N | P-value* |
| --- | --- | --- | --- |
| Diabetes without angiopathy^ | 0.068 (.01) | 6 | — |
| Diabetes with dementia | 0.11 (.02) | 7 | <0.01 |
| Diabetes with PD** | 0.13 (.04) | 17 | <0.01 |
| Diabetes with MDD*** | 0.14 (.05) | 12 | 0.02 |
| Diabetes with CVA or TIA | 0.16 (.04) | 7 | <0.01 |
| Diabetes with Autoimmunity | 0.18 (.05) | 5 | <0.01 |

Results are mean AU +/− SD;
^without any neurodegenerative disorder;
^^N = 1each having discoid lupus erythematosus, ankylosing spondylitis, Graves' disease, celiac disease, rheumatoid arthritis;
*t-test compared to group having diabetes without angiopathy.
PD—Parkinson's disease,
MDD—major depressive disorder,
CVA—cerebrovascular accident,
TIA—transient ischemic attack.
**includes 3 patients without diabetes;
***includes 2 patients without diabetes

TABLE 5

Association between 5-HT2A receptor second extracellular loop peptide binding and baseline diabetic micro-vascular or other complications

|  | Present (N) | Absent (N) | P-value |
|---|---|---|---|
| Diabetic retinopathy | 0.15 ± 0.05 (16) | 0.10 ± 0.04 (27) | 0.002 |
| Diabetic nephropathy | 0.13 ± 0.04 (21) | 0.1 ± 0.04 (21) | 0.006 |
| Diabetic painful neuropathy | 0.13 ± 0.05 (21) | 0.1 ± 0.05 (19) | 0.12 |
| Atrial fibrillation | 0.13 ± 0.05 (19) | 0.13 ± 0.05 (34) | 0.87 |
| Obstructive sleep apnea | 0.12 ± 0.05 (20) | 0.12 ± 0.05 (28) | 1.0 |
| Cancer | 0.14 ± 0.05 (13) | 0.12 ± 0.05 (36) | 0.13 |

Results are mean AU +/− SD; Patients having co-morbid systemic autoimmune condition (n = 5) were excluded except in two cases having retinal neurodegeneration.

TABLE 6

Potency and titer of receptor peptide autoantibodies in representative patients

| Diagnosis | Titer of autoantibody | Peak Binding (AU) |
|---|---|---|
| Retinitis pigmentosa & Discoid lupus erythematosus | 0.37 µg/mL | 0.25 |
| DM, Refractory hypertension | 2 µg/mL | 0.17 |
| DM, Dementia | 0.4 µg/mL | 0.14 |
| DM, Parkinson's disease | <1 µg/mL | 0.10 |
| DM without ND | 1 µg/mL | 0.07 |
| DM without angiopathy | 2 µg/mL | 0.06 |

Absorbance units = 0.04 is background level. 1 ug/mL IgG ~6.7 nM.
ND—neurodegenerative disorder,
DM—diabetes mellitus;
Titer—concentration of autoantibodies causing ~50% of maximal binding.

TABLE 7

Association between autoantibody-5HT2A receptor peptide binding and autoantibody-induced acute neurite retraction by representative patient subgroup

| Diagnosis | Binding | Neurite retraction* |
|---|---|---|
| Diabetes without angiopathy (n = 3) | .04 | − |
|  | .06 | − |
|  | .08 | − |
| Dementia (n = 2) | .15 | ++ |
|  | .14 | +++ |
| Schizophrenia (n = 4) | .08 | ++ |
|  | .08 | ++ |
|  | .10 | − |
|  | .07 | ++ |
| Major depressive disorder (n = 2) | .14 | ++ |
|  | .23 | +++ |
| Parkinson's Disease (n = 7) | .14 | +++ |
|  | .19 | +++ |
|  | .10 | ++ |
|  | .15 | ++++ |
|  | .19 | ++++ |
|  | .21 | +++ |
|  | .09 | + |
| Stroke (n = 2) | .18 | +++++ |
|  | .25 | +++++ |

*Neurite retraction scale:
% neurite shortening after 5 minutes 'exposure to autoantibodies, i.e.
0-10% =(−);
11-24% =(+);
25-33% (++);
34-50% (+++);
51-74% (++++);
75-85% (+++++).

TABLE 8

Dose-dependent, increased autoantibody-induced neurite retraction in DM having neurodegeneration or cancer compared to DM without neurodegeneration or cancer

| Diagnosis | Receptor Peptide Binding (AU) | Antibody Dilution | | | |
|---|---|---|---|---|---|
|  |  | 1/40th | 1/60th | 1/100th | 1/200th |
| PD(1), Stroke (2), Prostate cancer (1) | High binders (0.21 ± .03) | 72 ± 13 %^ | 44 ± 6%* | 33% | 25% |
| Schizophrenia (1), uncompl DM (2) | Low binders (0.06 ± .01) | 20 ± 12 % | 13 ± 10% | ND | ND |

Results are mean ± SD % neurite retraction after 5 minutes exposure to indicated dilution of autoantibodies;

NR- no detectable neurite retraction.

^ $P < 0.002$;

*$P < 0.02$ - compared to neurite retraction at same autoantibody dilution in low peptide binding IgG autoantibodies subgroup;

AU- absorbance units,

SD-standard deviation.

Uncompl(icated) diabetes mellitus- without microvascular complications.

TABLE 9

Association between autoantibody receptor peptide binding and autoantibody-induced accelerated N2a neuron loss

|  | Low-binding (N = 7) | High-binding (N = 5) | P-value |
|---|---|---|---|
| Absorbance (AU) | 0.08 ± 0.019 | 0.22 ± 0.04 | <0.001 |
| % N2a cell survival | 91.7 + 5.9% | 66.4 + 9.1% | <0.001 |

Results are mean +/− SD.
Neuron survival was determined after 24 hours incubation.

TABLE 10

Dose-dependent inhibition of autoantibody-induced acute N2A neurite withdrawal by co-incubation with 18-meric Q..N linear synthetic peptide Autoantibody (one sixtieth dilution) + (Q...N-18) at

| Diagnosis | (0 µg/mL) | (3 µg/mL) | (5 µg/mL) |
|---|---|---|---|
| DM, refractory hypertension (N = 1) | 90 + 5% | 25 + 7% | 0 + 0% |

The indicated concentration of the Q . . . N-18 linear synthetic 5HT2A receptor peptide was co-incubated with a 100 nM concentration of autoantibodies from Patient 1, diabetes (DM) refractory hypertension. Acute N2A neurite retraction was assessed after 5 minutes.

TABLE 11

Identification of a short linear peptide that blocks autoantibody (IgG)-induced neurite retraction

| Treatment | Mean acute N2a neurite retraction (%) |
|---|---|
| DM, refractory hypertension IgG* | 100 + 0% |
| Pt1 IgG + Peptide 3 (QDDSKVF; SEQ ID NO; 3) | 87 + 19% |
| Pt1 IgG + Peptide 2 (SCLLADDN; SEQ ID NO; 2) | 5 ± 5%* |
| Pt1 IgG + Peptide 4 (VFKEGSC; SEQ ID NO; 4) | 88 + 13% |

*A one-fortieth dilution of the Pt 1 diabetic refractory hypertension IgG autoantibodies was incubated in the presence or absence of a 20 µg/mL concentration of three different short linear synthetic peptides comprising portions of the second extracellular loop of 5-HT2A receptor. Results are mean +/SD acute N2A neurite retraction after 5 minutes. Peptide 2 (SEQ ID NO: 2)(20 µg/mL) was associated with 95% protection against the diabetic stroke pathologies IgG-induced neurite retraction. Peptide 3 (SEQ ID NO: 3) or Peptide 4 (SEQ ID NO: 4) at identical (20 µg/mL) concentration had no significant protective effect on IgG autoantibody-induced N2A neurite retraction.

TABLE 12

Neutralization of diabetic autoantibody-induced N2a acute neurite retraction by a linear synthetic short peptide contained within the 5-HT2A receptor second extracellular loop region, e.g., Peptide 2 (SEQ ID NO: 2).

Acute N2a neurite retraction in IgG autoantibodies

| Pathologic Autoantibodies (N = 10) | (without Peptide 2) | (with Peptide 2) | P-value |
|---|---|---|---|
| Dementia (2), PD (3), Stroke (2), Schizophrenia (3) | 33% + 8% | 0.25% + 0.75% | <0.001 |

PD-Parkinson's disease

TABLE 13

Neutralization of diabetic autoantibody (IgG(-induced accelerated N2a cell loss by Peptide 2 (SEQ ID NO: 2), a short linear synthetic peptide corresponding to a portion of 5-HT2AR second extracellular loop region

| Pathology | Pt 1, IgG alone | Pt, IgG + Peptide 2 | P-value |
|---|---|---|---|
| DM refractory HTN (n = 1) | 57 + 3% | 100 + 4% | 0.005 |

A 1/100th dilution of the diabetes (DM) refractory hypertension (HTN), plasma IgG autoantibodies was incubated for 16 hours in the presence or absence of a 20 µg/mL concentration of the linear synthetic peptide, Peptide 2.
Results are mean +/− (SD) percent of basal N2A neuroblastoma cell survival.

TABLE 14

Neutralization of diabetic autoantibody (IgG)-induced accelerated N2a cell loss by Peptide 2 (SEQ ID NO: 2), a short linear synthetic peptide corresponding to a portion of 5-HT2AR second extracellular loop region

| Diagnosis (N = 5) | IgG alone | IgG+Peptide 2 | P-value |
|---|---|---|---|
| Stroke (2), PD(1), Dementia (1), MDD(1) | 64 + 21% | 94 + 11% | 0.03 |

Results are mean ± SD N2A cell survival after 16 hours incubation of the indicated diabetic pathologies IgG autoantibodies in the presence or absence of 20 µg/mL Peptide 2 (SEQ ID NO: 2).
PD-Parkinson's disease, MDD-maj or depressive disorder Example 2: Testing Decoy Peptides in Zucker Diabetic Fatty Rat Background: Traumatic brain injury (TBI) contributes to substantially increased global disability and has been associated with major depression, suicide and cognitive dysfunction through unknown mechanisms. Diabetes increases in older adults and is a risk factor for both traumatic brain injury and major depressive disorder. A recent study found increased autoantibodies in the bloodstream of older patients with diabetes and depression. The autoantibodies targeted a 5-hydroxytryptamine 2A receptor on vascular cells and brain cells which are known to be involved in the mechanism of action of certain classes of anti-depressant medications. The proposed experiments will investigate whether Zucker diabetic fatty (ZDF) rats, which harbor a mutation in the leptin receptor causing obesity, hypertension, diabetes and hyperlipidemia and representing a rat model of obese hypertensive type 2 diabetes, which are subjected to a lateral percussion mild traumatic brain injury, will exhibit worsening 1) anhedonia, and 2) impairment of spatial working memory compared to sham-injured ZDF rats or age-matched Zucker lean rats without diabetes, hypertension or hyperlipidemia.

Introduction: Injury to the blood brain barrier following mild TBI (induced by lateral percussive injury to the brain in rats) may allow entry of harmful 5-HT2A receptor activating autoantibodies from the circulation into brain regions mediating mood and thinking, and memory. Because the neurotoxic autoantibodies displayed long-lasting stability in vitro (activity survived storage at 4 degrees C. for five years or longer, and heating to 56 degrees C. for 30 minutes), their entry into the brain could mediate long-lasting cognitive decline and worsening of depressive symptoms.

It will be tested whether a decoy peptide having an amino acid sequence corresponding to a portion of the mammalian 5-hydroxytryptamine receptor to which 5-HT2A receptor-activating autoantibodies bind can afford neuroprotection (including acute blood pressure-lowering) against the harmful effects of circulating spontaneously-occurring 5-HT2A receptor autoantibodies when the decoy peptide is administered subcutaneously or intravenously immediately prior to the induction of mild traumatic brain injury by lateral percussion injury in rats harboring or 5-HT2A receptor autoantibodies.

Recent studies demonstrated increased level of plasma autoantibodies capable of activating the 5-HT2A receptor on mouse neuroblastoma N2a cells in plasma from human subsets of diabetic depression, diabetic morbid obesity and diabetic or non-diabetic Parkinson's disease and similar kinds of 5-HT2A receptor activating autoantibodies in plasma from Zucker diabetic fatty rats (a rat model of obese type 2 diabetes), but not in selected age-matched Zucker lean rats which do not develop diabetes. The 5-HT2A receptor is highly expressed in the mammalian prefrontal cortex, hippocampus and striatal brain regions mediating mood, perception, thinking, memory and normal movement. It is also expressed in the hypothalamus and brainstem, regions involved in feeding, sleep, respiration and other vegetative functions. The 5-HT2A receptor is an established drug target for a wide range of FDA-approved specific antagonist medications of proven efficacy in the treatment of major depressive disorder, schizophrenia, and Parkinson's disease-related psychosis. It was previously demonstrated that intracerebroventricular (icy) injection of diabetic plasma autoantibodies from patients suffering with refractory depression induced anhedonia in mice (n=16) (i.e., decreased sucrose preference) compared to icv injection of an identical concentration of plasma autoantibodies from euthymic age-matched diabetic patients, the latter had no significant effect on decreased sucrose consumption (i.e., anhedonia) in littermate, age-matched mice (n=16) (Zimering M B, Behnke J A, Thakker-Varia S, Alder J (2015) Autoantibodies in human diabetic depression inhibit adult neural progenitor cells in vitro and induce depressive-like behavior in rodents. J Endocrinol Diab 2015; 2(2): 11).

Results: The data demonstrated that neurotoxic IgG autoantibodies in plasma from the 10-week-old Zucker diabetic fatty rat, a model of adult type 2 diabetes in which genetic obesity (homozygous mutation in the leptin receptor gene fa/fa) causes hyperglycemia and dyslipidemia. Plasma was applied to a Protein G affinity chromatography column (which binds most subclasses or rat IgG autoantibodies), washed extensively and eluted in low pH (2.7) buffer. The resulting eluate was incubated with N2a neuroblastoma cells at 37 degrees C. for 24 hours. The ZDF rat plasma protein G eluate (at concentrations ranging from 0.5-2.5 µg/mL~3-15 nM) caused dose-dependent inhibition of neuroblastoma cell survival (FIG. 1). Following dialysis on a 10 kD MW cut-off membrane, most of the neural inhibitory activity appeared in the retained fraction consistent with an IgG substance having apparent MW>10 kD. Co-incubation with a 1 µM concentration of either M100907 or spiperone, a highly or a less selective, potent 5-HT2A receptor antagonists respectively, significantly reduced accelerated neuroblastoma cell death induced by 1 µg/mL (10 nM) concentration of the ZDF rat protein G eluate (FIG. 1). Taken together, these data suggest the existence of agonist 5-hydroxytryptamine 2A receptor autoantibodies in plasma from the Zucker Diabetic fatty rat.

Experimental Design: Subjects: Four groups of age-matched 10-week old rats: Zucker diabetic fatty and Zucker lean rats (sham-injured vs. subjected to a lateral percussive injury which mimics human mild TBI) will be tested (n=12 animals in each subgroup).

Lateral percussive injury: Injury will be delivered in anesthetized rats using a computer-controlled device that delivers 20 PSI peak pressure having a latency of 20 milliseconds to the dura in a focal temporal region of the brain exposed by prior surgery. Animals will be allowed to recover for 1-2 days prior to behavioral testing.

Experiment 1: To determine the effect of TBI in diabetic ZDF rats, ZDF Obese and Lean rats will receive a lateral fluid percussion or a sham injury. The production of autoantibodies, cognitive decline and depression symptoms will be assessed. Autoantibody production, cognition and depression symptoms will be measured prior to injury, and at 1 and 3 months after injury. To assess cognitive function, short-term spatial memory will be tested using Morris water maze protocol. The depression symptoms of anhedonia and despair will be investigated using a saccharine preference test and forced swim test, respectively. One to two ml of blood will be drawn and then processed for use in a bioassay to determine the amount of autoantibody produced. Non-invasive blood pressure will also be obtained approximately 2-4 weeks between readings.

The experimental design of the study will be: 2 (sham vs TBI)×2 (ZDF obese vs lean)×10 rats/group=40 rats. An extra 8 rats (20%) will be added to account for any loss of rats due to injury at moderate severity and uncertainty in how ZDF rats will respond to TBI. Total rats=48.

Statistical Analysis: Group differences will be evaluated using a mixed design ANOVA with rat strain and sham/TBI as between subjects factors and time after injury as a within subject factor. Post hoc analysis will be performed with a Tukey's Honestly Significant Difference test when appropriate. Significance level will be alpha=0.05.

Experiment 2: To test whether autoantibodies associated with diabetes are causally affecting mood and/or memory after TBI by administering serotonin receptor antagonists, ZDF obese rats will be given a lateral fluid percussion injury or sham injury. Ketanserin, FDA-approved, known 5-HT2A receptor antagonist (1-2 mg/kg, s.c.) or decoy peptide (Peptide 2, Peptide 1) (1-2 mg/kg, s.c.) will be administered daily or every other day for (10 days) before behavioral tests. As in Experiment 2, memory and depression symptoms will be assessed prior to, 1 week, 1 month and 3 months after injury. One to two ml of blood will be drawn and then processed for use in a bioassay to determine the amount of autoantibody produced. Non-invasive blood pressure will also be obtained approximately bimonthly or monthly.

The experimental design of the study will be: 2 (Sham vs TBI)×3 (vehicle, ketanserine, decoy peptide)×10 rats/group=60 rats+12 (20% additional rats) for loss due to surgery or injury=72 ZDF obese rats.

Group differences will be evaluated using a mixed design ANOVA with sham/TBI and drug as between subjects factors and time after injury as a within subject factor. Post hoc analysis will be performed with a Tukey's Honestly Significant Difference test when appropriate. Significance level will be alpha=0.05.

Outcome Measures: It is expected that lateral percussive injury will be associated with significantly greater impairment of memory and worse depression symptoms in Zucker diabetic fatty rats harboring spontaneously-occurring 5-HT2A receptor activating autoantibodies compared to Zucker lean rats without the spontaneously-occurring 5-HT2A receptor autoantibodies. It is also expected that statistically significant group differences will be found on the memory and depression symptoms tasks in the Zucker diabetic fatty rats that are pre-treated with a decoy peptide (e.g., Peptide 1 or Peptide 2) compared to ZDF rats that do not receive the decoy peptide prior to lateral percussive TBI injury. The results of these experiments can provide in vivo proof-of-concept evidence that a decoy peptide, (e.g., Peptide 2, Peptide 1) when administered around the time of traumatic brain injury can provide significant neuroprotection against harmful long-term neurologic sequelae (e.g., depression, cognitive decline, memory impairment) associated with the traumatic brain injury. It will also be tested whether acute administration of a decoy peptide (e.g., Peptide 2, Peptide 1) pre-traumatic brain injury causes acute blood pressure lowering in hypertensive ZDF rats, and whether the blood pressure-lowering effect is sustained for several hours or longer. Since ZDF rats express moderate-severe hypertension which is a major contributor to their development of kidney dysfunction characterized by increased urinary protein excretion, any sustained blood-pressure lowering effects of a decoy peptide (e.g., Peptide 2, Peptide 1) would be indicative of a reno-protective effect, i.e., delay or reduction in the risk of development of kidney dysfunction leading to kidney failure.

Example 3: Serotonin 2A Receptor Autoantibodies Increase in Adult Traumatic Brain Injury in Association with Neurodegeneration Abstract. Objective: Traumatic brain injury (TBI) is associated with an increased risk of late neurodegenerative complications via unknown mechanisms. Circulating neurotoxic 5-hydroxytryptamine 2A receptor (5-HT2AR) autoantibodies were reported to increase in subsets of obese type 2 diabetes having microvascular complications. It was tested whether autoantibodies (e.g., 5-HT2AR) increase in adults following traumatic brain injury in association with neurodegenerative complications.

Methods: Plasma from thirty-five middle-aged and older adult veterans (mean 65 years old) who had suffered traumatic brain injury was subjected to protein-A affinity chromatography. The resulting immunoglobulin (Ig) G fraction was tested for neurotoxicity (acute neurite retraction, and accelerated cell death) in mouse N2A neuroblastoma cells or for binding to a linear synthetic peptide (e.g., SEQ ID NO: 1) corresponding to the second extracellular loop region of the human 5-HT2A receptor.

Results: Nearly two-thirds of traumatic brain injured-patients harbored 5-HT2AR autoantibodies in their circulation. Active autoantibodies (e.g., 5-HT2A receptor autoantibodies) from TBI patients caused neurite retraction in mouse N2A neuroblastoma cells and accelerated N2A cell loss which was substantially prevented by co-incubation with a two hundred and fifty nanomolar concentration of M100907, a highly selective 5-HT2AR antagonist. Antagonists of RhoA/Rho kinase and Gq11/phospholipase C/inositol triphosphate receptor signaling pathways blocked (5-HT2A receptor) autoantibody-induced neurite retraction from TBI patients. Following traumatic brain injury, autoantibody (e.g., 5-HT2A receptor) binding to a 5-HT2A receptor peptide (e.g., SEQ ID NO: 1) was significantly increased in patients having co-morbid Parkinson's disease (n=3), dementia (n=5), and painful neuropathy (n=8) compared to TBI subsets without neurologic or microvascular complication (n=20). Autoantibody (e.g., 5-HT2A receptor) titer was significantly elevated in TBI subsets experiencing multiple neurotraumatic exposures vs. single TBI. Plasma white blood cell, a marker of systemic inflammation, correlated significantly (correlation coefficient r=0.52; P<0.01) with 5-HT2A receptor peptide binding of the TBI-autoantibody (5-HT2A receptor autoantibody).

Conclusion: These data suggest that circulating neurotoxic 5-hydroxytryptamine 2A receptor agonist autoantibodies increase in adults following traumatic brain injury in association with late neurodegenerative complications.

Introduction. Type 2 diabetes and traumatic brain injury (TBI) are associated with an increased risk of late-onset neurodegeneration (Walker K R, Tesco G. *Frontiers in Aging Neuroscience.* 2013; 5:29; Crane P K, et al. *JAMA Neurol.* 2016 Sep. 1; 73(9):1062-9; and Hu G, et al., *Diabetes Care.* 2007; 30(4):842-847) via mechanisms involving increased peripheral and central inflammation, respectively. Visceral obesity-associated inflammation promotes activation of innate and adaptive immune mechanisms (Patel P S, et al. *J Obes.* 2013; 2013:616193). In older adult type 2 diabetic subsets having Parkinson's disease or dementia, circulating plasma immunoglobulin G (IgG) autoantibodies bound to the 5-hydroxytryptamine 2A receptor and mediated neurotoxicity in mouse neuroblastoma cells through activation of Gq11/inositol triphosphate receptor (IP3R)/Ca2+ and RhoA/Rho kinase signaling pathways (Zimering M B, *J Endocrinol Diabetes.* 2018; 5(2)). Diffuse microvascular injury is an additional risk factor associated with the development of potent βendothelial, and neurotoxic IgG autoantibodies in subsets of long-standing, poorly controlled type 2 diabetes (Zimering M B, et al., *Diabetes Res Clin Pract.* 2011; 93(1):95-105; Zimering M B, et al., Metabolism. 2009; 58(6):882-7; and Zimering M B, et al., J Clin Endocrinol Metab. 2009; 94(6):2171-7).

Since long-term recovery following traumatic brain injury depends (in part) on normal angiogenesis and restoration of blood brain barrier function, it was tested whether circulating agonist 5-HT2AR autoantibodies increase in middle-aged and older adult veterans following traumatic brain injury and for possible association(s) between 5-HT2AR autoantibodies and neurodegenerative complications, or microvascular injury occurring in type 2 diabetes mellitus.

The 5HT2A receptor is highly concentrated in brain regions underlying cognition, memory, perception, and mood regulation (Xu T et al., *Brain Res Bull.* 2000; 51(6): 499-505). Increased circulating 5-HT2AR IgG (5-HT2A receptor) autoantibodies in traumatic brain injury might provide a biomarker (or be involved in the pathophysiology) of the later occurrence of neurodegenerative complications.

Participants and Methods. Patients. Thirty-five patients suffering prior traumatic brain injury (twenty-four with and eleven without co-morbid type 2 diabetes mellitus) were consecutively enrolled from the Endocrinology and Diabetes clinic of the Veterans Affairs New Jersey Healthcare System (VANJHCS) at Lyons and East Orange, New Jersey. Consent was obtained prior to blood drawing. For the comparison in FIG. 3B, data in a previously reported cohort of forty-seven patients having type 2 diabetes mellitus but lacking TBI exposure were used to test for possible association between 5-HT2A receptor autoantibody binding and systemic inflammation.

Blood drawing. Blood was drawn in the morning after an overnight fast. Plasma or serum was either immediately subjected to protein-A affinity chromatography (to obtain the immunoglobulin G fraction) or was stored at −40° C. for later use.

Protein-A affinity chromatography. Protein-A chromatography was carried out (Zimering M B, *J Endocrinol Diab.* 2017; 4(4):1-10). Protein-A eluate fractions were stored at 0-4 C.

Acute neurite retraction. Mouse N2A neuroblastoma cells were maintained in Dulbecco's minimal essential medium with 10% fetal calf serum. Neurite retraction assay was carried out (Zimering M B, *J Endocrinol Diab.* 2017; 4(4):1-10). Neurite retraction represents average neurite length-shortening after five minutes exposure to TBI (5-HT2A receptor) autoantibodies (60-100 nM) in the presence or absence of various G-protein coupled receptor (GPCR) or signaling pathway antagonists.

Mouse neuroblastoma cell loss. N2A cell loss was quantified using an MTT (3-(4,5-dimethylthiazol-2-yl)-2,5-diphenyltetrazolium bromide) tetrazolium reduction assay after overnight incubation with autoantibodies from TBI patients (Zimering M B, *Endocrinol Diabetes Metab J.* 2019 August; 3(4) pii: 118. Epub 2019 Aug. 14).

Serotonin 2A receptor peptide. An 18-meric, linear synthetic peptide (QDDSK . . . N) (SEQ ID NO: 1) having an amino acid sequence corresponding to the second extracellular loop region of the human 5-HT2A receptor was synthesized at Lifetein, Inc., catalog number 701781, and had 96.65% purity.

5-HT2A receptor peptide enzyme linked immunosorbent assay ELISA. A 60 micrograms per milliliter concentration of the 18-meric synthetic peptide (QDDSK . . . N) (SEQ ID NO: 1) was use as the solid-phase antigen in an enzyme-linked immunoabsorbent assay (ELISA) performed (Zimering M B, *Endocrinol Diabetes Metab J.* 2019 August; 3(4) pii: 118. Epub 2019 Aug. 14).

Pheochromocytoma (PC12)-cell derived heparan sulfate proteoglycan ELISA. An ELISA using immobilized rat PC-12 cell derived, purified heparan sulfate proteoglycan (HSPG) as the solid-phase antigen was carried out (Zimering M B, et al., *Diabetes Res Clin Pract.* 2011; 93(1):95-105). Strongly anionic PC-12 cell-derived HSPG was purified from conditioned medium using diethylaminoethyl (DEAE)-cellulose chromatography (Zimering M B, et al., *Diabetes Res* Clin Pract. 2011; 93(1):95-105).

Chemicals. Y27632, U73122, spiperone, M100907, ketanserin, bosentan, losartan, prazosin were obtained from Sigma, Inc., (St. Louis, Mo.). YM254890 was obtained from Focus Biomolecules, (Plymouth Meeting, Pa.). The other chemicals were research grade.

Protein concentration. Protein concentration was determined using a bicinchoninic assay kit (Thermo Fischer, Inc,) (Zimering M B, et al., *Diabetes Res Clin Pract.* 2011; 93(1):95-105).

Figure 2:
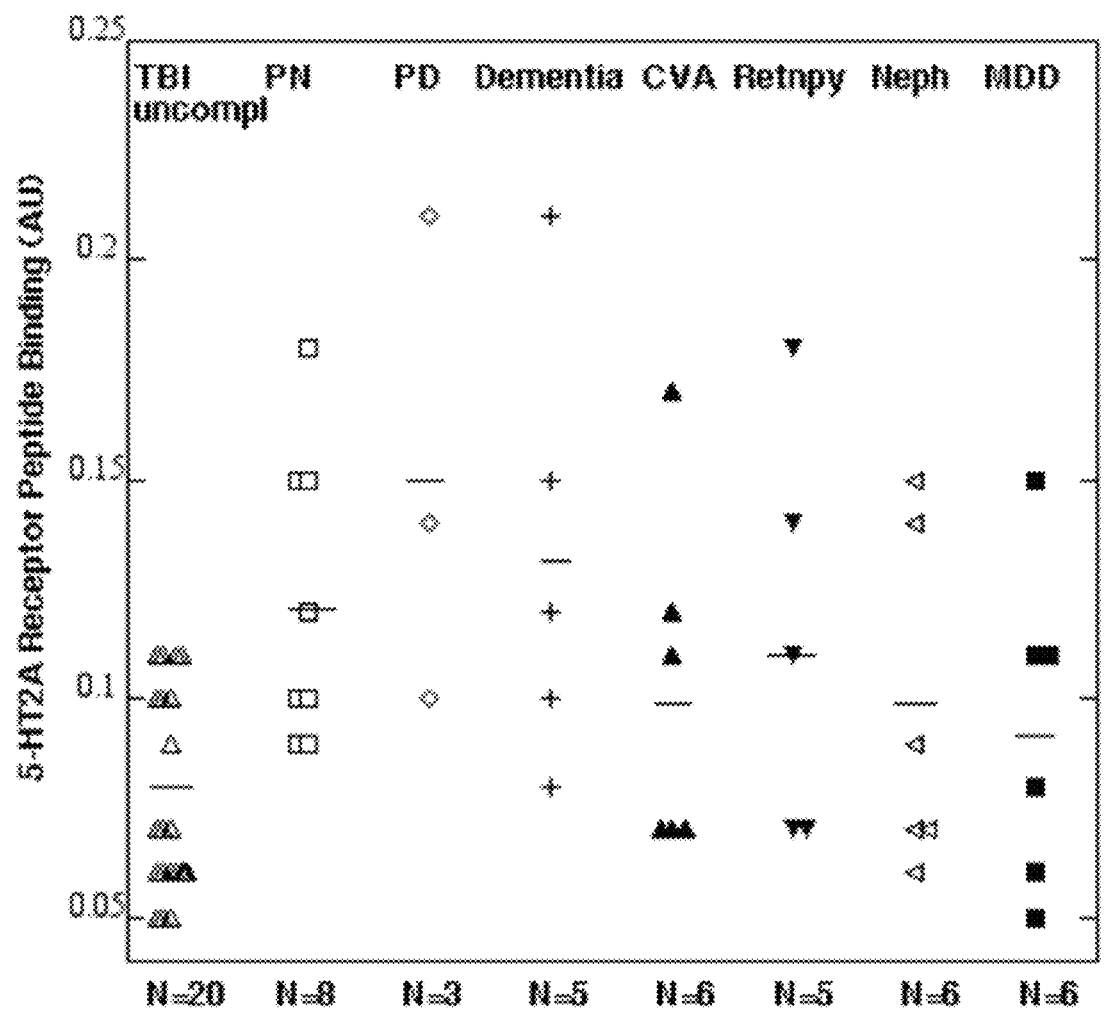
FIG. 2 shows the results of an enzyme-linked immunoassay using 5-HT2A receptor second extracellular loop region linear synthetic 18-mer (SEQ ID NO: 1); mean binding (indicated by horizontal lines) was significantly increased in 5-HT2A receptor autoantibodies ($\frac{1}{40}^{th}$ dilution) from TBI patients having co-morbid painful neuropathy (PN), Parkinson's disease (PD), dementia and diabetic retinopathy (Retnpy) compared to twenty TBI patients who lacked neurologic, neuropsychiatric or diabetic microvascular complication (TBI uncompl). One non-diabetic TBI patient with highest binding had both Parkinson's disease and dementia. CVA-cerebrovascular accident, Retnpy-diabetic retinopathy, Neph(ropathy), MDD-major depressive disorder; Total N exceeds thirty-five because many of the same patients had more than one co-morbidity, e.g., dementia and retinopathy, and painful neuropathy and nephropathy.

Statistics. Data are mean±SD (Table 15) or mean±SEM (FIG. 2). Comparisons are with Student's t-test with a significance level of P=0.05 for continuous variables, Pearson's correlation coefficient; or with Fischer's exact test for dichotomous variables.

Results. Baseline Clinical Characteristics in the Study Patients. The baseline clinical characteristics in the study patients is shown in Table 15. Twenty-four of thirty-five adult TBI patients (69%) had co-morbid type 2 diabetes mellitus (Table 16). Mean (5-HT2A receptor) autoantibody binding to the 5-HT2AR synthetic peptide (SEQ ID NO: 1) was two-fold higher than background level in the 35 TBI patients tested (0.10±0.05). Mean 5-HT2AR peptide binding of the (5-HT2A receptor) autoantibody among TBI patients with co-morbid type 2 diabetes mellitus was slightly higher (0.10±0.03 n=24 vs. 0.09±0.04; n=11; P=0.11) than in TBI without type 2 diabetes mellitus, but the difference was not statistically significant. An older man without type 2 diabetes mellitus who experienced TBI, and subsequently developed Parkinson's disease and dementia had (5-HT2A receptor) autoantibodies which displayed the highest level of 5-HT2AR peptide binding (0.21 AU, FIG. 2). This finding is consistent with a prior report that neurodegenerative disease was associated with substantially increased 5-HT2A receptor peptide binding in 5-HT2A receptor autoantibodies from patients with or without co-morbid type 2 diabetes mellitus (Zimering M B, *Endocrinol Diabetes Metab J.* 2019 August; 3(4) pii: 118. Epub 2019 Aug. 14).

TABLE 15

Baseline clinical characteristics in adult TBI patients TBI (n = 35)

| Risk factor | Mean (SD) |
|---|---|
| Age (years) | 65.2 ± 8.6 |
| BMI (kg/m$^2$) | 31.1 ± 6.1 |

TABLE 15-continued

Baseline clinical characteristics in adult TBI patients TBI (n = 35)

| Risk factor | Mean (SD) |
|---|---|
| HbA1c (%) | 8.6 ± 1.6 [24] |

BMI- body mass index;
Hba1c- glycosylated hemoglobin
[ ]- number of patients having co-morbid type 2 diabetes mellitus

TABLE 16

Baseline prevalence of angiopathic and neurologic complications in TBI patients

TBI (n = 35)

| | Diabetes (N = 24) | | No Diabetes (N = 11) | |
|---|---|---|---|---|
| Angiopathic complication | (N) | % | (N) | % |
| Diabetic Retinopathy | 5 | 14 | 0 | 0 |
| Diabetic Nephropathy | 6 | 17 | 0 | 0 |
| Painful neuropathy | 7 | 20 | 1 | 9 |
| Two or more angiopathies | 7 | 20 | 0 | 0 |
| Neurologic complication | | | | |
| Parkinson's disease | 2 | 6 | 1 | 9 |
| Dementia | 4 | 11 | 1 | 9 |
| Cerebrovascular accident | 5 | 14 | 1 | 0 |
| Neuropsychiatric complication | | | | |
| Major depressive disorder | 5 | 14 | 1 | 9 |
| No angiopathy | 12 | 34 | 10 | 29 |
| Uncomplicated TBI* | 10 | 29 | 10 | 29 |

*excluding patients with co-morbid major depressive disorder

Association between autoantibodies from TBI patients and 5-HT2AR peptide binding and baseline characteristics. Nearly two-thirds (22/35) of TBI patients demonstrated baseline presence of plasma 5-HT2A receptor autoantibodies (FIG. 2), defined as receptor peptide binding 1.5-fold or greater, i.e. ≥0.075 AU, than background (0.05 AU). Patient age, body mass index, or glycosylated hemoglobin was not significantly correlated with autoantibody 5-HT2AR peptide binding in each of the thirty-five TBI patients tested consistent with a prior report in 56 patients without TBI (Zimering M B, *Endocrinol Diabetes Metab J.* 2019 August; 3(4) pii: 118. Epub 2019 Aug. 14). Significantly higher mean 5-HT2A receptor autoantibody binding (to the 5-HT2AR linear synthetic peptide, SEQ ID NO: 1) occurred in TBI subsets having painful neuropathy (mean 0.12; P<0.001; N=8), Parkinson's disease (mean 0.15; P<0.001; N=3) dementia (mean 0.13; P=0.002; N=5) or diabetic retinopathy (mean=0.11; P=0.02; N=5) (FIG. 2) vs. TBI lacking neurologic or microvascular complications (mean=0.0775; N=20). Mean 5-HT2A receptor autoantibody/5HT2AR peptide binding (1/40$^{th}$ dilution) was higher, but did not reach a statistically significant level of difference in TBI subsets having stroke (mean=0.10; P=0.07; N=6), nephropathy (N=6; P=0.14), or major depressive disorder (MDD, mean 0.09; P=0.21; N=6) compared to TBI patients without neurovascular complications (FIG. 2). Taken together, the data in the current and a prior study Zimering M B, *Endocrinol Diabetes Metab J.* 2019 August; 3(4) pii: 118. Epub 2019 Aug. 14) indicate that (5-HT2A receptor) autoantibody binding to a linear synthetic peptide (e.g., SEQ ID NO: 1) corresponding to the second extracellular loop of the 5-HT2A receptor was significantly increased in 17/20 (85%) of patients having Parkinson's disease, i.e., suggestive of a possible disease specific association.

Figure 3A:
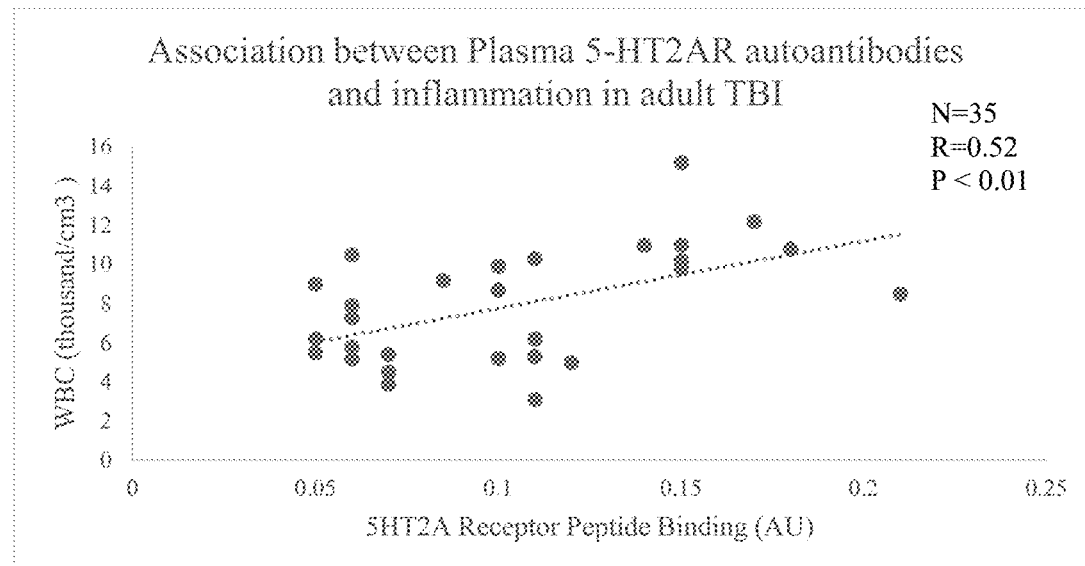
FIGS. 3A-B shows a correlation between white blood cell count and 5-HT2A receptor peptide binding to SEQ ID NO: 1 in the protein A eluates from 35 patients with TBI (FIG. 3A) 47 patients with type 2 diabetes and no TBI (FIG. 3B).
Figure 3B:
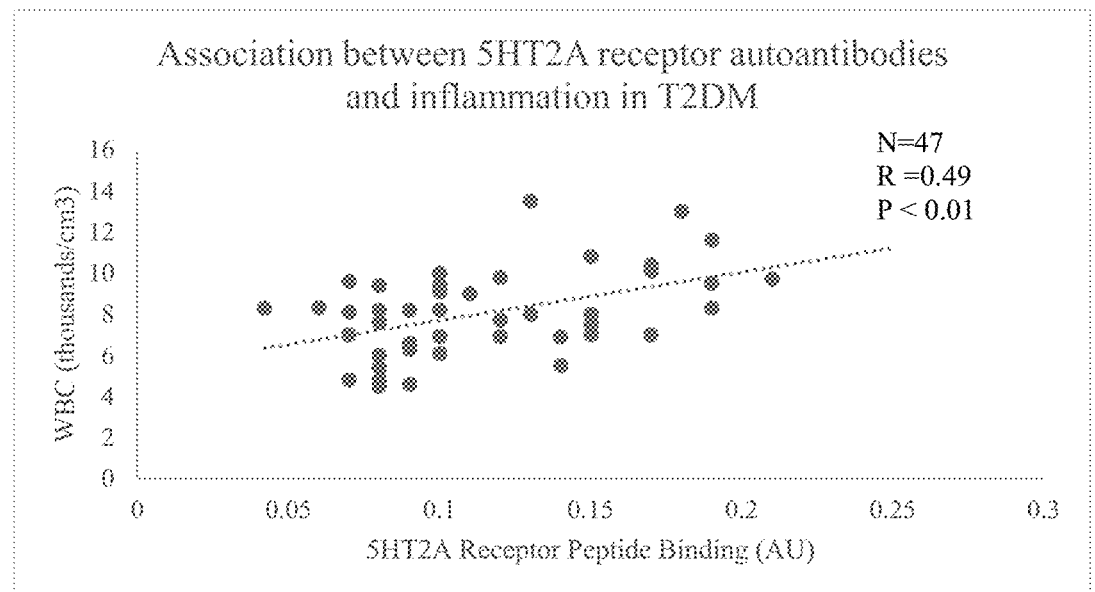

Association between 5-HT2AR peptide binding and systemic inflammation. An association between 5-HT2AR autoantibody binding and white blood cell count (WBC) was tested next, with the WBC serving as a marker of systemic peripheral inflammation which increases in a variety of chronic inflammatory conditions. There was a significant association (Pearson correlation coeff, R=0.52, N=35, P<0.01) between WBC and autoantibody ($1/40^{th}$ dilution) binding to the 5-HT2AR synthetic peptide from the thirty-five adult TBI patients (FIG. 3A). In an age-matched population of adult type 2 diabetes (n=47) without TBI (Zimering M B, *Endocrinol Diabetes Metab J*. 2019 August; 3(4) pii: 118. Epub 2019 Aug. 14) there was a significant association (Pearson correlation coeff R=0.49, P<0.01) between WBC and (5-HT2A receptor) autoantibody binding to the 5-HT2AR synthetic peptide (SEQ ID NO: 1) (FIG. 3B). Taken together, these data suggest systemic inflammation may contribute in part to the occurrence of 5-HT2AR autoantibodies in both TBI and non-TBI middle-aged and older adults, many of whom were affected by obese type 2 diabetes mellitus.

Pharmacologic specificity of 5-HT2AR autoantibody neurotoxicity in N2A cells. Long-lasting agonist 5-HT2A receptor autoantibodies in subsets of obese type 2 diabetes having major depressive disorder, Parkinson's disease, or dementia were previously reported to cause acute N2A neuroblastoma cell neurite retraction and accelerated N2A cell loss by a mechanism involving activation of the 5-HT2A receptor which is positively coupled to Gq11/IP3R/Ca2+ signaling pathway (Zimering M B, *J Endocrinol Diabetes*. 2018; 5(2); and Zimering M B, *J Endocrinol Diab*. 2017; 4(4):1-10). Therefore, the pharmacologic specificity of 5-HT2A receptor autoantibody-induced acute neurite retraction was tested using autoantibodies from TBI patients. The protein-A eluate fraction of adult TBI patient plasma caused dose-dependent acute neurite retraction in N2A cells. Acute neurite retraction was completely or nearly completed prevented by co-incubation with a 250-500 nanomolar concentration of the highly selective 5-HT2AR antagonist M100907 (Table 17). It was also substantially blocked by co-incubation with a potent, less selective 5-HT2AR antagonist (spiperone) or a less potent, but specific 5-HT2AR antagonist, ketanserin (Table 17). Substantially higher (micromolar) concentrations of a 5-HT2BR antagonist SB204741 had no significant protective effect on autoantibody-induced neurite retraction (Table 17). Higher concentration of several different Gq11-subclass, GPCR receptor antagonists (losartan, bosentan, prazosin) selective for the (angiotensin II, type 1, endothelin 1, or alpha1 adrenergic) receptor, respectively, had little or no significant protective effect on autoantibody-induced neurite retraction from autoantibodies from adult TBI patients (Table 17).

TABLE 17

Effect of GPCR antagonists on TBI 5-HT2A receptor autoantibody-induced acute neurite retraction

| Antagonist | Conc | GPCR | % of autoantibody Neurite Retraction from TBI patients |
|---|---|---|---|
| M100907 | 250 nM | 5-HT2A | 0% |
| Spiperone | 400 nM | 5-HT2A | 20% |

TABLE 17-continued

Effect of GPCR antagonists on TBI 5-HT2A receptor autoantibody-induced acute neurite retraction

| Antagonist | Conc | GPCR | % of autoantibody Neurite Retraction from TBI patients |
|---|---|---|---|
| Ketanserin | 1 µM | 5-HT2A | 26% |
| Ketanserin | 2 µM | 5-HT2A | 18% |
| Prazosin | 850 nM | A1-ADR | 100% |
| SB204741 | 1 µM | 5-HT2B | 70% |
| Losartan | 10 µM | Ang IIR | 80% |
| Bosentan | 10 µM | ET-1R | 80% |

A 60 nanomolar concentration of the IgG autoantibodies (e.g., 5-HT2A receptor autoantibodies) from a representative TBI patient was incubated with N2A cells in the presence or absence of the indicated concentration of the selective GPCR antagonist. Results are expressed as % of autoantibody-induced neurite length-shortening (using antibodies from a TBI patient) which varied by <15%. Similar results were observed in the 5-HT2A receptor autoantibodies from four different TBI patients.

Next, involvement of Gq11-coupled, downstream signaling pathway mediators in the mechanism of the 5-HT2A receptor autoantibody-induced acute N2A neurite retraction was tested using autoantibodies from TBI patients. In mouse neuroblastoma cells incubated with 5-HT2A receptor autoantibodies (60 nanomolar concentration) from adults TBI patients, the selective signaling pathway antagonists for Gq11 (YM254890), the inositol triphosphate receptor (2-APB) or phospholipase C (PLC) (U73122), afforded 89-100% protection against acute N2A neurite retraction (Table 18). Co-incubating N2A cells together with a 10 µM concentration of Y27632, a selective inhibitor of RhoA/Rho kinase (ROCK) signaling, provided near complete protection against 5-HT2A receptor autoantibody-induced acute neurite retraction (Table 18) using autoantibodies from TBI patients. Taken together, these data suggest autoantibody-induced neurite retraction activates RhoA/Rho kinase and Gq11/IP3R/Ca2+ signaling downstream of 5-HT2A receptor binding using autoantibodies from TBI patients is consistent with prior reports in 5-HT2A receptor autoantibodies from patients with neurodegenerative disorders, but lacking TBI (Zimering M B, *J Endocrinol Diabetes*. 2018; 5(2); and Zimering M B, *J Endocrinol Diab*. 2017; 4(4):1-10),

TABLE 18

Effect of GPCR and RhoA/Rho kinase signaling pathway antagonists on 5-HT2A receptor autoantibody-induced neurite retraction using autoantibodies from TBI patients

| Treatment | Conc | % of 5-HT2A receptor Autoantibody Neurite Retraction |
|---|---|---|
| TBI Auto-AB | 60 nM | 100% |
| YM 254890 | 1 µM | 11% |
| U73122 | 1 µM | 10% |
| Y27632 | 10 µM | 0% |
| 2-APB | 25 µM | 0% |

A 60 nanomolar concentration of 5-HT2A receptor autoantibodies from TBI patients was incubated with N2A cells in the presence or absence of the indicated concentration of Gq11/PLC-gamma/IP3R antagonist or RhoA/Rho kinase pathway inhibitor. Results are expressed as % inhibition of autoantibody-induced neurite length-shortening using autoantibodies from TBI patients which varied by <15%. Similar results were observed in 5-HT2A receptor autoantibodies from two TBI patients.

Figure 4A:
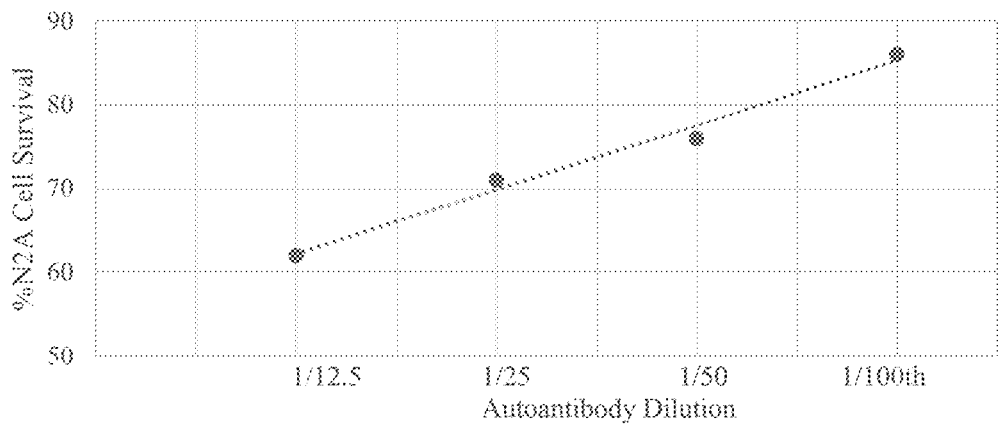
FIGS. 4A-B shows that TBI (5-HT2A receptor) autoantibodies cause a dose-dependent accelerated N2A cell loss that can be prevented by a specific 5HT2A receptor antagonist.
Figure 4B:
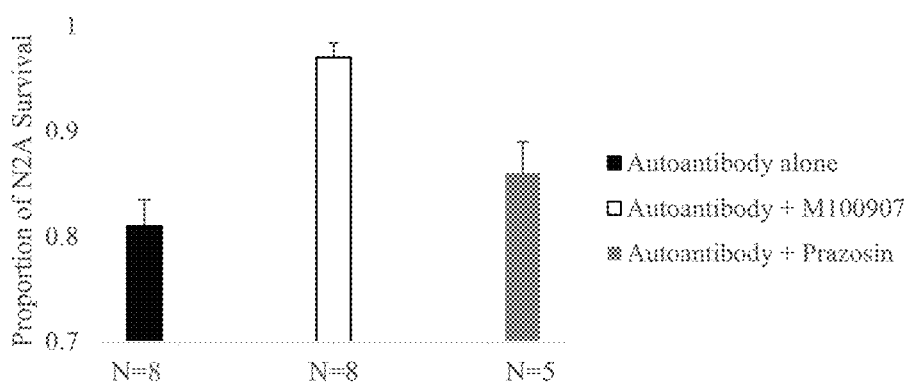

5-HT2A receptor autoantibodies from adult patients with TBI caused dose-dependent, accelerated N2A cell loss after 16-24 hours incubation (shown for a representative patient, FIG. 4A). In eight of eight TBI patients tested, accelerated cell death was nearly completely prevented by co-incubation with a 250 nanomolar concentration of the highly selective 5-HT2AR antagonist, M100907 (FIG. 4B). Co-incubation with a more than three-fold higher concentration (850 nM) of the selective alpha1 adrenergic receptor blocker prazosin had much less protective effect (n=5 patients tested, FIG. 5B). M100907 (250 nM-500 nM) had no significant effect alone on N2A cell survival (not shown in FIG. 4B).

Figure 5A:
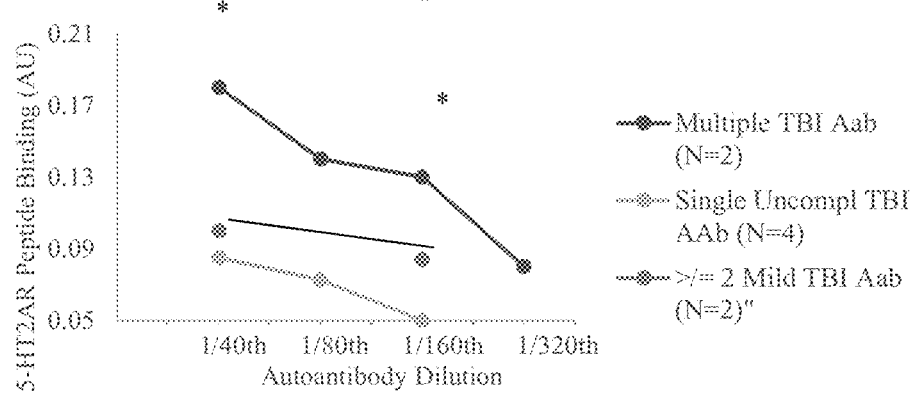
FIGS. 5A-B shows multiple TBI exposure is associated with increased 5-HT2A receptor autoantibody titer and 5-HT2AR peptide (SEQ ID NO: 1) binding potency compared to single uncomplicated TBI; *$P<0.01$; ab-autoantibody (5-HT2A receptor autoantibodies) (FIG. 5A).

Titer and potency of autoantibodies from TBI patients. Titer and potency of plasma 5-HT2AR agonist autoantibodies were significantly increased in patients who had experienced repetitive athletic neurotrauma (n=2 patients) or two-three TBI episodes (n=2 patients) compared to a single uncomplicated TBI episode (n=4 patients) (FIG. 4A). These data suggest a possible dose-response relationship between the 5-HT2AR autoantibodies and higher number of neurotraumatic episodes. Among four patients who had experienced repetitive or two-three TBI exposures, one patient suffered with Parkinson's disease (n=1) and three had mild neurocognitive disorder (n=3) (according to criterion established in the St Louis University Mental Status test (SLUMS)) (Tariq S H, et al., *Am J Geriatr Psychiatry*, 14(11):900-910). The four patients with a single prior TBI (i.e., uncomplicated TBI; FIG. 5A) were free of neurological sequelae or cognitive impairment.

Figure 5B:
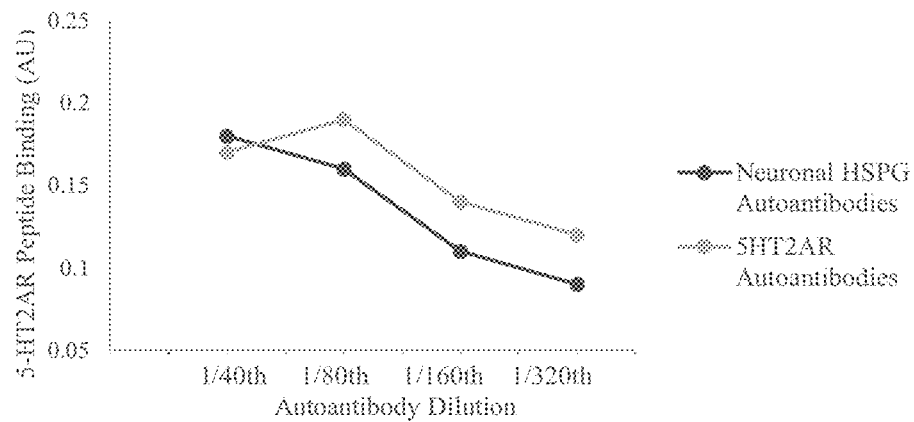

Newly-recognized dementia (by SLUMS testing) occurred in a 70-year old man with long-standing type 2 diabetes mellitus complicated by nephropathy, painful neuropathy, and retinopathy. The patient's autoantibodies not only displayed high titer, potent binding to the 5-HT2A receptor linear synthetic peptide (SEQ ID NO: 1) (FIG. 5B), but also similar (high-titer, high potency) binding to a neuronal-derived heparan sulfate proteoglycan purified from rat pheochromocytoma (PC12) cells (FIG. 5B).

Figure 6:
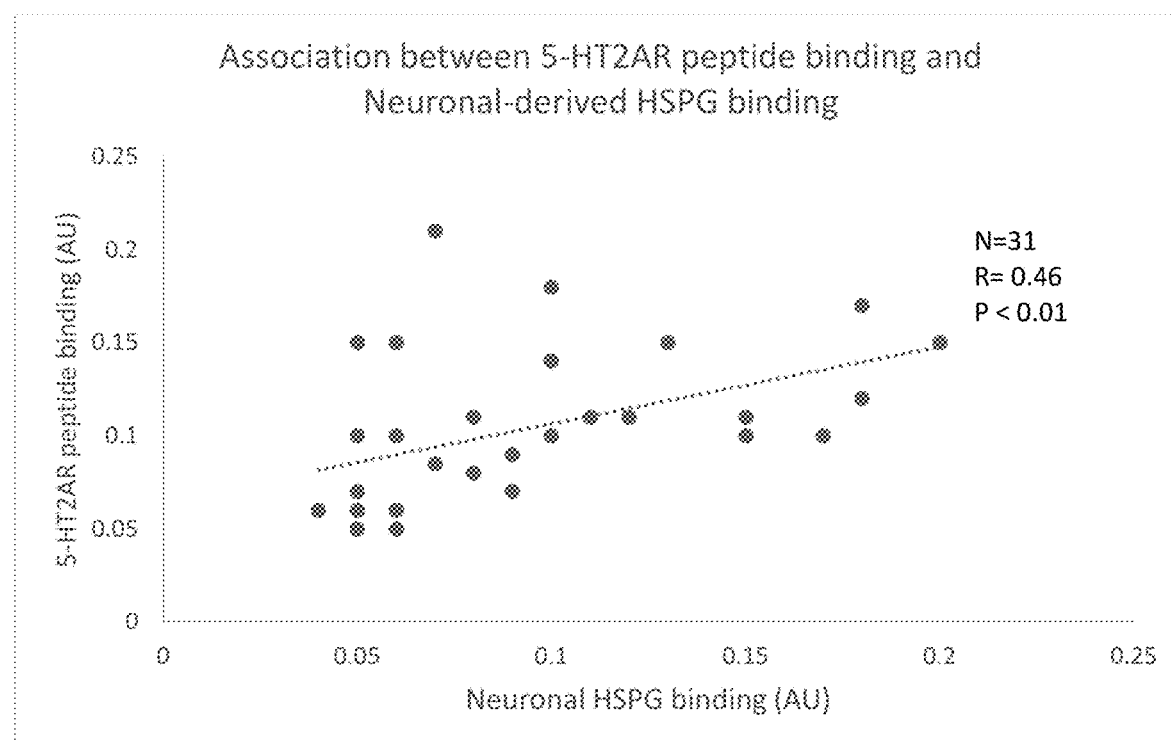
FIG. 6 shows a correlation between 5-HT2AR peptide (SEQ ID NO: 1) and neuronal HSPG binding in the protein-A eluates from thirty-one of thirty-five TBI patients.

The 5-HT2A receptor and heparan sulfate proteoglycan are both concentrated on the cell surface of neurons and vascular cells; both receptors have anionic regions important for ligand binding. In thirty-one of thirty-five adult TBI patients tested, 5-HT2A receptor autoantibody ($\frac{1}{40}^{th}$ dilution) binding to the 5-HT2AR second extracellular loop region peptide (SEQ ID NO: 1) was significantly correlated ($P<0.01$; $R=0.46$) with binding to purified PC12-derived HSPG (FIG. 6). These results suggest that autoantibodies from TBI patients may target (in part) strongly anionic sites present on both the 5-HT2AR and neuronal HSPG.

Discussion Late neurodegeneration increases substantially in middle-aged and older adults following TBI, however, the mechanism(s) are poorly understood and there is currently no biomarker to identify a high-risk subgroup (Walker K R et al., *Frontiers in Aging Neuroscience*. 2013; 5:29). The current data are the first to suggest that adult TBI is associated with a substantially increased prevalence of 5-HT2AR-targeting, agonist IgG autoantibodies (5-HT2A receptor autoantibodies). Neurotoxicity mediated by the 5-HT2A receptor autoantibodies was significantly modulated by selective antagonists of the 5-HT2AR and by inhibitors of Gq11/phospholipase C/inositol triphosphate receptor/Ca2+ signaling consistent with prior reports in subsets of older obese type 2 diabetes mellitus having Parkinson's disease and/or dementia, but lacking TBI (Zimering M B, *J Endocrinol Diabetes*. 2018; 5(2); and Zimering M B, *J Endocrinol Diab*. 2017; 4(4):1-10). Systemic inflammation occurs in both obese type 2 diabetes and following traumatic brain injury. The present data suggest a possible link between systemic inflammation and the development of 5-HT2AR autoantibodies. In a rodent model of systemic inflammation induced by injection of lipopolysaccharide (LPS), 5-HT2AR mediated (in part) the effect of interleukin-1 on body temperature (Voronova I P, et al., *Pharmacol Res*. 2016; 103:123-131).

Evidence that pools of 5-HT2A receptor autoantibodies from TBI patients can target both 5-HT2AR and neuronal HSPG, and HSPG is of interest since HSPG abundant in basement membranes promotes cell binding as well as contributes to blood: brain, blood: peripheral nerve, and blood: retinal barrier function. In prior reports in diabetic macular edema or painful neuropathy patients, autoantibodies which displayed high affinity for heparin and purified neuronal-derived HSPG (Zimering M B, et al., *Metabolism*. 2009; 58(6):882-7) caused contraction and apoptosis in endothelial cells via activation of RhoA/Rho kinase signaling (Zimering M B, et al., *J Clin Endocrinol Metab*. 2009; 94(6):2171-7). Endothelial cell barrier disruption by HSPG-targeting autoantibodies may have a role in promoting increased access of 5-HT2AR-targeting autoantibodies to receptor binding sites in the central nervous system. Heparan sulfate proteoglycan is elaborated from basement membranes in poorly-controlled diabetes (Vlodaysky I, et al., *Matrix Biol*. 2013 Jun. 24; 32(5):220-2) via the action of heparanase, an enzyme which cleaves HSPG side chains. Endothelial cell heparanase expression increases under pro-inflammatory conditions (Chen G, et al., *Biochemistry*. 2004 May 4; 43(17):4971-7) and HSPG is a known target of humoral immunity in subsets of systemic lupus erythematosus (Faaber P, et al. *J Clin Invest*. 1986 June; 77(6):1824-30). One possibility is that vascular remodeling following traumatic brain injury might cause targeting of neuronal HSPG (by the humoral immune system) especially in persons manifesting persistent inflammation and heightened adaptive immunity.

This study included middle-aged and older men recruited from diabetes and endocrinology clinics which might may led to an overestimation of the actual prevalence of 5-HT2AR-targeting autoantibodies since heightened inflammation which occurs in obese type 2 diabetes mellitus and thyroid autoimmunity are likely associated with diverse kinds of autoantibodies.

The 5-HT2AR is a druggable G-protein coupled receptor which is a known target for several FDA-approved medications useful in the treatment of diabetic painful neuropathy, major depression, schizophrenia, and Parkinson's disease-related hallucinations. 5HT2A receptor autoantibodies which bind to the 5-HT2AR receptor may be a useful biomarker in identifying a subset of TBI subjects at increased risk for late neurodegeneration.

Example 4: Serotonin 2A Receptor Autoantibodies in Diabetic Neurovascular Complications Neurovascular 5-hydroxytryptamine (serotonin) 2A receptor (5-HT2AR) autoantibodies were previously reported to function as long-acting agonists in diabetic angiopathy and subsets of major depression, Parkinson's disease or dementia. The 5-HT2A receptor is highly expressed in specific brain regions underlying cognition, perception and mood regulation. Long-lasting 5-HT2A receptor activation by circulating autoantibodies might contribute to pathophysiology via central and peripheral mechanisms. Since the risk or incidence of Parkinson's disease, depression and dementia increase following traumatic brain injury (TBI), circulating neurotoxic autoantibodies (e.g., 5HT2AR) were tested, characterized and compared with autoantibodies from TBI patients vs. diabetic subsets with or without neurodegenerative disorders. Plasma IgG autoantibodies (e.g., 5-HT2AR autoantibodies) were obtained by protein-A affinity chromatography in ten male TBI patients mean age 64 years old. A 2-6 mg/mL concentration was tested for binding to an 18-meric linear synthetic peptide having an amino acid sequence corresponding to the second extracellular loop region of the human 5-HT2A receptor (e.g., SEQ ID NO: 1). Results were compared to those in thirty-six, age-matched men (thirty-one with, five without type 2 diabetes) having Parkinson's disease (PD) (n=17), major depressive disorder (MDD) (n=12) or dementia (n=7). Mean 5-HT2A receptor peptide binding in (5-HT2AR) autoantibodies from TBI (0.12±0.02 AU; n=10) and PD, MDD or dementia (0.13±0.01 AU; n=36) was significantly increased (P<0.01) compared to the mean level in six age-matched diabetic patients (0.07±0.01) without angiopathy or neurodegenerative disorder. Higher titer of 5-HT2A receptor peptide binding autoantibodies was observed in TBI with dementia or TBI with Parkinson's disease (n=2, half-maximal binding~1 mg/mL) compared to TBI without neurodegenerative complications (n=4, half-maximal binding 3.5 µg/mL) consistent with results in diabetic subsets with and without dementia or PD. Autoantibody-induced acute N2A mouse neuroblastoma neurite retraction (after 5 minutes incubation with 2-3 µg/mL concentration) correlated significantly with 5-HT2A receptor peptide binding in twenty-five patients tested. Mean neurite retraction in TBI patient 5-HT2AR autoantibodies (52±10%, n=10) was substantially prevented (89-91%) by co-incubation with 200-670 nM concentrations of the highly selective 5HT2AR antagonist M100907. It was also significantly blocked by co-incubation with each of 10 µM Y27632 (Rho kinase inhibitor), 1 µM YM25489 (Gq11 antagonist), 1 µM U73122 (PLC inhibitor), and 50 µM 2-APB (IP3R inhibitor).

These results suggest that a subset of older adults with traumatic brain injury harbored circulating neurotoxic autoantibodies (e.g., 5-HT2AR autoantibodies) which bound to a second extracellular loop region peptide (SEQ ID NO: 1) of the human 5-HT2A receptor. The second extracellular loop which lies in close proximity to the receptor orthosteric binding pocket normally prevents constitutive receptor activation. 5-HT2AR autoantibodies which target the second extracellular loop may cause persistent serotonin 2A receptor activation which via positive coupling to RhoA/Rho kinase and Gq11/PLC/IP3R signaling mediates long-lasting neurotoxicity.

Example 5: Schizophrenia Plasma Autoantibodies Promote 'Biased Agonism' at the 5-Hydroxytryptamine 2A Receptor: Neurotoxicity is Positively Modulated by Metabotropic Glutamate 2/3 Receptor Agonism Abstract. Aims: To test whether neurite-inhibitory plasma autoantibodies in chronic schizophrenia activate Gq/11- and Gi-coupled signaling pathways downstream of 5-hydroxytryptamine 2A receptor activation; and for modulation of serotonergic signaling by the metabotropic glutamate 2/3 receptor (mGlu2/3R) agonist LY379268.

Methods: Plasma from five older adults with chronic schizophrenia and eight age-matched patients having another neuropsychiatric, immune or metabolic disorder was subjected to Protein-A affinity chromatography to obtain IgG autoantibodies. Mean neurite retraction (5 minutes) or cell survival (24 hours) was determined in mouse N2A neuroblastoma cells incubated with autoantibodies in the presence or absence of specific antagonists of the Gq/11/PLC/IP3R signaling pathway, Gi-coupled, beta-arrestin2-directed pathways, or LY379268.

Results: Chronic schizophrenia plasma 5-HT2A receptor autoantibodies-mediated dose- and time-dependent acute N2A neurite retraction was completely prevented by M100907, a selective 5-hydroxytryptamine 2A receptor antagonist. LY379268 promoted 5-HT2A receptor autoantibody-induced neurite retraction causing a shift-to-the-left in the dose-response curve. Antagonists of the RhoA/Rho kinase and Gq/11/PLC/IP3R signaling pathways blocked autoantibody-mediated neurite retraction. Chronic schizophrenia plasma 5-HT2A receptor autoantibodies mediated increased N2A cell survival which was blocked by LY379268, pertussis toxin, and antagonists of PI3-kinase-mediated survival signaling.

Conclusion: Schizophrenia plasma 5-HT2A receptor autoantibodies activate the 5-hydroxytryptamine 2A receptor positively coupled to Gq/11/PLC/IP3R pathway and RhoA/Rho kinase signaling activation in promoting acute N2A cell neurite retraction. Autoantibodies in a subset of patients experiencing hallucinations promoted increased N2A cell survival mediated (in part) via a pertussis-toxin sensitive, Gi-coupled, PI3-kinase-dependent mechanism. Positive modulation of 5-HT2AR-mediated neurite retraction by LY379268 suggests the autoantibodies may target (in part) the 5-hydroxytryptamine 2A receptor/metabotropic glutamate 2/3 receptor (5-HT2AR/mGlu2R) heteromer.

Introduction. The serotonin 2A receptor (5-HT2AR) is highly expressed in cortical brain regions underlying normal perception (Xu T, Pandey S C. *Brain Res Bull.* 2000; 51(6):499-505). The hallucinogenic drug lysergic acid diethylamine (LSD) causes long-lasting 5-HT2AR activation which is positively coupled to Gq/11- and β-arrestin-2-dependent signaling pathway activation (Wacker D, et al., *Cell.* 2017; 168(3):377-389). Head twitch in mice infused with the hallucinogenic (reversible 5HT2AR agonist) 1-[2, 5-dimethoxy-4-iodophenyl]-2-aminopropane (DOI) required an additional contribution from metabotropic glutamate (mGlu)2R-mediated, Gi-coupled signaling since head twitch was not observed in DOI-treated mice harboring an mGlu2R knock-out mutation (Moreno, J L, et al., *Neurosci Lett* 2011, 493(3): 76-79). Heteromeric 5-HT2AR/mGlu2R complexes occur in the mammalian prefrontal cortex (González-Maeso J, et al., *Nature.* 2008; 452(7183):93-97) and are thought to integrate serotonergic and glutamatergic signals via allosteric receptor-receptor interactions alters the balance between Gq11- and Gi-coupled signaling pathway activation (González-Maeso J, et al., *Nature.* 2008; 452(7183):93-97).

Paranoid schizophrenia is a common disabling disease affecting ~1% of adults (Huang A, et al., *J Med Econ.* 2018 October; 21(10):1026-1035). Evidence from epidemiologic studies (Benros M E, et al., *Annals of the New York Academy of Sciences.* 2012; 1262:56-66) and a recent genome-wide association study (Schizophrenia Working Group of the Psychiatric Genomics Consortium. Biological insights from 108 schizophrenia-associated genetic loci. *Nature.* 2014 Jul. 24; 511(7510):421-7) suggests a role for dysregulated acquired immunity in the pathophysiology of schizophrenia.

A possible role for brain reactive autoantibodies was suggested by prior studies (Benros M E, et al., *Annals of the New York Academy of Sciences*. 2012; 1262:56-66) including a report that plasma IgG autoantibodies in a subset of chronic schizophrenia potently suppressed neurite outgrowth and mediated strong depolarization in N2A mouse neuroblastoma cells (Zimering M B, et al., *J Endocrinol Diab*. 2016; 3(1):1-14). Since major depression and Parkinson's disease autoantibodies mediated long-lasting 5-HT2A receptor activation positively coupled to Gq/11 signaling (Zimering M B., *J Endocrinol Diab*. 2017; 4(4):1-10; and Zimering M B., *J Endocrinol Diabetes*. 2018; 5(2): 10), it was tested whether plasma autoantibodies from chronic paranoid schizophrenia patients activate the 5-HT2A receptor, and whether Gq/11-mediated signaling leads to neurite outgrowth inhibition in N2A mouse neuroblastoma cells. A role for signaling cross-talk involving 5-HT2AR/mGlu2R heteromers was tested by comparing N2A acute neurite retraction induced by plasma autoantibodies from patients with schizophrenia in the presence or absence of the mGlu2/3R agonist LY379268. Since LY379268 was previously reported to suppress hallucinogen-induced Gi-coupled signaling at the 5HT2AR (Gonzalez-Maeso J, et al., *Nature*. 2008; 452(7183):93-97), biased 5-HT2AR-dependent, Gi-coupled signaling evoked by autoantibodies was investigated from subgroups of psychosis-prone vs. patients not experiencing recurrent visual or auditory hallucinations.

Participants and Methods. Participants. Outpatient men ranging in age from 47-78 years old were consecutively enrolled from the diabetes and endocrinology clinics at the Veterans Affairs New Jersey Health Care System (East Orange and Lyons, New Jersey).

Psychosis prone patients. Patient 1: A 61-year-old man with a history of chronic paranoid schizophrenia and multiple recurrent hospitalizations for auditory hallucinations and one previous suicide attempt. The patient has type 2 diabetes mellitus of approximately eight years duration without microvascular complications. Patient 2: A 55-year-old man with chronic paranoid schizophrenia, three previous suicide attempts, and type 2 diabetes (of five years known duration) without microvascular complications. Patient 3: A 61-year-old man having major depressive disorder with mood-incongruent psychotic features and type 2 diabetes of fourteen years duration. Patient 4: A 47-year-old man with chronic schizophrenia, and no history of type 2 diabetes. He had paranoid delusions without any suicide attempt.

Blood samples: Blood was drawn in the morning after an overnight fast. Plasma or serum was stored at −20° C.

Protein A affinity chromatography—Protein-A affinity was performed (Zimering M B, *J Endocrinol Diabetes*. 2018; 5(2): 10).

N2A mouse neuroblastoma cells. N2A mouse neuroblastoma cells were cultured in Dulbecco's modified Eagles medium (DMEM) containing 10% fetal calf serum. Cells were fed with fresh medium every 1-2 days, except for survival assays in which fresh medium was not added for up to 5 days prior to the addition of test autoantibody fractions.

Acute neurite retraction assay. Percent of basal neurite length in N2A cells expressing one or more proximally-located dendrite-like process was determined after interval exposure to test substances (Zimering M B, *J Endocrinol Diabetes*. 2018; 5(2): 10).

N2A cell survival. MTT assay was performed 24 hours after incubation with test substances (Zimering M B, *J Endocrinol Diabetes*. 2018; 5(2): 10).

Chemicals. Chemicals were obtained from Sigma, Co., Inc. (St Louis, Mo.), except YM-254890 (Focus Biomolecules) and LY 379268 (Tocris Bioscience).

Protein assay. Protein concentration was determined using a modified bichichonic acid assay (Bio Rad. Inc.).

Statistics. Paired and unpaired T-tests were used to assess for statistically significant differences between groups or between treatments.

Results. Baseline characteristics in the study patients. The clinical characteristics in the study patients are shown in Table 19. Patients having chronic schizophrenia did not differ significantly in their mean age, body mass index or glycosylated hemoglobin level from patients having Parkinson's disease (n=5), dementia (n=1), or diabetic nephropathy (n=1).

TABLE 19

Clinical characteristics in the study participants

| Diagnosis | Age (years) | HbA$_1$c (%) | BMI (kg/m$^2$) |
|---|---|---|---|
| Schizophrenia (n = 5) | 61.4 ± 9.7 | 7.0 ± 1.1 | 31.7 ± 8.1 |
| PD or Other (n = 7) | 70.6 ± 5.5 | 7.2 ± 1.4 | 33.1 ± 6.2 |
| Diabetes without MVD (n = 2) | 77.5 ± 6.1 | 7.2 ± 0.2 | 33.5 ± 5.3 |

*Parkinson's disease (PD)(n = 4),
major depressive disorder (n = 1),
diabetic nephropathy (n = 1),
dementia (n = 1).
MVD- microvascular disease.

Figure 7A:
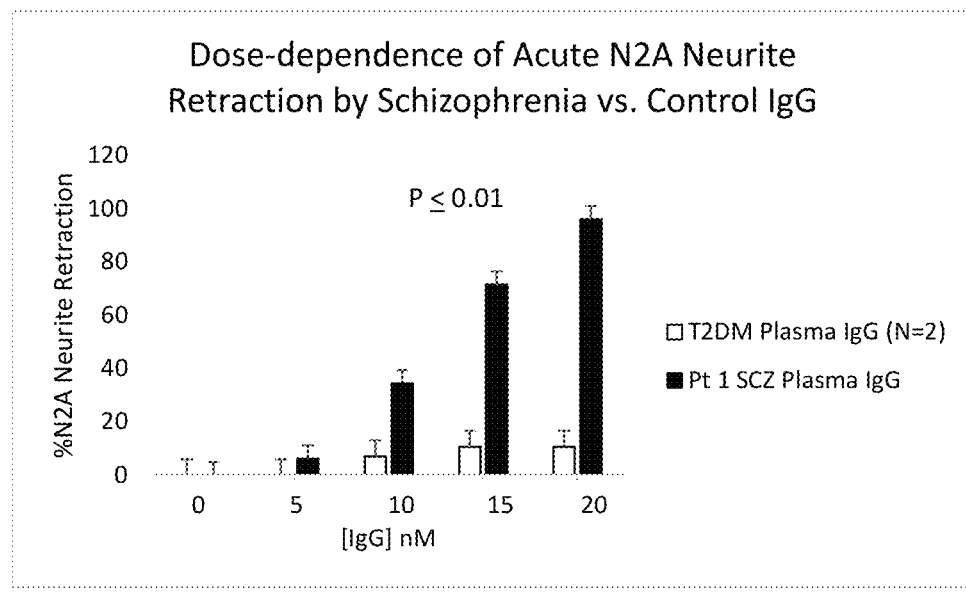
FIGS. 7A-B shows the results of acute neurite retraction induced by diabetic schizophrenia plasma autoantibodies.
Figure 7B:
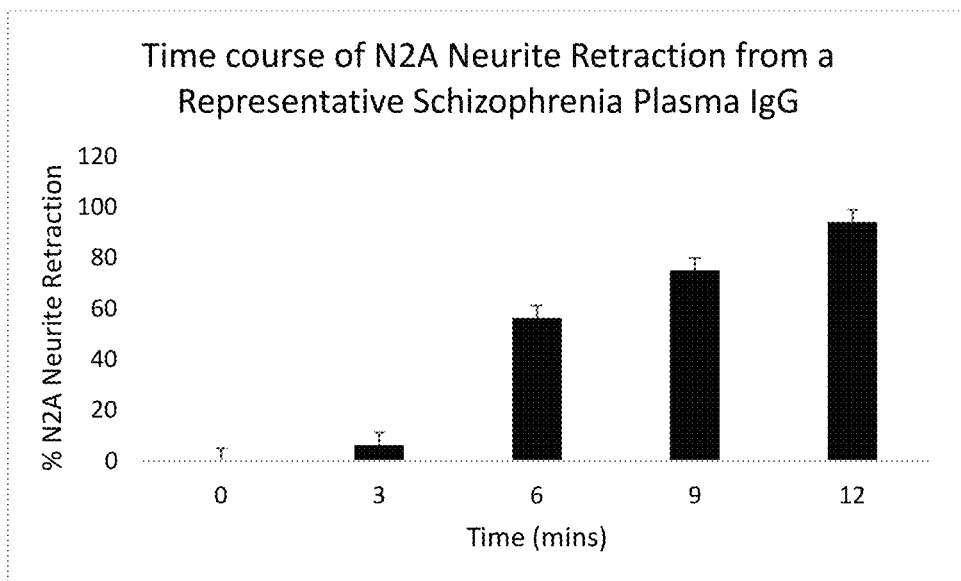

Acute N2A neurite retraction from plasma IgG fractions obtained from patients with schizophrenia. Plasma autoantibodies (at IgG concentrations≥10 nM) from patients with schizophrenia caused dose-dependent N2A neurite retraction which significantly exceeded neurite retraction in an identical concentration of IgG autoantibodies from two older adult type 2 diabetes patients without microvascular, neuropsychiatric or neurodegenerative complications (FIG. 7A). Neurite retraction in response to potent plasma autoantibodies from a schizophrenia patient, e.g. Pt 1, was linear, irreversible and more than 50% neurite withdrawal occurred after 5 minutes' exposure time (FIG. 7B).

Plasma autoantibody-induced neurite retraction using autoantibodies from patients with schizophrenia (SCZ) was completely prevented by co-incubation with a two-hundred nanomolar concentration of the selective 5HT2A receptor antagonist, M100907 (Table 20). Slightly higher concentrations (500 nM) of the 5-HT2A receptor antagonists, spiperone and ketanserin, afforded significant protection (~50-80%) against plasma (5-HT2A receptor) autoantibody-induced neurite retraction (Table 20) using autoantibodies from SCZ patients. A higher concentration (1-10 µM) of selective antagonists of the endothelin A, angiotensin type 1, alpha-1-adrenergic and 5HT2B receptors (Gq/11-coupled GPCRs) i.e., bosentan, losartan, prazosin and SB204741, did not significantly protect (0-28%) against autoantibody IgG-induced neurite retraction (Table 20) using autoantibodies from patients with SCZ.

TABLE 20

Pharmacology of autoantibody (AutoAB)-
induced neurite retraction from
schizophrenia patients

| Antagonist + AutoAB (20 nM) [Concentration] | | Receptor | % AutoAB-induced neurite retraction |
|---|---|---|---|
| M100907 | 200 nM | 5HT2AR | 0 ± 0% |
| Spiperone | 500 nM | 5HT2AR | 17 ± 6% |
| Ketanserin | 500 nM | 5HT2AR | 43 ± 11% |
| SB204741 | 1 μM | 5HT2BR | 100 ± 0% |
| Bosentan | 10 μM | ETAR | 94 ± 7% |
| Losartan | 10 μM | AT1R | 72 ± 8% |
| Prazosin | 1 μM | A1AR | 72 ± 10% |

A twenty nanomolar concentration of protein-A eluate fraction of plasma from Pt 1 with schizophrenia was incubated with N2A cells in the presence or absence of the indicated concentration of each Gq/11, GPCR antagonist. Results are the mean+/−SD of two experiments.

Mechanism of plasma autoantibodies (IgG)-induced neurite retraction using autoantibodies from patients with schizophrenia. Plasma IgG autoantibodies from patients with major depressive disorder and Parkinson's disease were previously reported to cause acute N2A neurite retraction through a mechanism involving activation of the RhoA/Rho kinase and PLC/IP3R/Ca2+ signaling pathways (Zimering M B., *J Endocrinol Diab.* 2017; 4(4):1-10; and Zimering M B. *J Endocrinol Diabetes.* 2018; 5(2): 10). In the present study, neurite retraction induced by IgG autoantibodies (5-HT2A receptor antibodies) from patients with SCZ was completely prevented by co-incubating N2A cells with a ten micromolar concentration of the selective Rho kinase inhibitor Y27632 or a one micromolar concentration of the selective Gq11 inhibitor Y254890 (Table 21). In addition, a one micromolar concentration of the phospholipase C inhibitor U73122, and a 50 micromolar concentration of the IP3R antagonist 2-APB each significantly protected (72-83%) against autoantibody (IgG)-induced neurite retraction (Table 21) using autoantibodies from patients with SCZ. Taken together, these data suggest that autoantibody (IgG)-induced neurite retraction using autoantibodies from patients with SCZ likely involves activation of both RhoA/Rho kinase and Gq/11/PLC/IP3R/Ca2+ signaling pathways.

TABLE 21

Mechanism of acute N2A neurite retraction
induced by plasma AutoAB
from patients with schizophrenia

| Treatment | Conc | % of AutoAB-induced neurite retraction |
|---|---|---|
| SCZ IgG (N = 2) alone | 40 nM | 100 ± 0% |
| AutoAB + Y27632 (ROCK inhibitor) | 10 μM | 0 ± 0% |
| AutoAB + 2-APB (IP3R antagonist) | 50 μM | 17 ± 1.9% |
| AutoAB + U73122 (PLC inhibitor) | 1 μM | 28 ± 15% |
| AutoAB + YM-254890 (Gq11 inhibitor) | 1 μM | 0 ± 0% |

A forty nanomolar concentration of plasma autoantibodies (AutoAB) from Pt 1 or Pt, schizophrenia, was incubated in the presence or absence of the indicated concentration of RhoA/Rho kinase (ROCK) inhibitor, or individual antagonists of the Gq11/PLC/IP3R signaling pathway. Results are (mean+/−SD) acute N2A neurite retraction occurring in response to IgG autoantibodies from Pt 1 or Pt 2.

Figure 8A:
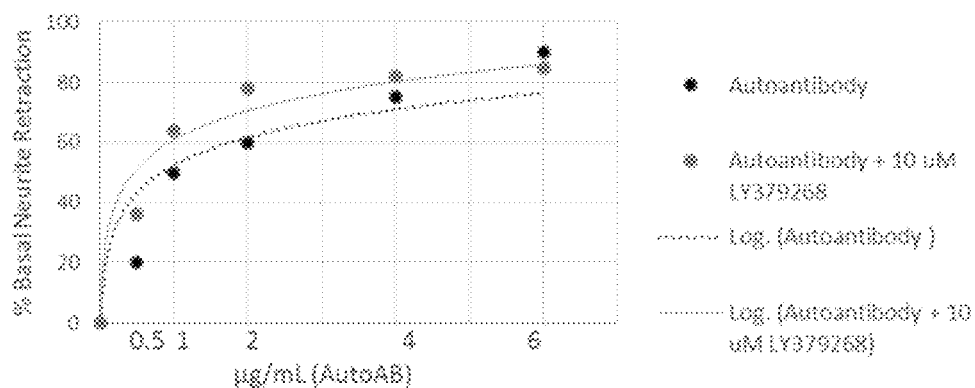
FIGS. 8A-B shows the results of LY379268 on neurite retraction.
Figure 8B:
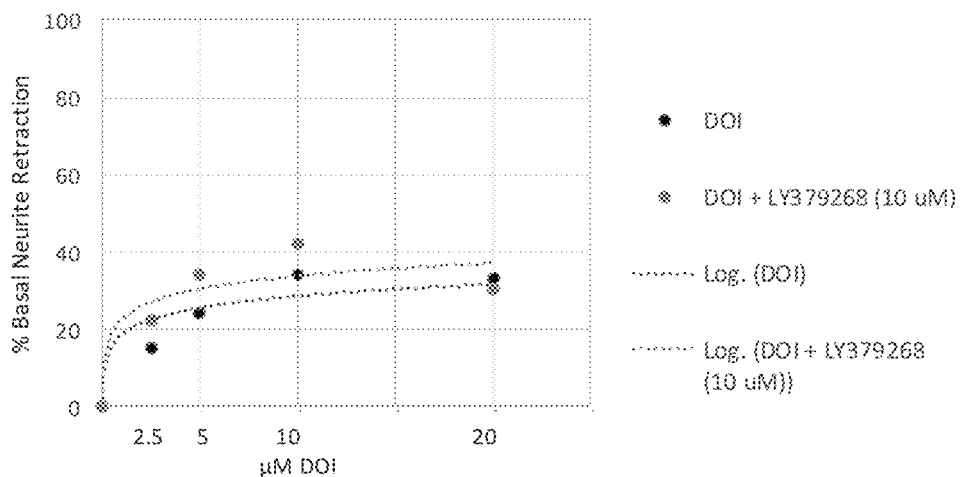
Figure 9:
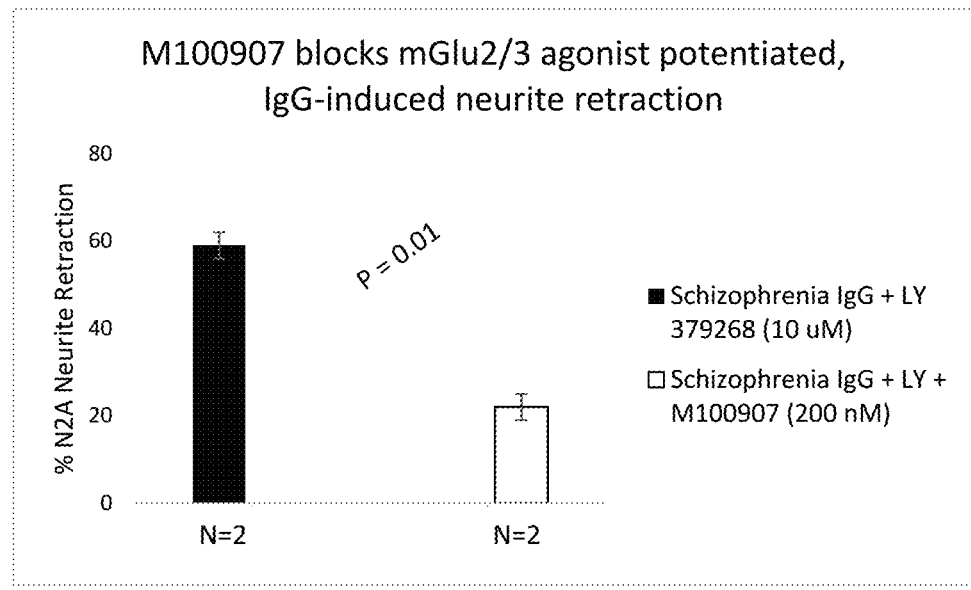
FIG. 9 shows schizophrenia plasma autoantibodies (Pt 1, 2) were incubated with a micromolar concentration of LY379268 alone (solid bars) or with (open bars) a two-hundred nanomolar concentration of the selective 5-HT2AR antagonist M100907 in N2A cells. Results are mean±SE.

Modulation of autoantibody (IgG)-induced neurite retraction by LY 379268, a potent mGlu2/3R agonist using autoantibodies from patients with SCZ. Cross-signaling between Glu2/3R and 5HT2AR was inferred from differences in autoantibody (IgG)-induced N2A acute neurite retraction occurring in the presence or absence of the mGlu2/3R agonist LY379268, at 5-101.1M concentrations (of LY379268) which alone had no effect on neurite retraction. The mGlu2/3R agonist LY379268 was previously reported to cause positive allosteric modulation of the 5HT2AR protomer affinity at 5HT2AR/mGlu2R heteromers (González-Maeso J, et al., *Nature.* 2008; 452(7183):93-97). A one microgram per milliliter concentration (~7 nM) of the potent IgG autoantibodies from Pt 1, SCZ, caused 50% inhibition of N2A neurite outgrowth (FIG. 8A). Pre-incubation (for 5 minutes) followed by co-incubation of N2A cells with a 10 micromolar concentration of LY379268 caused a 'shift to the left' in the dose-response curve of the Pt 1 plasma autoantibody (IgG)-induced neurite retraction: 50% inhibition of N2A neurite outgrowth occurred at substantially lower, i.e., ~0.5 microgram per milliliter concentration (3.5 nM) of IgG autoantibodies from Pt 1(FIG. 8A). The "potentiating effect" of 10 μM LY379268 on neurite retraction was more pronounced at low concentrations of plasma autoantibodies (IgG) from patients with SCZ ranging from (3.5-14 nM) (FIG. 8A). Presumably, at these lower concentrations a high proportion of unoccupied 5HT2A receptors are available to undergo positive allosteric modulation via mGlu2R protomer binding to LY379268. The dose-response curve for DOI-induced neurite retraction underwent a 'shift-to-the-left' in the presence of (10 μM) LY379268: the concentration of DOI needed to evoke 25-30% neurite inhibition decreased from 10 μM (in the absence of LY379268) to 5 μM in the presence of LY379268 (FIG. 8B). A saturating concentration of the reversible 5-HT2AR agonist DOI (20 μM) caused 40% peak neurite retraction compared to 50% neurite retraction induced by an 2000-fold lower concentration (7 nM) of potent plasma IgG 5 autoantibodies (FIG. 8) using autoantibodies from patients with SCZ.

LY379286-potentiated plasma IgG autoantibody-induced neurite retraction using antibodies from patients with SCZ was significantly prevented by co-incubation with the highly selective 5HT2AR antagonist M100907 (500 nM) suggesting mGlu2/3R agonism enhanced neurite retraction via 5HT2AR-dependent signaling. One possibility is that an mGlu2/3R agonist increased 5HT2AR receptor affinity for plasma IgG autoantibodies using autoantibodies from patients with SCZ via a heteromeric receptor-receptor interaction as was previously reported for mGlu2/3 agonist action at the 5HT2AR/mGlu2R complex (González-Maeso J, et al., *Nature.* 2008; 452(7183):93-97).

Potentiation of 5HT2AR-mediated neurite retraction (by a 10 μM concentration of LY379268) was observed in the IgG autoantibodies from twelve patients tested including: chronic paranoid schizophrenia (n=5), Parkinson's disease (n=5), dementia (n=1) and diabetic nephropathy (n=1). The mean level of neurite retraction (induced by an autoantibody (IgG) concentration which alone caused ~50% retraction) was significantly increased in the presence of 10 μM LY379268 (74±10% vs 52±7%; P<0.001; n=12) (Table 22).

TABLE 22

Mean N2A neurite retraction induced by neurovascular pathologies' AutoAB in the presence or absence of (7.5-10 µM) LY379268, a selective mGlu2/3R agonist

| Pathologies (N = 12) | Mean [IgG]. | Pt IgG. | Pt IgG + LY379268 | P-value |
|---|---|---|---|---|
| Schizophrenia (5), PD(4), Other (3) | 17 ± 6 nM | 52 ± 7%^ | 74 ±10%^ | <0.001 |

^Mean acute N2A neurite retraction (after five minutes' incubation) in the presence of the indicated mean concentration of plasma autoantibodies (protein-A eluate fraction) with or without a 7.5-10 µM concentration of the mGlu2/3R agonist LY379268.

Other pathologies: n=1 dementia, n=1 diabetic nephropathy, n=1 major depressive disorder Balanced Gq/11- and Gi/o-coupled signaling in response to plasma IgG autoantibodies obtained from patients with SCZ. Second generation anti-psychotic medications, e.g., clozaril, risperodone, exhibit high affinity binding to 5-HT2AR and bias 5-HT2AR signaling in favor of Gi-coupled pathways (Weiner D M, et al., *J Pharmacol Exp Ther.* 2001; 299(1):268-76). They also bind less avidly to the dopamine 2 receptor, D2R (Weiner D M, et al., *J Pharmacol Exp Ther.* 2001; 299(1):268-76). The reversible 5-HT2AR hallucinogenic agonist DOI biases signaling in favor of Gq/11 (Schmid C L, et al., *Proc Natl Acad Sci USA.* 2008; 105(3):1079-8). Yet the irreversible 5-HT2AR agonist LSD, and serotonin and its psychoactive metabolites promotes a mix of Gi- and Gq/11 coupled signaling (Wacker D, et al., *Cell.* 2017; 168(3):377-389 Zimering M B, *J Endocrinol Diabetes.* 2018; 5(2); and Schmid C L, et al., *Proc Natl Acad Sci USA.* 2008; 105(3):1079-8). Psychosis can occur in subsets of major depressive disorder and in ~50% of Parkinson's disease patients. Thus, it was next investigated whether the ability to evoke survival promotion in N2A cells might differentiate autoantibodies in a subset of psychosis-prone patients and the mechanisms underlying autoantibody-induced N2A survival promotion.

Figure 10A:
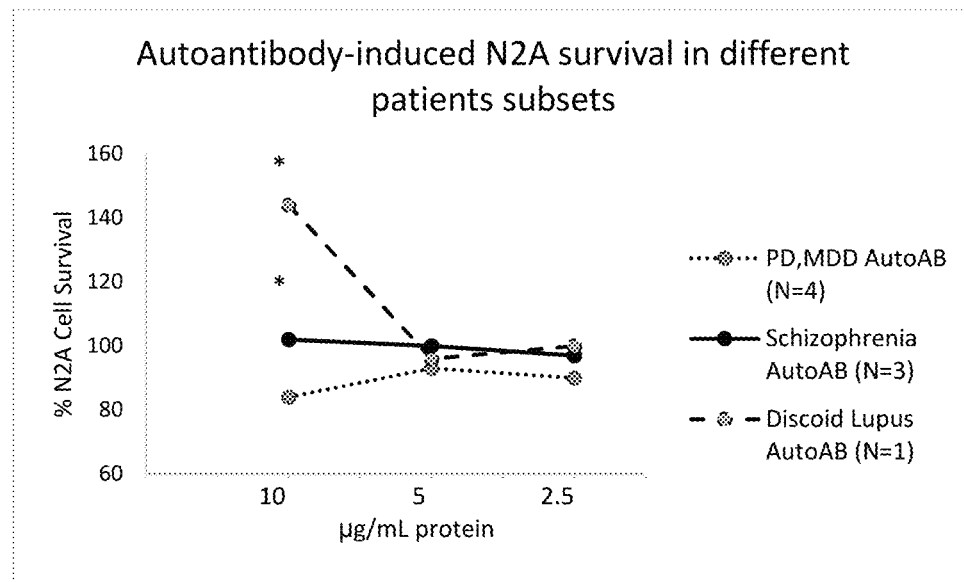
FIGS. 10A-B shows the effects of autoantibodies on survival and proliferation in N2A cells.

Plasma IgG autoantibodies in Patients 1, 2, 4 having chronic schizophrenia (10 µg/mL) caused dose-dependent increased N2A cell survival compared to an identical concentration of IgG autoantibodies from four patients with either MDD (n=3) or PD (n=1), one of whom (PD) had experienced visual hallucinations (FIG. 10A). The autoantibodies from a patient with the systemic autoimmune condition discoid lupus erythematosus caused significantly greater N2A growth stimulation (144%±5% vs. 102±8%; P<0.01) compared to mean growth stimulation in an identical concentration of the autoantibodies from three chronic schizophrenia patients (FIG. 10A).

Figure 10B:
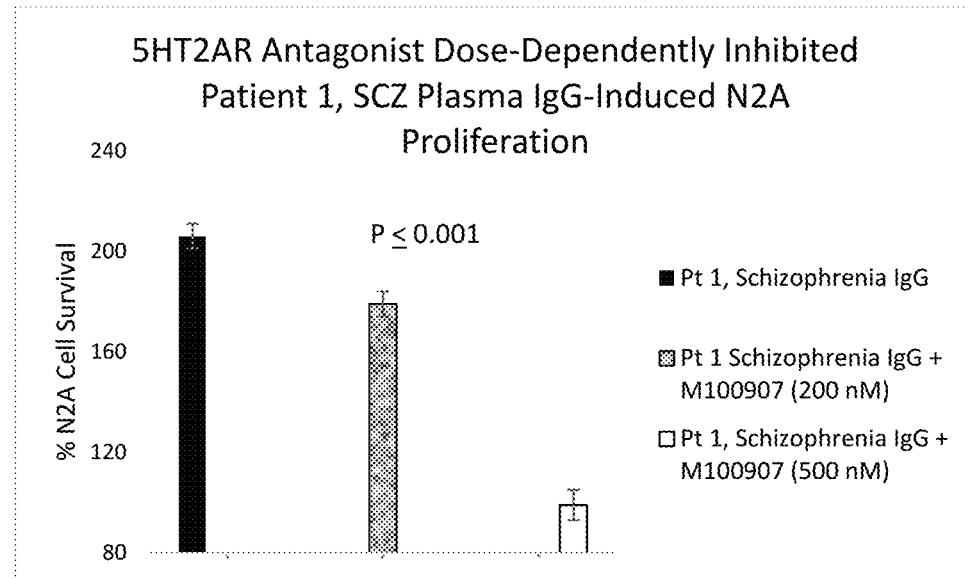
Figure 11A:
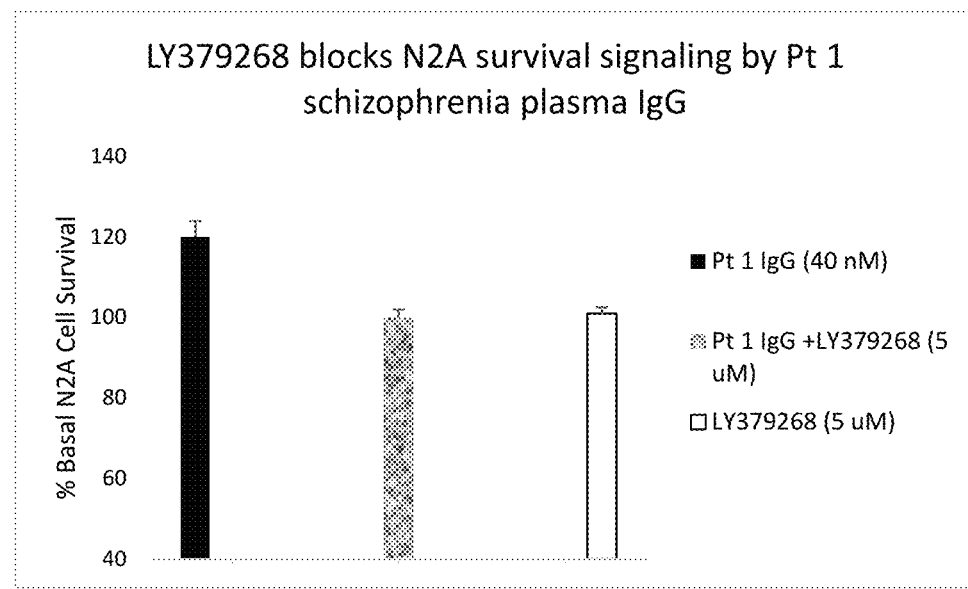
FIGS. 11A-B shows the effects of autoantibodies from subjects diagnosed with schizophrenia in the presence of a mGlu2R agonist LY379268 or pertussis toxin.
Figure 11B:
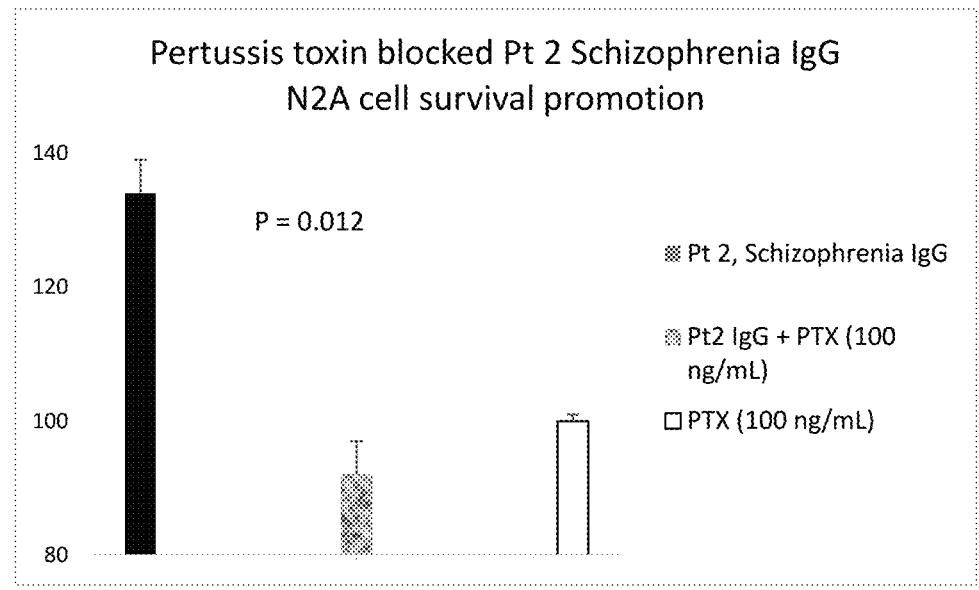
Figure 12A:
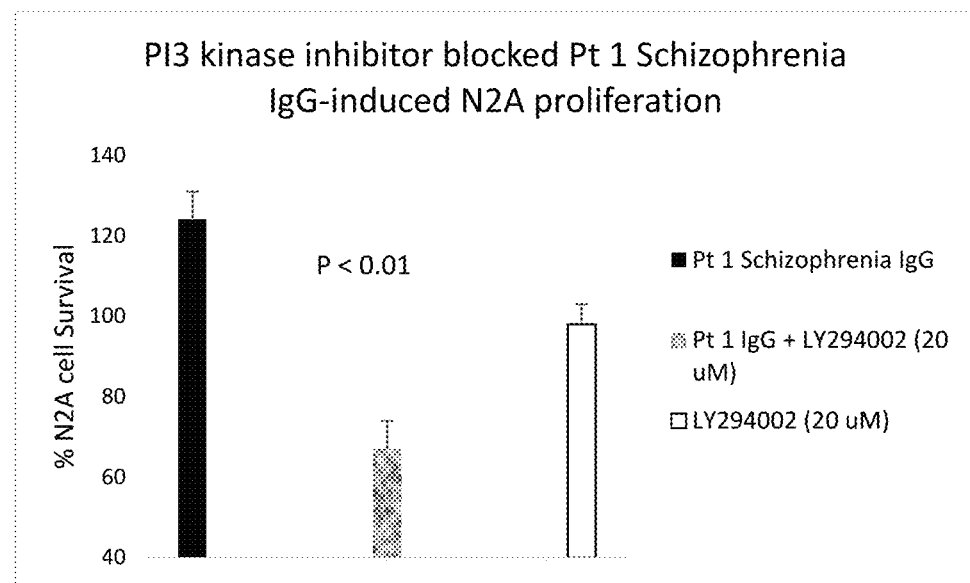
FIGS. 12A-B shows the effects of a PI3 kinase inhibitor on IgG autoantibodies from patients diagnosed with schizophrenia or major depression. Pt 1's schizophrenia plasma autoantibodies (40 nM) (FIG. 12A) Pt 3's major depression with psychotic features autoantibodies (FIG. 12B) were incubated alone (solid bar) or in the presence (speckled bar) of a twenty micromolar concentration of the PI3-kinase inhibitor LY294002 in N2A cells for 24 hours. Results are mean±SE. Similar results were obtained with two additional schizophrenia patient plasma autoantibodies.
Figure 12B:
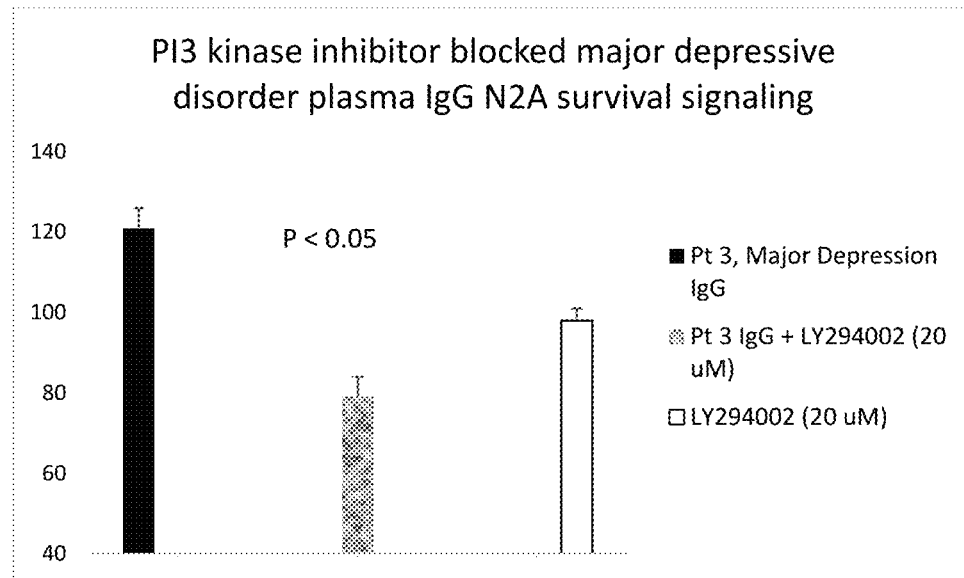

Mechanism of N2A pro-survival effect in plasma autoantibodies from psychosis prone subset. Serotonin 2A receptor activation leads to f3-arrestin-2-mediated desensitization and receptor internalization. However, β-arrestin-2 can also couple with diverse signaling pathways leading to enhanced cell proliferation and/or survival promotion. Using IgG autoantibodies from Pt 1, chronic paranoid schizophrenia, promoted increased N2A cell proliferation which was significantly blocked by 500 nM concentration of M100907 (FIG. 10B) consistent with 5HT2AR-mediated proliferation signaling. LY379268 (5 µM) alone had no effect on N2A survival, but it significantly blocked autoantibody-induced pro-survival effect on N2A cells (FIG. 11A) using autoantibodies from Pt 1 and Pt 2, schizophrenia. Pertussis toxin (100 ng/mL) had no effect alone on N2A cell survival, but significantly blocked the pro-survival effect of autoantibodies (IgG) on N2A cells (FIG. 11B) using autoantibodies from Patient 2, SCZ. Finally, the PI3-kinase inhibitor LY294002 (20 µM) significantly decreased N2A survival-promotion induced by autoantibodies from patients with schizophrenia (Pt 1), and major depression with psychotic features (Pt 3) (FIG. 12A-B).

Figure 13:
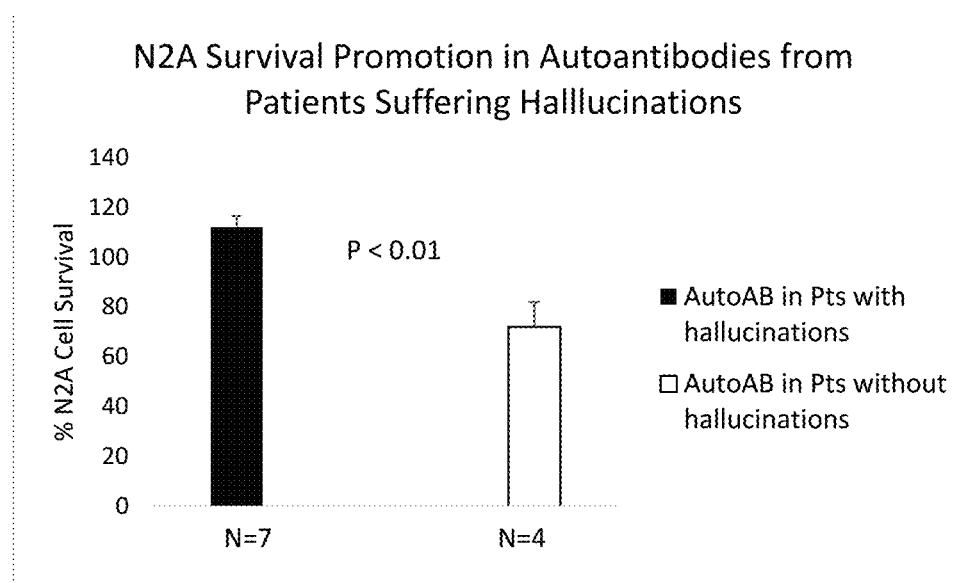
FIG. 13 shows the mean N2A cell survival after 24 hours incubation in the presence of an identical 40 nM concentration of the plasma autoantibodies from schizophrenia (n=5), major depression (n=1), Parkinson's disease (n=1) patients suffering with hallucinations (n=7, solid bar) or from patients with major depression (n=3) or diabetes without hallucinations (n=4, open bar). Results are mean±SE.

Possible association between psychosis and autoantibody-mediated N2A survival promotion. Mean N2A survival promotion in the autoantibodies from seven patients suffering with hallucinations significantly exceeded mean N2A survival in an identical concentration of the plasma autoantibodies from four patients not suffering with hallucinations (112±14 vs 72±15; P=0.001) (FIG. 13). The patient subgroups (experiencing or not experiencing hallucinations) did not differ significantly in their baseline clinical characteristics (Table 23).

TABLE 23

Baseline characteristics in patients suffering or not suffering hallucinations

| Risk factor | Hallucinations (n = 7)^ | No Hallucinations (n = 4)* | P-value |
|---|---|---|---|
| Age (years) | 64.3 ± 9.1 | 71.5 ± 15.0 | 0.33 |
| Glycosylated Hgb (%) | 7.7 ± 1.0 | 7.7 ± 0.9 | 0.93 |
| Diabetes duration (years) | 13.3 ± 6.1 (7) | 8.7 ± 2.6 | 0.30 |

^Schizophrenia (n = 5), Major depression (n = 1), Parkinson's disease (n = 1)
*Major depression (n = 3), type 2 diabetes without neuropsychiatric disorder (n = 1)

Discussion Described herein are results demonstrating the existence of 5-HT2AR-activating IgG autoantibodies in plasma from a subset of chronic schizophrenia patients. The 5-HT2A receptor autoantibodies caused potent, irreversible Gq/11-mediated neurite retraction in N2A cells by a mechanism involving activation of RhoA/ROCK and Gq 11-coupled, PLC/IP3R signaling pathways. In patients suffering with severe, recurrent hallucinations and suicidal ideation, the 5-HT2A receptor autoantibodies also promoted N2A cell survival and/or proliferation (in part) via apparent recruitment of additional Gi-coupled, PI3-kinase-dependent survival signaling. LY379268 blocked 5HT2AR-dependent, Gi-coupled, N2A survival signaling in 5-HT2A receptor autoantibodies from patients suffering with hallucinations in agreement with the report of Gonzalez-Maeso et al. (González-Maeso J, et al., *Nature.* 2008; 452(7183):93-97) of similar effects of LY379268 on hallucinogen-specific induction of egr-2.

The 5-HT2A receptor mediates diverse signaling pathway activation in response to different ligands (Schmid C L, et al., *Proc Natl Acad Sci USA.* 2008; 105(3):1079-84), a phenomenon which has been referred to as "functional selectivity" or "biased agonism." Beta-arrestin-2-directed signaling plays an important role in receptor internalization and desensitization, as well as acting as a scaffold to organize extracellular regulated-kinase MAPK signaling cascades (Luttrell L M, et al., *Proc Natl Acad Sci USA.* 2001; 98(5):2449-2454) and components of the PI3-kinase/Src/Akt cell survival pathway (Schmid C L, Bohn L M. *J Neurosci.* 2010; 30(40):13513-13524). The latter pathway is active in cancer cells (Hennessy B T. et al., *Nature Reviews Drug Discovery* 2005: 4:988-1004) including neuroblastoma (Johnsen J I, et al., *Oncogene.* 2008; 27(20):2910-2922). Lysergic acid diethylamine (LSD) causes long-lasting 5-HT2AR activation and biased, β-arrestin-2-directed signaling (Wacker D, et al., *Cell.* 2017; 168(3):377-389) providing a further link between a 'mix' of Gq/11-coupled and β-arrestin-2-directed signaling and psychomimetic effects associated with a subset of long-lasting 5-HT2AR agonists, i.e., 5-HT2A receptor autoantibodies from patients with schizophrenia.

Sensitization of 5-HT2A receptor autoantibody-induced neurite retraction by the mGlu2/3R agonist LY379268 is consistent with Gonzalez-Maeso et al. (Gonzalez-Maeso J, et al., Nature. 2008; 452(7183):93-97) and suggests positive allosteric modulation of the 5HT2AR protomer affinity at functional 5HT2AR/mGlu2R complexes in N2A neuroblastoma cells as a plausible mechanism. Receptor heteromers have been reported in neuroblastoma cell, e.g., A2R/D2R (Fuxe K, et al., Neurology. 2003; 61(11 Suppl 6):519-23), and both 5HT2AR (Zimering M B, J Endocrinol Diab. 2017; 4(4):1-10) and mGlu2R (Wang J, et al., PLoS Pathogens. 2018; 14(7)) are normally expressed in mouse neuroblastoma cells. Yet in these experiments, the dopamine 2 receptor (D2R) agonist quinpirole (10 µM) did not sensitize N2A cells to plasma 5-HT2A receptor autoantibody- (n=4 different patients) or DOI-induced neurite retraction using autoantibodies from patients with schizophrenia suggesting that targeting of the 5-HT2AR by plasma 5-HT2A receptor autoantibodies from patients with schizophrenia is specific for homomers or 5-HT2AR/mGlu2R heteromers.

Targeting mGlu2R agonism as a mechanism to suppress presynaptic glutamate release (via mGlu2 autoreceptors) reduced certain psychomimetic drug effects in animals, but did not lead to overall reduction in both negative and positive symptoms in schizophrenia patients (Muguruza C, et al., Front Pharmacol. 2016 May 20; 7:130). Sensitization of 5-HT2AR-mediated neurite withdrawal by an mGlu2/3 agonist demonstrated here (in vitro) suggests a possible mechanism in which mGlu2R agonism may promote a 'negative symptom' in schizophrenia. For example, major depression autoantibodies from patients with major depression suffering with anhedonia, a negative symptom in schizophrenia, caused robust Gq/11-mediated neurite retraction in N2A neuroblastoma cells (Zimering M B, J Endocrinol Diab. 2017; 4(4):1-10) as well as led to decreased sucrose preference, the behavioral equivalent of anhedonia, in mice following autoantibody intracerebroventicular infusion (Zimering M B, et al., (2015) J Endocrinol Diab 2015; 2(2): 11). These data suggest that Gq/11-mediated neurite retraction may be useful as a biomarker in drug discovery aimed at reducing combined negative and positive symptoms in schizophrenia.

Excessive glutamatergic signaling in the cortex and striatum is a feature of 5-HT2AR activation which may underlie (in part) delusions and hallucinations occurring in schizophrenia (Aghajanian G K, et al., Brain Res Brain Res Rev. 2000; 31(2-3):302-312) and in a subset of Parkinson's disease. Serotonin 2A receptor agonism promotes neuronal glutamate release (Ansah T A, et al., Front Systems Neurosci 2011) which in turn may enhance 5-HT2AR protomer affinity at 5HT2AR/mGlu2R heteromers in the prefrontal cortex. Since constitutive activation of Gq11-coupled GPCR signaling was reported to recruit additional Gi-coupled downstream signaling in independent GPCRs (Baker R A, et al., J Biol Chem. Vol. 2004: 279(7) 5152-5161), the possibility that some 'cross-talk' between 5HT2AR and mGlu2R agonism may occur (in part) via mechanisms occurring downstream of direct receptor-receptor interaction(s) cannot be ruled out.

5-HT2A receptor autoantibodies in a subset of psychosis-prone individuals might possess structural characteristics which bias 5-HT2AR signaling in favor of dual Gq/11 and Gi-coupled, or β-arrestin-2-directed pathways. One possibility is circulating immune complexes which were reported to increase in patients with schizophrenia (Mailian K. R., et al., Zh. Nevrol. Psikhiatr. Im. S S. Korsakova 2005; 105: 55-60). Systemic autoimmunity, characterized by a high prevalence of immune complexes, is a risk factor for schizophrenia identified in prior studies (Benros M E, et al., Annals of the New York Academy of Sciences. 2012; 1262:56-66). Circulating immune complexes in chronic lymphocytic leukemia (CLL) promoted increased B cell survival through activation of anti-apoptotic and pro-survival signaling pathways (Balakrishnan K, et al., Leukemia. 2015; 29(9):1811-1822) and in a prior report, the autoantibodies in a Parkinson's disease patient with CLL strongly promoted increased N2A proliferation (Zimering M B, J Endocrinol Diabetes. 2018; 5(2): 10). Taken together, autoantibody-induced cancer cell proliferation and survival might suggest immune complexes which appear to promote biased signaling in favor of dual Gq/11-mediated and β-arrestin-2-directed pathway activation.

The study described herein is a cross-sectional study. As such, more study is needed to determine whether autoantibodies are present in acute-onset, or drug-naive schizophrenia or in other psychotic disorders. Long-standing type 2 diabetes mellitus was associated with 5-HT2AR-activating 5-HT2A receptor autoantibodies in patients having diffuse microvascular injury and chronic inflammation, e.g., diabetic kidney disease (Zimering M B, J Endocrinol Diab. 2017; 4(4):1-10; and Zimering M B, J Endocrinol Diabetes. 2018; 5(2): 10). Yet type 2 diabetes per se is unlikely to have accounted for 5-HT2A receptor autoantibodies in the present subset of schizophrenia patients who were free of significant microvascular (i.e., renal or retinal) complications. Schizophrenia is thought to arise from complex gene-environment interactions leading to abnormal neurodevelopment. Brain-reactive antibodies occurring as a result of inflammation, infection or systemic autoimmunity is one potential environmental mechanism in schizophrenia causation (Benros M E, et al., Annals of the New York Academy of Sciences. 2012; 1262:56-66).

In summary, plasma IgG autoantibodies from patients with chronic schizophrenia appeared to activate a Gq11/phospholipase C/inositol triphosphate receptor pathway and RhoA/Rho kinase signaling to cause acute N2A neurite retraction. 5-HT2A receptor autoantibody-induced neurite retraction was positively modulated by the mGlu2/3R agonist LY379268 consistent with reported mGlu2R-driven, positive modulation of 5-HT2AR protomer affinity at 5HT2AR/mGlu2R heteromers (González-Maeso J, et al., Nature. 2008; 452(7183):93-97) found in cortical brain regions underlying perception. Biased agonism at 5-HT2AR mediated by the hallucinogen LSD (Wacker D, et al., Cell. 2017; 168(3):377-389) or by certain autoantibodies from patients suffering delusions and hallucinations involves recruitment of Gi-coupled, PI3-kinase-dependent mechanisms (which for the autoantibodies) was associated with enhanced survival in N2A neuroblastoma cells.

Example 6: Decoy Peptides Reduce Blood Pressure in Zucker Diabetic Fatty Rats

Method. Tail cuff blood pressure measurement was performed using an automated CODA noninvasive blood pressure system (Kent Scientific). The blood pressure system uses Volume Pressure Recording (VPR) tail-cuff technology and displays up to six blood pressure measurements per cycle, with validation of acceptable readings via computer algorithm. Animals are placed on an insulated warming platform to ensure proper body temperature and the cuffs are slid over the tail, and the animal is held by the examiner with light restraint. The cuff monitor is connected to a computer which automatically calculates blood pressure and analyzes each individual reading (in a cycle) for accuracy and acceptability. Results are those which passed the volume pressure recording tail cuff technology built-in quality control procedures that were displayed as acceptable.

Results.

TABLE 24

Change in systolic blood pressure in 3 Zucker Diabetic Fatty (ZDF) rats before and after peptide 2 (SEQ ID NO: 2) injection

| Animals | Day −2, pre-injection | Day 0, pre-injection | Day 0, post-injection | P-value* |
|---|---|---|---|---|
| ZDF n = 1-3 | 166 ± 24 | 161 ± 21 | 95 ± 13 | 0.018 |

Results are mean mm Hg+/−SD in three, obese male Zucker diabetic fatty rats (5.5 months old), average weight approximately 500 g who had blood pressure monitored two days before, 30 minutes before and then 15-40 minutes after receiving a 1 mg intraperitoneal injection of the linear synthetic peptide SCLLADDN (SEQ ID NO: 2) in sterile saline, which had neuroprotective effects in vitro. *P-value is comparing mean systolic blood pressure immediately before and after the peptide injection.

TABLE 25

Change in diastolic blood pressure in 3 ZDF rats around the time of injection of the putative neuroprotective peptide (SEQ ID NO: 2).

| Animals | Day −2, pre-injection | Day 0, pre-injection | Day 0, post-injection | P-value* |
|---|---|---|---|---|
| ZDF n = 1-3 | 101 ± 23 | 112 ± 2 | 65 ± 11 | 0.05 |

Results are mean mm Hg+/−SD in three, obese male Zucker diabetic fatty rats (5.5 months old), average weight approximately 500 g who had blood pressure monitored two days before, 30 minutes before and then 15-40 minutes after receiving a 1 mg intraperitoneal injection of the linear synthetic peptide SCLLADDN (SEQ ID NO: 2) in sterile saline, which had neuroprotective effects in vitro. *P-value is comparing mean systolic blood pressure immediately before and after the peptide injection.

TABLE 26

Aggregate blood pressure-lowering effect of SEQ ID NO: 2

| Animals | Before | 15-40 minutes after injection |
|---|---|---|
| ZDF n = 1-3 | 161/112 | 95/65 |

Percent lowering of systolic blood pressure after peptide (161-95)/161=41%

Percent lowering of diastolic blood pressure after peptide (112-65)/112=42%

Percent lowering of mean arterial pressure (125-75)/125=40%

Taken together these data demonstrate that a single 2 mg/kg intraperitoneal injection of the putative neuroprotective peptide SEQ ID NO: 2 (dissolved in sterile isotonic saline) causes acute substantial lowering of systolic, diastolic and mean arterial blood pressure in the Zucker diabetic fatty (ZDF) rat. The ZDF rat normally develops hypertension by age 8-10 weeks, and spontaneously develops diabetic nephropathy by age 3 months. Uncontrolled hypertension, which is known to occur spontaneously in the ZDF rat contributes to the development of diabetic nephropathy in the ZDF rat, and in humans, uncontrolled hypertension is a major risk factor for accelerated decline in kidney function and progression to end-stage renal disease. Thus, the results described herein, have demonstrated that SEQ ID NO: 2 potently lowers systolic and diastolic blood pressure in a rat which is a recognized model system for human diabetic nephropathy. The decoy peptides (SEQ ID NOs: 1-4) disclosed herein can slow the progression of human diabetic nephropathy and/or cardiovascular complications related to uncontrolled diabetic chronic kidney disease such as stroke, myocardial infarction, which are leading causes of mortality in humans with diabetic kidney disease. Because hypertension is a major risk factor for neurodegeneration, e.g., dementia, the potent-blood pressure lowering effect of decoy peptides (SEQ ID NOs: 1-4) have putative neuroprotective properties.

TABLE 27

Effect of saline injection on systolic blood pressure in Zucker lean, non-obese rats (ZLR)

| Animals | Before | 15-40 minutes after saline injection | P-value |
|---|---|---|---|
| ZLR n = 1-3 | 137 ± 10 | 26 ± 26 | 0.72 |

Intraperitoneal injection of 0.5 mL of sterile saline had no significant effect on systolic blood pressure in three Zucker lean male rats, age 5.5 months who normally are not diabetic and do not manifest either obesity or hypertension when fed the same diet as ZDF rats.

TABLE 28

Effect of saline injection on diastolic blood pressure in Zucker lean, non-diabetic rats (ZLR)

| Animals | Before | 15-40 minutes after saline injection | P-value |
|---|---|---|---|
| ZLR n = 1-3 | 88 ± 5 | 83 ± 0 | 0.42 |

Intraperitoneal injection of 0.5 mL of sterile saline had no significant effect on diastolic blood pressure in three Zucker lean male rats, age 5.5 months who normally are not diabetic and do not manifest either obesity or hypertension when fed the same diet as ZDF rats.

TABLE 29

Aggregate effect of sterile saline injection on blood pressure in Zucker lean rats.

| Animals | Before | 15-40 minutes after saline injection |
|---|---|---|
| ZLR n = 1-3 | 137/88 mm Hg. vs. | 126/83 mm Hg |

Sterile saline (vehicle) had no significant effect on blood pressure lowering in Zucker lean rats. Zucker lean rats are normotensive, normoglycemic and do not spontaneously develop nephropathy. Unlike their Zucker diabetic fatty rat counterparts, the Zucker lean rat did not harbor long-lasting neurotoxic 5-hydroxytryptamine receptor-activating autoantibodies in their circulation. One possible explanation for this finding is that a component of the persistent, moderately-severe hypertension manifested in ZDF rats is due in part to sustained activation of the 5-hydroxytryptamine receptor on vascular smooth muscle cells by the circulating 5-HT2A receptor autoantibodies which are specific to the obese, diabetic Zucker rat and not present in the lean, non-diabetic non-hypertensive Zucker lean rat. Since co-incubation of 5-hydroxytryptamine 2A receptor autoantibodies together with SEQ ID NO: 2 prevented cell toxicity associated with activation of G-protein coupled signaling in vitro [Zimering, 2019], the mechanism of ZDF blood pressure lowering by injection of SEQ ID NO: 2 in vivo may involve interference with 5-hydroxytryptamine 2A receptor autoantibodies binding to their 5-HT2A receptors which normally elicits an increase in arterial vascular tone.

Because Zucker lean rat are normotensive, the effect of SEQ ID NO: 2 in ZDL rats was not systematically investigated, as there would be no indication to treat these animals with a blood pressure lowering agent, and absent circulating 5-HT2A receptor activating autoantibodies, there would be no indication to neutralize other potentially harmful peripheral and CNS effects from such 5-HT2A receptor autoantibodies.

Eighteen days after three ZDF rats each received approximately 1 mg of SEQ ID NO: 2 (in sterile saline) as a single intraperitoneal injection, no untoward side effects were observed and the animals were alive and behaving normally.

Surprisingly, within 30 minutes of having received the initial peptide injection, the three ZDF rats fell asleep and appeared sedate and calm in their cages or when held by the examiner for blood pressure measurements. Normally these rats will feed nearly continuously when given the opportunity. This sedating effect was reproducible following a second IP injection of 1 mg of the SEQ ID NO: 2 in each of the 3 ZDR rats. These results suggest that an additional central nervous system mechanism may be responsible for the sedative effect. Serotonin plays a major role in wakefulness and arousal in the nervous system. It is possible that the administration of SEQ ID NO: 2 blocks the action of the neurotransmitter serotonin at multiple sites in the periphery and in the central nervous system, inducing sleep via antagonism of serotonin's role in wakefulness/arousal, independent of the pronounced blood pressure-lowering effect.

Next, the IP injection of approximately 1 mg of SEQ ID NO: 2 (at a concentration of 2 mg/kg body weight) was repeated in the same 3 ZDF rats. Blood pressure post-injection was monitored at longer time intervals.

TABLE 30

Effect of SEQ ID NO: 2 (IP injection) on SYSTOLIC blood pressure lowering in ZDF rats.

| Animal | Before | 15 mins post-injection | P-value |
|---|---|---|---|
| ZDF1 | 158 ± 5 (N = 2) | 109 ± 5 (N = 5) | 0.0002 |
|  | Before | 45 mins-post injection |  |
| ZDF1 | 58 ± 5 (N = 2) | 104 ± 14 (N = 5) | 0.007 |
|  | Before | 90 mins-post injection |  |
| ZDF1 | 158 ± 5 (N = 2) | 119 ± 8 (N = 3) | 0.02 |
|  | Before | 240 mins-post injection |  |
| ZDF1 | 158 ± 5 (N = 2) | 97 ± 13 (N = 3) | 0.016 |
|  | Before | 15 mins post-injection |  |
| ZDF2 | 168 ± 9 (N = 3) | 128 ± 8 (N = 2) | 0.04 |

TABLE 30-continued

Effect of SEQ ID NO: 2 (IP injection) on SYSTOLIC blood pressure lowering in ZDF rats.

| Animal | Before | 45 mins post-injection | P-value |
|---|---|---|---|
|  | 168 ± 9 (N = 3) | 99 ± 16 (N = 3). | 0.018 |
|  | Before | 15 mins post-injection |  |
| ZDF3 | 174 ± 6 (N = 2) | 146 ± 4 (N = 2) | 0.05 |

TABLE 31

Effect of SEQ ID NO: 2 (IP injection) on DIASTOLIC blood pressure lowering in ZDF rats.

| Animal | Before | 15 mins post-injection | P-value |
|---|---|---|---|
| ZDF1 | 135 ± 4 (N = 2) | 69 ± 12 (N = 5) | 0.0015 |
|  | Before | 45 mins post-injection |  |
| ZDF1 | 135 ± 4 (N = 2) | 80 ± 7 (N = 5). | 0.0002 |
|  | Before | 90 mins post-injection |  |
| ZDF1 | 135 ± 4 | 69 ± 5 (N = 4) | 0.005 |
|  | Before | 240 mins post-injection |  |
| ZDF1 | 135 ± 4 (N = 2) | 45 ± 7 (N = 3) | 0.0009 |
|  | Before | 15 mins post-injection |  |
| ZDF2 | 129 ± 5 (N = 3) | 84 ± 6 (N = 2) | 0.005 |
|  | Before | 45 mins post-injection |  |
| ZDF2 | 129 ± 5 (N = 3) | 74 ± 17 (N = 3) | 0.01 |
|  | Before | 15 mins post-injection |  |
| ZDF3 | 132 ± 1 (N = 2) | 104 ± 12 (N = 3) | 0.089 |

Taken together, a single 2 mg/kg intraperitoneal injection of SEQ ID NO: 2 in sterile saline caused potent systolic and diastolic blood pressure-lowering in ZDF rats, an effect which lasted for at least four hours or longer.

Next, the IP injection of approximately 0.6-0.8 mg of SEQ ID NO: 2 (at a concentration of 2 mg/kg body weight) in a cohort (N=5) of 11-week-old ZDF rats (weighing ~300-400 mg) was investigated. Blood pressure was monitored before, fifteen minutes after (N=5 animals) and 8 hours (N=3 animals) after IP injection of SEQ ID NO 2 in sterile saline.

TABLE 32

Effect of SEQ ID NO: 2 (IP injection) on SYSTOLIC blood pressure lowering in 11-week-old ZDF rats.

| Animals | Before | 15 mins post-injection | P-value |
|---|---|---|---|
| ZDF (N = 5) | 167 ± 24 (N = 10) | 135 ± 18 (N = 17) | 0.0004 |
|  | Before | 8 hours post-injection |  |
| ZDF (N = ~3) | 171 ± 25 (N = 7) | 80 ± 7 (N = 8). | 0.01 |

A 2 mg/kg IP injection of SEQ ID NO 2 in sterile saline caused significant blood pressure-lowering in 11-week-old male ZDF rats (after 15 minutes) and in three ZDF rats who had repeat blood pressure measurement 8 hours after injection, there was a significant sustained systolic blood pressure-lowering effect following the one-time injection of SEQ ID NO 2.

TABLE 33

Effect of SEQ ID NO: 2 (IP injection) on DIASTOLIC blood pressure lowering in 11-week-old ZDF rats.

| Animals | | | P-value |
|---|---|---|---|
| | Before | 15 mins post-injection | |
| ZDF (N = 5) | 118 ± 22 (N = 10) | 91 ± 15 (N = 17) | 0.002 |
| | Before | 8 hours post-injection | |
| ZDF (N = −3) | 113 + 22 (N = 7) | 80 + 7 (N = 8). | 0.036 |

TABLE 34

Aggregate blood pressure-lowering effect of SEQ ID NO: 2 in 11-week old ZDF rats.

| Animals | Before | 15 minutes after injection |
|---|---|---|
| ZDF n = 5 | 167/118 | 135/91 |

Percent lowering of systolic blood pressure after peptide (167-135)/167=19%

Percent lowering of diastolic blood pressure after peptide (118-91)/118=23%

Percent lowering of mean arterial pressure (134-106)/134=21%

Taken together, a 2 mg/kg IP dose of SEQ ID NO 2 in sterile saline caused a 21% significant reduction in mean arterial blood pressure in five 11-week old Zucker diabetic fatty rats, 15 minutes after its administration; and in 3 rats tested, the effect was long-lasting for up to 8 hours or possibly longer. Since the ZDF rat is reported to spontaneously develop hypertension at around 9-10 weeks of age, this suggests that decoy peptide SEQ ID NO 2, can protect against damaging effects of hypertension on later adverse outcomes, early in the course of hypertension, as well as later in the course of hypertension as demonstrated in the 5 months old ZDF rats (Tables 24-31).

Figure 17:
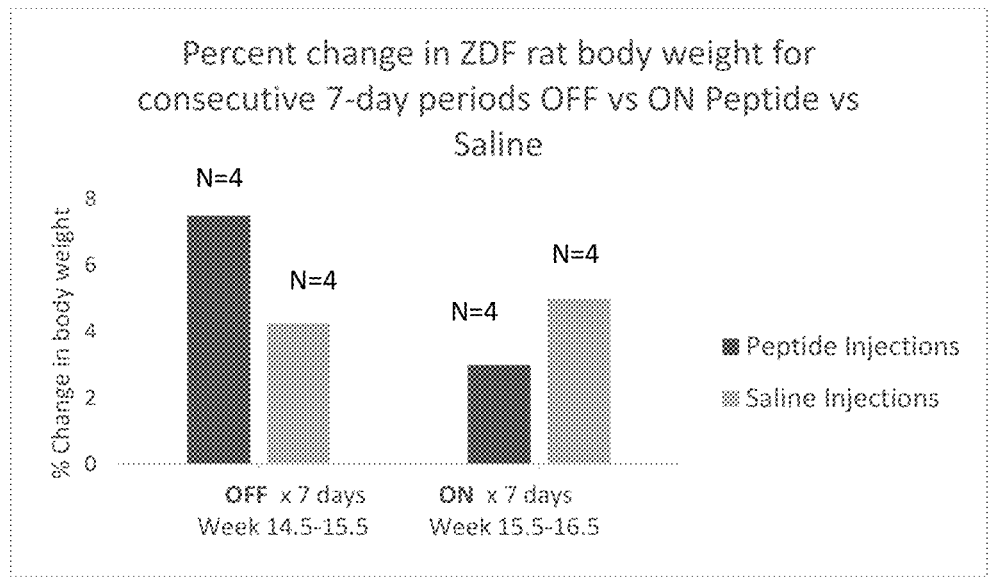
FIG. 17 shows the percent change in body weight for consecutive 7 day periods in ZDF rat administered nothing (first 7 days) or peptide 2 (SEQ ID NO: 2) or saline (second 7 days).

Example 7: Decoy Peptides Reduce Promote Weight Loss in Obese, Diabetic Zucker Diabetic Fatty Rats FIG. 17 shows the percent change in body weight in ZDF rats during two consecutive (7-day) time periods after administration of peptide 2 (SEQ ID NO: 2) or saline. Before this time period, at age 11-14.4 weeks, the ZDF rats were administered peptide or saline every other day (alternate day treatment injections). Then, at age 14.5-15.5 weeks, the ZDF rats were OFF peptide and OFF saline injection (e.g., did not receive either a peptide injection or a saline injection). During this time period, the peptide-treated group (dark bars) showed a compensatory larger increase in body weight of 7.5% (their weight gain had been suppressed prior to the OFF period) compared to the saline-treated group which gained 4.25% body weight. At age 15.5-16.5 weeks, the ZDF rats received either alternate daily 2 mg/kg peptide 2 (Peptide; SEQ ID NO: 2) or an equal volume of sterile saline (Saline). At the end of 7-day ON treatment, the peptide-treated group showed a 3% increase in body weight and the saline-treated group showed a 5% increase in body weight. In other words, when the peptide injections were resumed at age 15.5-16.5 weeks, suppression of feeding was observed in peptide-treated group which resulted in a larger decrease in weight gain compared to the prior week (e.g., 14.5-15.5) when they did not receive the peptide injections (OFF peptide). The amount of weight gain in the saline-treated group was relatively unchanged during the consecutive weeks OFF vs ON saline in which the saline-treated rats showed no difference in body weight gain ON vs OFF treatment: 4.25% vs 5%. ZDF rats treated with the peptide 2 (SEQ ID NO: 2) showed 2.5-fold reduction in percent weight gain 3% vs 7.5% ON vs OFF treatment. So, regardless of whether the rats were administered saline (OFF or ON saline), the amount of weight gain was relatively stable (+4-4.5%). Substantial differences were, however, observed during alternative weeks of receiving peptide injections (OFF vs ON peptide). OFF therapy, the peptide-treated ZDF rats gained 7.5% and ON therapy, they gained about 3% body weight, resulting in about a 250% difference. These data demonstrate that even short exposure (7 days) to alternative daily dosing of the peptide dramatically affects body weight.

Figure 18:
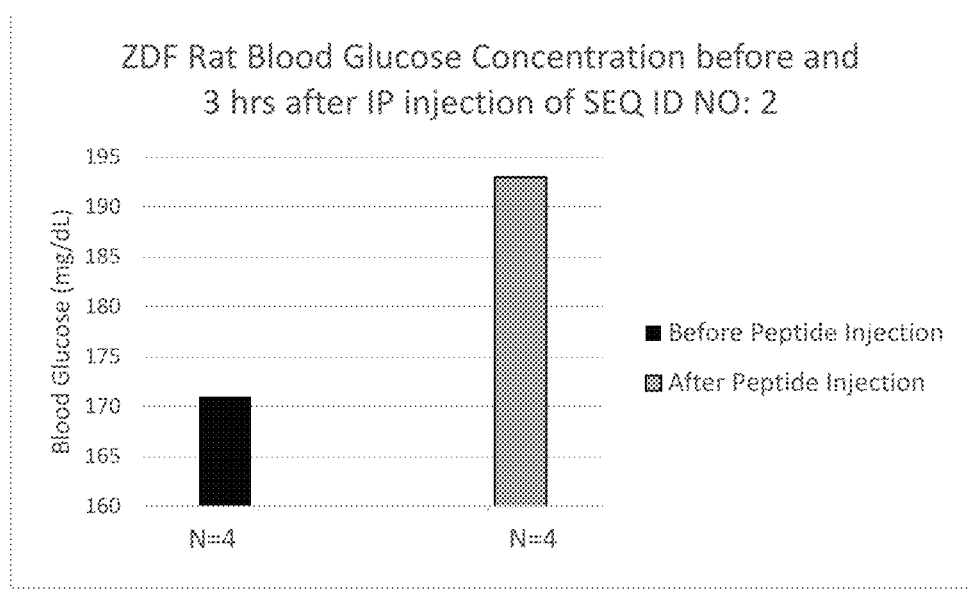
FIG. 18 shows that a single IP injection of peptide 2 (SEQ ID NO: 2) acutely increases blood glucose in ZDF rats.
Figure 19:
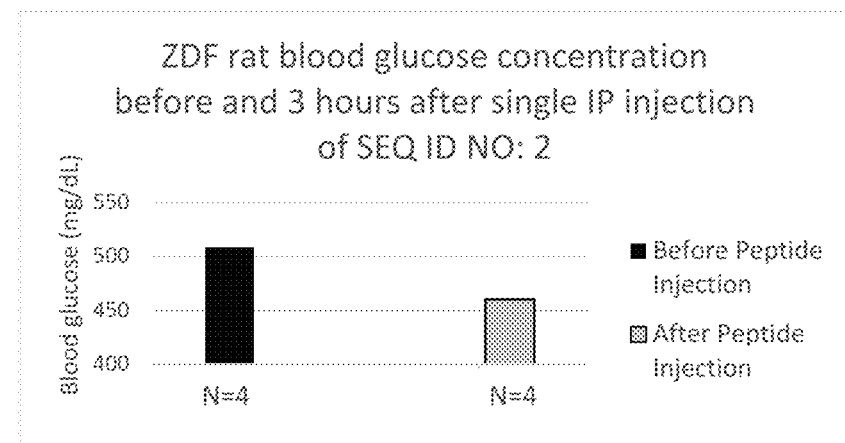
FIG. 19 shows that blood glucose concentration in ZDF rats before and 3 hours after a single IP injection of peptide 2 (SEQ ID NO: 2).
Figure 20:
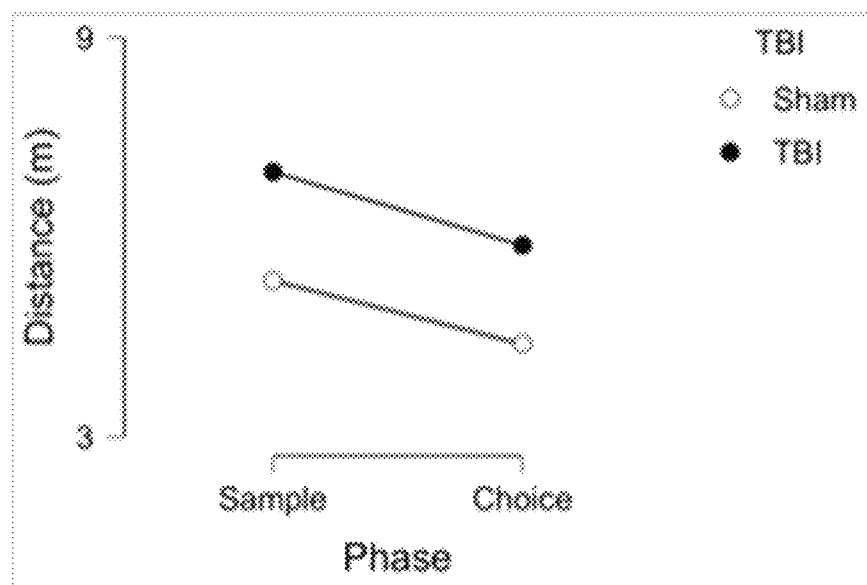
FIG. 20 shows that saline-treated rats swam a shorter distance in the choice phase vs the sample phase (P=0.008).

Next, the saline-treated ZDF rats were assessed for the effects of blood glucose concentrations after a single IP injection of peptide 2 (SEQ ID NO: 2). FIG. 18 shows that a single 2 mg/kg IP injection of peptide 2 (SEQ ID NO: 2) acutely increase (~11%) blood glucose in ZDF saline-treated rats. FIG. 19 shows a single 2 mg/kg IP injection of peptide 2 (SEQ ID NO: 2) acutely lowered (~10%) blood glucose in ZDF peptide-treated rats.

The response to hyperglycemia in the ZDF rats randomized to receive alternate daily peptide treatment is polyphagia in order to maintain a high body weight set point (Peptide group). Because the ZDF rats randomized to receive Saline had lower baseline blood glucose, they were able to maintain high body weight set point with normophagia. A single IP injection of peptide 2 (SEQ ID NO: 2) causes acute blood glucose-lowering in the polyphagic ZDF Peptide subgroup because it suppresses food intake. On the other hand, a single dose of peptide 2 (SEQ ID NO: 2) has no significant effect (or increased) blood glucose concentration in normophagic ZDF Saline subgroup because food intake was not abnormally high at baseline in the Saline subgroup of ZDF rats.

In sum, these results suggest that the weight loss in obese, diabetic ZDF rats treated with peptide 2 (SEQ ID NO: 2) can be glucose-independent.

Example 8: Decoy Peptides Reduce Blood Pressure in Lean Zucker Rats

A single IP injection of 2 mg/kg of peptide 2 (SEQ ID NO: 2) was tested for its effects on blood pressure in Zucker lean rats. Blood pressure was determined as previously described (e.g., automated tail cuff methodology). In three of four lean Zucker rats (#1-#3), baseline blood pressure was normal and it was not significantly affected by a single IP injection of 2 mg/kg of peptide 2 (SEQ ID NO: 2). In Zucker lean rat #4, elevated baseline blood pressure was significantly reduced (both systolic and diastolic) by a single IP injection of 2 mg/kg peptide 2 (SEQ ID NO: 2). P value determined from Student's t-test.

TABLE 34

Effect of SEQ ID NO: 2 (IP injection) on DIASTOLIC blood pressure lowering in lean ZDF rats.

| | Blood Pressure | | |
| --- | --- | --- | --- |
| | Before Injection | 30 minutes after Injection | P-value |
| Zucker Lean #1 | 130/72 | 120/78 | NS |
| Zucker Lean #2 | 124/80 | 123/83 | NS |
| Zucker Lean #3 | 130/85 | 132/98 | NS |
| Zucker Lean #4 | 149/102 (n = 6) | 130/91 (n = 4) | <0.05 |

NS—not statistically significant.

Figure 21:
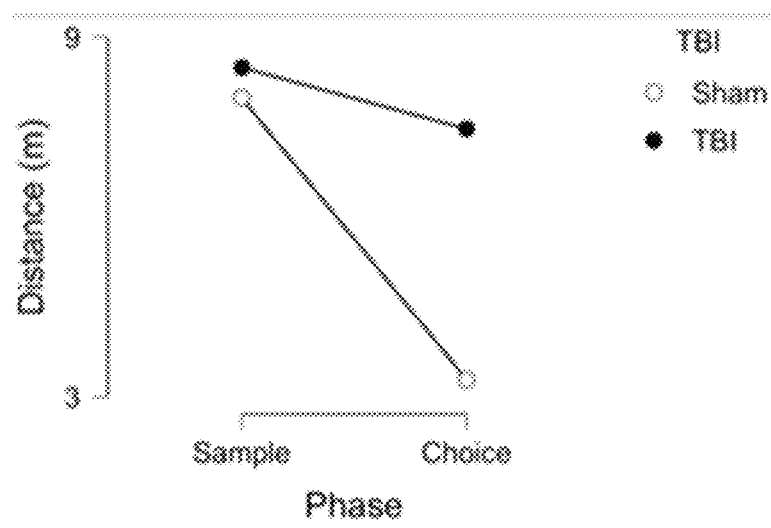
FIG. 21 shows that administration of peptide 2 (SEQ ID NO: 2) lead to a shorter distance traveled in the choice phase in rats with a sham injury compared to rats with a traumatic brain injury.

Example 9: Decoy Peptides Improve Short-Term Memory in Zucker Fatty and Zucker Lean Rats Morris water maze is a test of spatial memory. Zucker lean and Zucker diabetic fatty rats were randomly assigned to receive a lateral fluid percussion traumatic brain injury (TBI) or a sham injury. One week after traumatic brain injury or sham injury, the animals were tested for their ability to locate a submerged swim platform in a large swimming pool filled with water. During the training phase (sample phase), the rats learned to locate the platform, and during the testing phase (choice phase), the rats' learned spatial memory or recall of the platform location was tested by measuring the distance the rats swam prior to locating the platform. By measuring a shorter distance in the choice phase compared to the distance measuring in the sample phase is indicative of a spatial learning effect or increased short-term memory. FIG. 21 shows that saline-treated rats swam a significantly shorter distance during the choice phase compared to the sample phase.

Alternate daily IP peptide 2 (SEQ ID NO: 2) administration (2 mg/kg) for 1 week before and 1-week after traumatic brain injury or sham injury showed an improved performance in the sham injury rats, but not in the TBI rats as shown by the significantly shorter distance the sham rats needed to swim to locate the platform in the choice phase (FIG. 21). Compared to the saline-treated group, both sham and TBI animals needed to swim a longer distance in the sample (training phase) to locate the platform, but once they learned its position, the sham, peptide-treated rats located it more readily. These data show that administration of peptide 2 (SEQ ID NO: 2) leads to a 'spatial learning effect' in sham-injured Zucker fatty and Zucker lean rats.

Example 10: Decoy Peptides Reduces Weight Gain in Obese Diabetic Zucker Fatty Rats Intraperitoneal (IP) injection of 2 mg/kg dose of peptide 2 (SEQ ID NO: 2) in ZDF rats every other day for 7 days on two occasions over a 26-day period was assessed. The results show that administration of peptide 2 (SEQ ID NO: 2) caused a significant 'flattening of the curve' of progressive weight gain compared to age-matched, Zucker fatty rats (ZDF) who received an identical volume of IP saline on the same schedule.

Methods. Age-matched Zucker fatty diabetic rats (n=8) and Zucker lean rats (n=8) were randomly assigned to receive two 7-day periods of alternate daily IP dosing of either peptide 2 (SEQ ID NO: 2) or an equal volume of saline. Day 1 indicates one day prior to the first injections and Day 12 indicates the start of the second 7-day period of injections. The animals were weighed every 3-5 days for a 26 day observation period. The animals tolerated the procedure well. Days 12-15 corresponded to a period of anesthesia and recovery from either induced traumatic brain injury or sham injury in both fatty and lean Zucker rats. During this 3-4 day period the body weight leveled off in the subgroups but leveling off was most pronounced in the Zucker fatty rats who received alternate day dosing of peptide 2 (SEQ ID NO: 2), showing a mean net decrease in body weight for that short time period.

Figure 22:
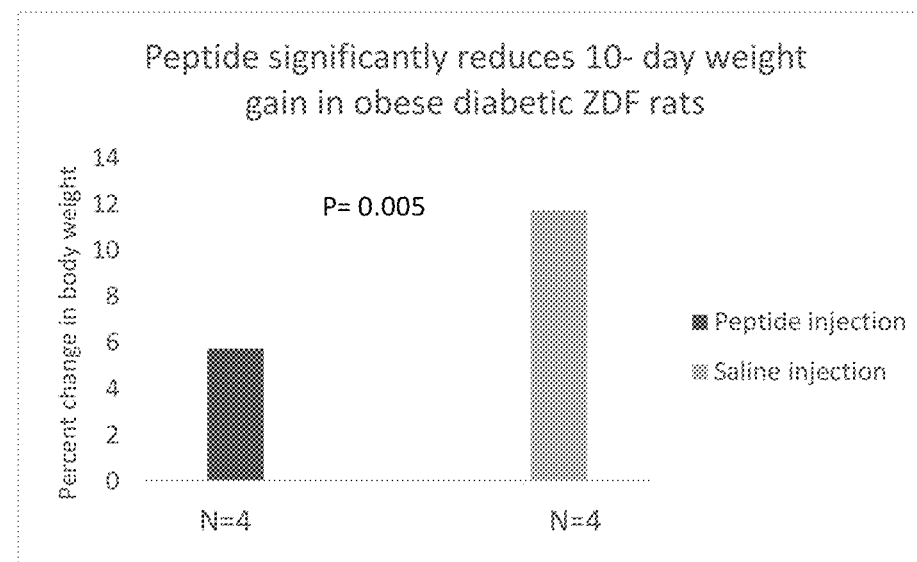
FIG. 22 shows the effects of the administration of peptide 2 (SEQ ID NO: 2) on body weight in Zucker fatty diabetic rats.
Figure 22:
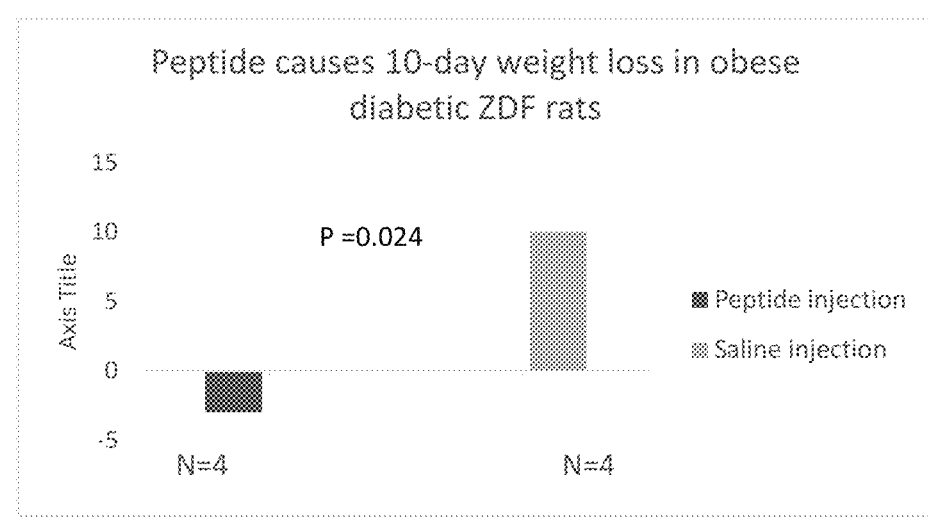
Figure 22:
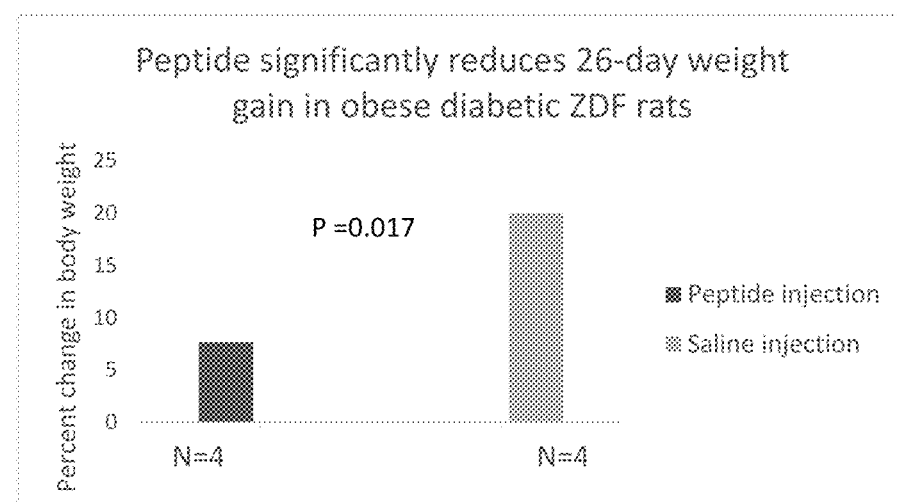
Figure 23:
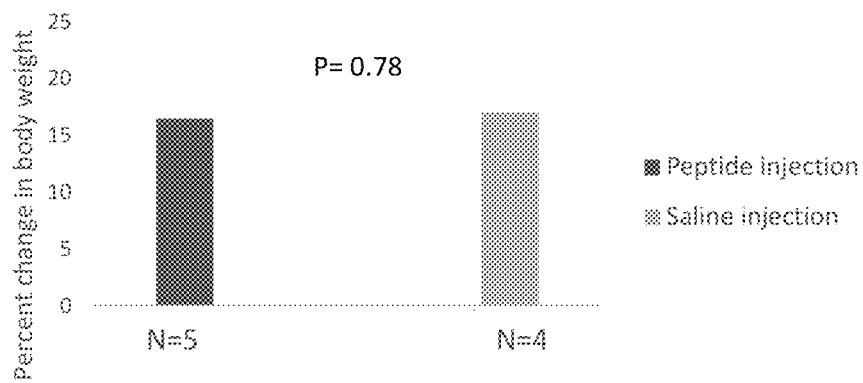
FIG. 23 shows the effects of the administration of peptide 2 (SEQ ID NO: 2) on body weight in Zucker lean rats.
Figure 23:
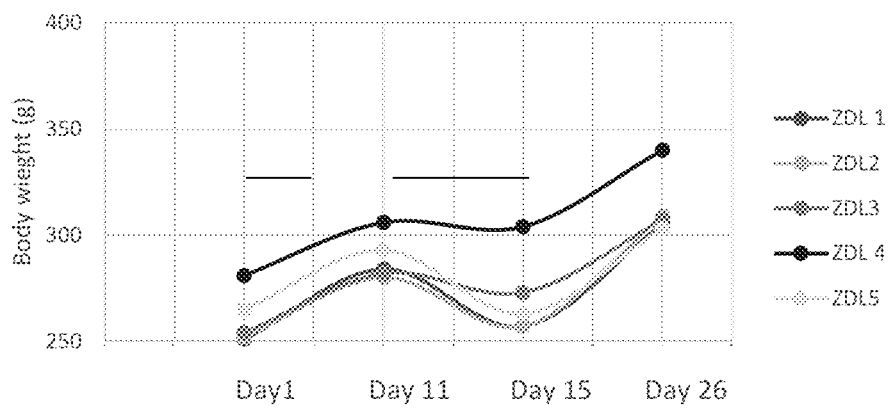
Figure 23:
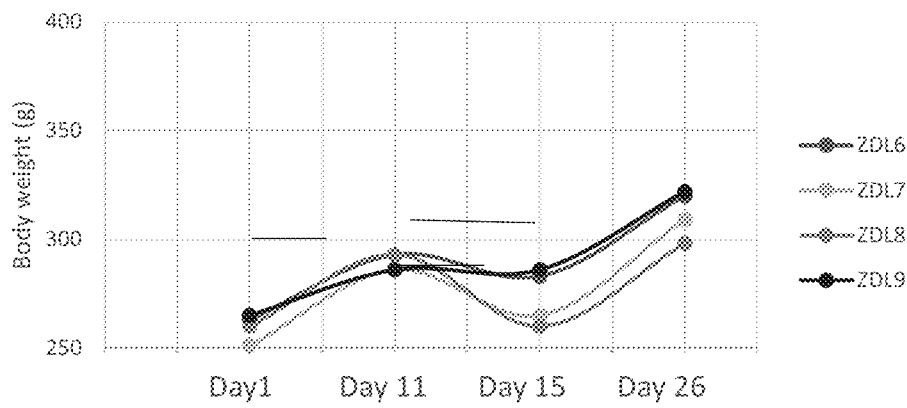
Figure 24A:
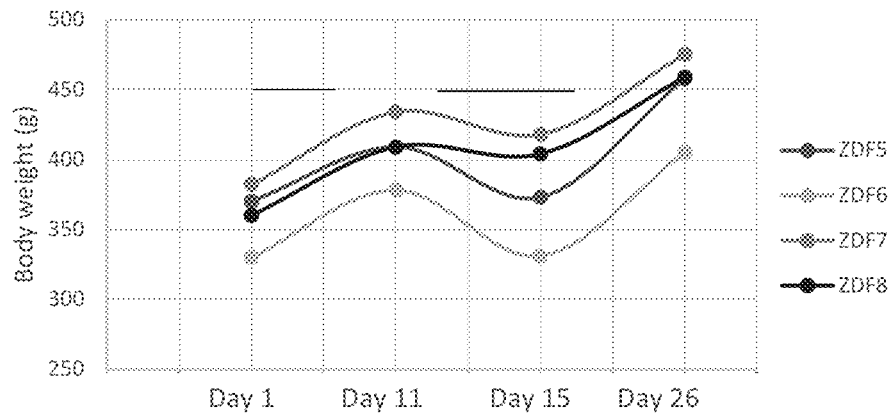
FIGS. 24A-B show no difference between 7-day, alternate day administration of (SEQ ID NO: 2) or saline doses on weight.
Figure 24B:
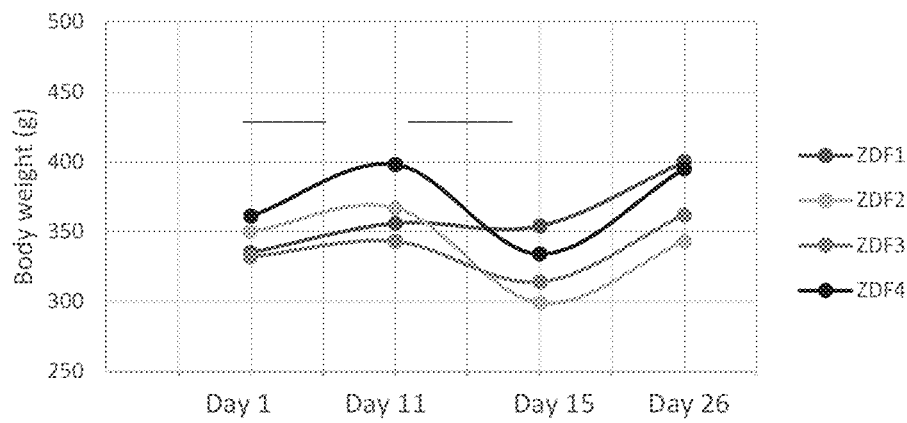

Results. Alternative daily IP dosing of 2 mg/kg peptide 2 (SEQ ID NO: 2) (for 7 days) was associated with a significantly smaller (P=0.005) increase in body weight in Zucker diabetic fatty rats over a 10-day observation period compared to IP injection of equal volume of sterile saline, given on alternate days for 7 days (FIG. 22, top panel). During and shortly after a second 7-day period of alternate daily IP dosing of 2 mg/kg of peptide 2 (SEQ ID NO: 2) or saline, peptide 2 (SEQ ID NO: 2) was associated with a significant decline (mean−2%) in body weight in ZDF rats compared to (mean+10%) increase in body weight in ZDF rats receiving saline (FIG. 22, middle panel). Comparison of percent change in body weight over the entire 26-day observation period that included both 7-day dosing intervals, the ZDF rats that received peptide 2 (SEQ ID NO: 2) gained significantly less weight (P=0.17) (e.g., approximately 7% body weight) compared to ZDF rats treated with saline (gained 20% body weight (FIG. 22, bottom panel)). Peptide 2 (SEQ ID NO: 2) or saline was administered on the same schedule in identical fashion in two groups of Zucker lean rats. As shown in FIG. 23, top panel, there was no significant difference (peptide 2 (SEQ ID NO: 2) vs saline) in the percent change in body weight over 26 days; both groups of rats gained approximately 16% body weight. Comparison of the trajectories of body weight in the two groups of Zucker lean rats (FIG. 23, middle panel and top panel) indicates that animals treated with either peptide 2 (SEQ ID NO: 2) or saline showed similar linear increases in body weight between days 1-11 and again from days 15-26. On the other hand, trajectories in Zucker fatty diabetic rats indicate that rats treated with saline (FIG. 24A) showed linear increases in body weight between days 1-11 and again from days 15-26, but Zucker diabetic fatty rats treated with peptide 2 (SEQ ID NO: 2) showed a "flattening of the curve" for progressive weight gain over the entire 26-day period (FIG. 24B).

Taken together, these data demonstrate that alternate daily IP dosing of 2 mg/kg of peptide 2 (SEQ ID NO: 2) promotes sustained reduction in weight gain in Zucker diabetic fatty rats compared to Zucker diabetic fatty rats treated on the same schedule with an equal volume of sterile saline.

Peptide 2 (SEQ ID NO: 2) is a decoy peptide corresponding to the active site of the 5HT2A receptor involved in binding to ligands such as the neurotransmitter serotonin or 5-HT2AR autoantibodies which are increased in the Zucker diabetic fatty rat. Although the mechanism is unknown, a closely related serotonin receptor 5-HT2C is known to be involved in appetite regulation via stimulation of the receptor in the lateral hypothalamus. Previous weight-loss medications have centered around drugs that increase 5-HT2C receptor activity. One possible explanation for the findings disclosed herein is that by binding to serotonin (the neurotransmitter involved in both 5-HT2A and 5-HT2C receptor signaling), the decoy peptide may alters the relative concentration of serotonin that is available to bind to 5-HT2A and 5-HT2C on neurons in the brain regions regulating appetite in favor of increased binding and activation of the known appetite-regulating 5-HT2C receptor. Another possibility to explain the findings disclosed herein is that administration of peptide 2 (SEQ ID NO: 2), which acts as a decoy of the 5HT2A receptor may result in an increase in sensation of nausea. Another serotonin receptor isoform, 5HT3, is known to be involved in the regulation of nausea and vomiting. 5-HT3 receptor antagonists are FDA approved for treatment of chemotherapy-induced nausea and vomiting. Thus alteration in the balance of serotonin signaling available to activate 5-HT3 receptor by the peptide 2 (SEQ ID NO: 2) may also contribute to slowing of weight gain in the Zucker diabetic fatty rat.

The ZDF rats treated with the 'weight-reducing' peptide 2 (SEQ ID NO: 2) did not experience vomiting or any other side effects during and for 15 days after the drug administration.

Figure 25A:
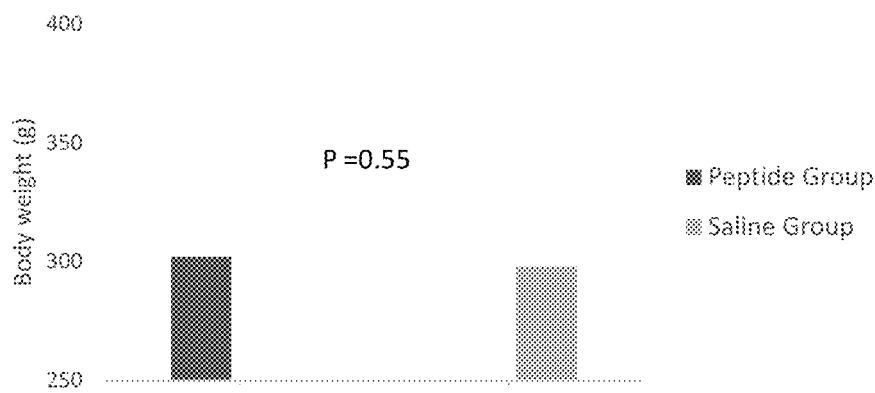
FIGS. 25A-B show body weight measurements and blood glucose concentrations in two groups of ZDF rats that received peptide 2 (SEQ ID NO: 2) or saline injections.
Figure 25B:
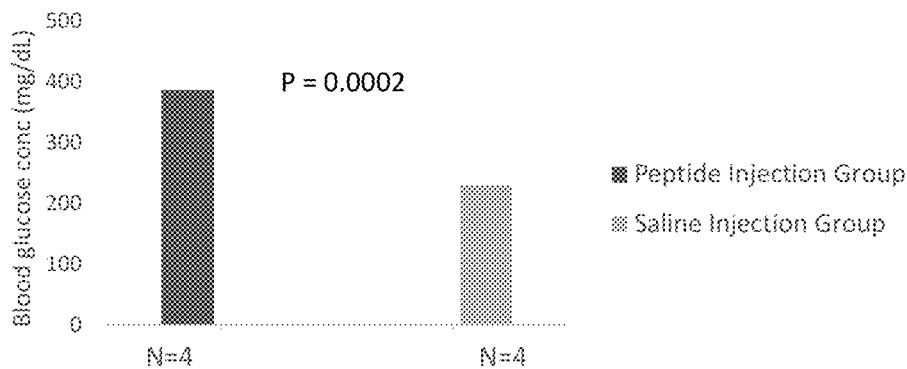

Despite having significantly higher blood glucose at baseline (see, FIG. 25B), ZDF rats that went on to receive to peptide 2 (SEQ ID NO: 2) injection were able to defend their body weight maintaining a similar average baseline weight (at the start of the experiment) as in the ZDF rats who received saline injections (see, FIG. 25A). Two conclusions can be drawn from this observation: 1) there is no evidence that the peptide injections caused a significant increase in blood glucose concentration; and 2) subsequent differences in body weight that arose between the ZDF experimental group (peptide) and control group (saline) were likely to be substantially due to the peptide injections themselves and that baseline differences in glucose level may have played a minor, if any role.

Figure 26A:
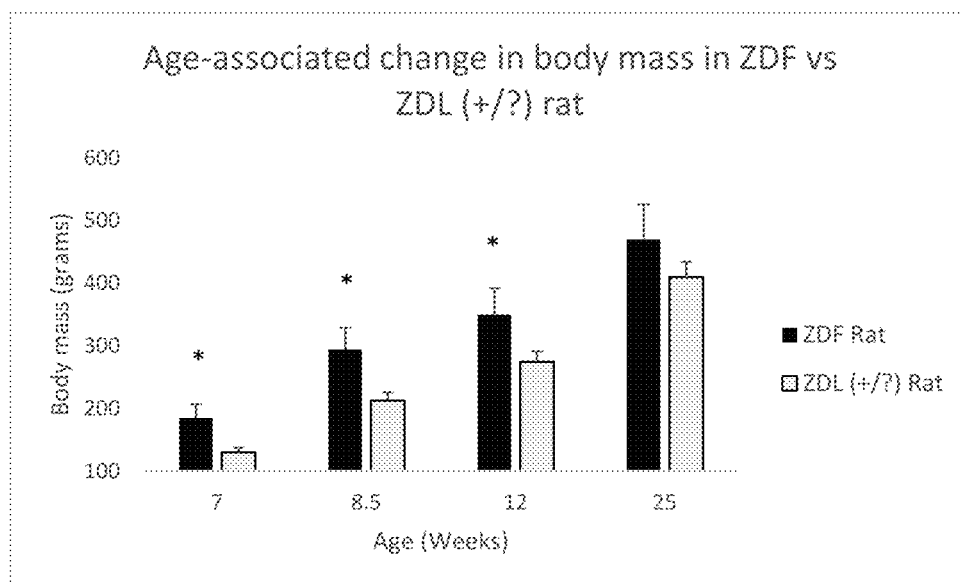
FIGS. 26A-B show age-associated changes in body mass and blood glucose in Zucker diabetic fatty rats compared to Zucker diabetic lean rats.
Figure 26B:
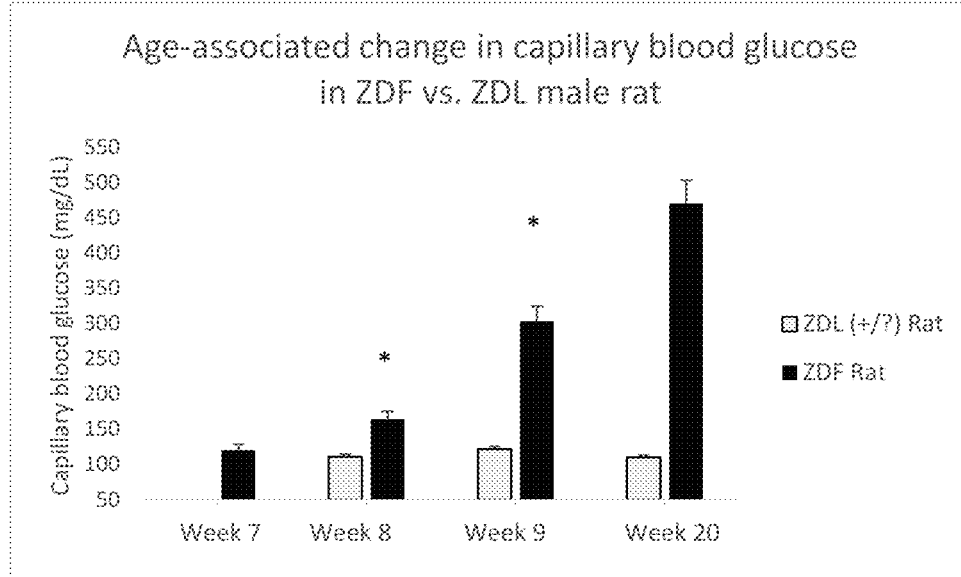

Based on the following analysis of normative body weight data in a different cohort of similarly-aged ZDF rats who were not treated with any of the peptide disclosed herein or with saline injections, it is concluded that baseline difference in initial blood glucose concentration in peptide vs. saline groups played a minor if any role in the emerging different pattern of weight gain in the two group shown in FIGS. 22-24. Specifically, as shown in FIGS. 26A-B, the 12-week-old ZDF rat weighing approximately 350 g already has an average blood glucose between 300 and 470 mg/dL. Yet despite the very high blood glucose concentrations, the UNTREATED ZDF rat at this age gains weight much more rapidly (+13-14% week 11-14.5 vs. +7.65%) than in the peptide-treated rats) at a similar developmental age (shown in Tables 35 and 36, UNTREATED, TREATED).

TABLE 35

Normative ranges of body weight increase and blood glucose concentration in Zucker diabetic fatty rats not exposed to peptide injections compared to treated ZDF rat at similar age of development. Percent increase in body weight per 26-day period

| | UNTREATED | |
| --- | --- | --- |
| | Fatty diabetic 1. | Fatty diabetic 2 |
| Week 8.5-12 | 16% | 22% |
| Week 11-14.5 | 14% | 13% |
| | TREATED | |
| | Peptide-treated (N = 4) | Saline-treated (N = 4) |
| Week 11-14.5 | 7.65% | 20% |

Figure 27:
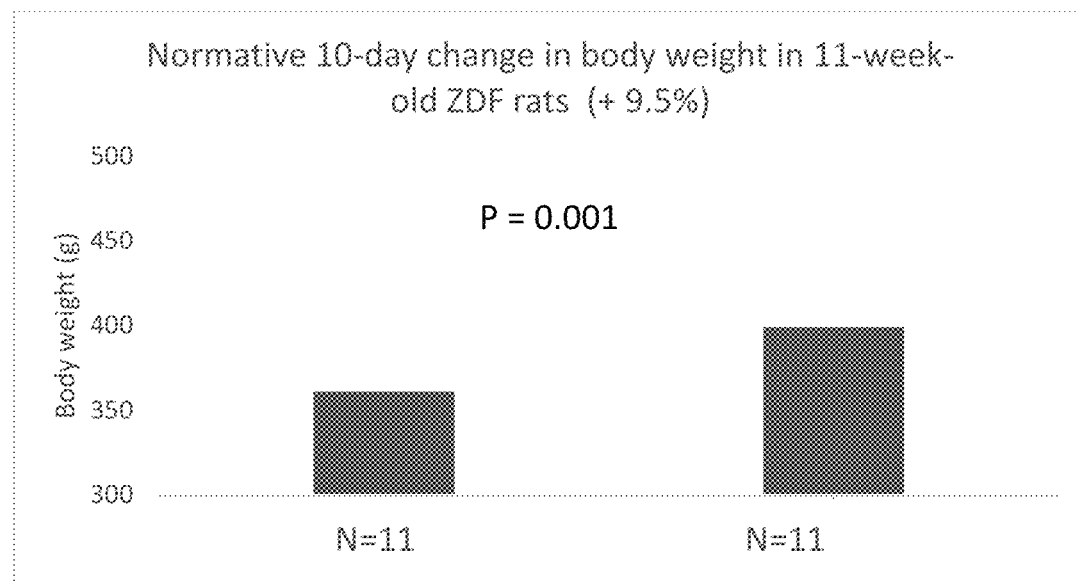
FIG. 27 shows normative 10-day change in body weight in 11 week old ZDF rats.

As shown in FIG. 27, Table 36 shows normative weight gain over a 10-day period (11-12.5 weeks of age) in untreated ZDF rats averaged 9.5%, much higher than the +5.75% for the peptide-treated ZDF rats.

TABLE 36

Normative ranges of body weight increase over a 10-day period. Percent increase in body weight per ~10-day period

| | UNTREATED (N = 11 ZDF RATS) | |
| --- | --- | --- |
| Week 11-12.5 | | 9.5% |
| | TREATED | |
| | Peptide-treated (N = 4) | Saline-treated (N = 4) |
| Week 11-12.5 | 5.75% | 11.75% |

Taken together, in a larger group of untreated ZDF rats (N=11) the normative values for weight gain at a similar developmental age as when the peptide vs saline experiment was initiated more closely resembled those of the saline-treated ZDF rats. These data shows that the apparent weight-reducing effect of the peptide injections is not likely to be due to higher baseline glucose concentrations in the rats who were randomized to receive peptide injections.

What is claimed is:

1. A decoy peptide consisting of the sequence of QDD-SKVFKEGSCLLADDN (SEQ ID NO: 1), or a fragment thereof, wherein the fragment of SEQ ID NO: 1 consists of 4 to 9 amino acids in length, and wherein the decoy peptide inhibits the binding of 5-HT2A receptor autoantibodies to a second extracellular loop region of the 5-HT2A receptor.

2. The decoy peptide of claim 1, wherein the fragment of SEQ ID NO: 1 consists of the sequence SCLLADDN (SEQ ID NO: 2), QDDSKVF (SEQ ID NO: 3), or VFKEGSC (SEQ ID NO: 4).

3. The decoy peptide of claim 1, wherein the decoy peptide inhibits the binding of a 5-HT2A receptor autoantibodies to a second extracellular loop region of the 5-HT2A receptor by competitive inhibition.

4. The decoy peptide of claim 1, wherein at least one amino acid residue of the decoy peptide comprises an acetyl group, a fluorenylmethoxy carbonyl group, a formyl group, a palmitoyl group, a myristyl group, a stearyl group, or polyethylene glycol.

5. A pharmaceutical composition comprising the decoy peptide of claim 1, and a pharmaceutically acceptable carrier.

6. A method of treating a subject with a disease or disorder, the method comprising: administering to the subject a therapeutically effective amount of a pharmaceutical composition comprising a decoy peptide comprising the sequence of SEQ ID NO: 2 and a pharmaceutically acceptable carrier, wherein the disease or disorder is a metabolic disease or disorder, a cardiovascular or a microvascular disease or disorder, or a neurodegenerative disease or disorder.

7. The method of claim 6, wherein the cardiovascular or the microvascular disease or disorder is a stroke, kidney dysfunction, kidney failure, age-related macular degeneration, diabetic macular edema, diabetic nephropathy, microvascular angiopathy, hypertension, painful neuropathy, or hypertensive nephropathy.

8. The method of claim 6, wherein the neurodegenerative disease or disorder is open angle glaucoma, dementia, Parkinson's disease, macular degeneration, or retinal degeneration.

9. The method of claim 6, wherein the metabolic disease or disorder is diabetes.

10. The method of claim 6, wherein the subject is obese or has a traumatic brain injury, type 2 diabetes, hypertension, microvascular angiopathy, painful neuropathy, Parkinson's disease, dementia, major depressive disorder, schizophrenia, retinitis pigmentosa, refractory hypertension, mild cognitive dysfunction, primary open angle glaucoma or previously had a stroke or a traumatic brain injury or a combination thereof.

11. The method of claim 6, wherein the subject has one or more 5-HT2A receptor autoantibodies.

12. The method of claim 6, wherein administering to the subject a therapeutically effective amount of a pharmaceutical composition comprising a decoy peptide comprising SEQ ID NO: 2 and a pharmaceutically acceptable carrier lowers blood pressure in the subject.

13. The method of claim 6, wherein the administration of the therapeutically effective amount of the pharmaceutical composition promotes or induces weight loss in the subject or improves short term memory in the subject.

14. The method of claim 6, further comprising administering a therapeutically effective amount of ketanserin or volinanserin to the subject.

15. The method of claim 6, wherein at least one amino acid residue of the decoy peptide comprises an acetyl group, a fluorenylmethoxy carbonyl group, a formyl group, a palmitoyl group, a myristyl group, a stearyl group, or polyethylene glycol.

16. A method of treating a subject with a neurologic disease or disorder, the method comprising: administering to the subject a therapeutically effective amount of a pharmaceutical composition comprising a decoy peptide comprising the sequence of SEQ ID NO: 2 and a pharmaceutically acceptable carrier, wherein the neurologic disease or disorder is neuropathy, dementia, major depressive disorder or Parkinson's disease.

17. The method of claim 16, further comprising administering a therapeutically effective amount of ketanserin or volinanserin to the subject.

18. The method of claim 16, wherein at least one amino acid residue of the decoy peptide comprises an acetyl group, a fluorenylmethoxy carbonyl group, a formyl group, a palmitoyl group, a myristyl group, a stearyl group, or polyethylene glycol.

19. A method of inducing sedation in a subject, the method comprising administering to the subject a therapeutically effective amount of a pharmaceutical composition comprising a decoy peptide comprising SEQ ID NO: 2, and a pharmaceutically acceptable carrier.

20. The method of claim 19, wherein at least one amino acid residue of the decoy peptide comprises an acetyl group, a fluorenylmethoxy carbonyl group, a formyl group, a palmitoyl group, a myristyl group, a stearyl group, or polyethylene glycol.

* * * * *

SEQUENCE LISTING

```
<160> NUMBER OF SEQ ID NOS: 7

<210> SEQ ID NO 1
<211> LENGTH: 18
<212> TYPE: PRT
<213> ORGANISM: Artificial Sequence
<220> FEATURE:
<223> OTHER INFORMATION: Synthetic construct

<400> SEQUENCE: 1

Gln Asp Asp Ser Lys Val Phe Lys Glu Gly Ser Cys Leu Leu Ala Asp
1               5                   10                  15

Asp Asn

<210> SEQ ID NO 2
<211> LENGTH: 8
<212> TYPE: PRT
<213> ORGANISM: Artificial Sequence
<220> FEATURE:
```

```
<223> OTHER INFORMATION: Synthetic construct

<400> SEQUENCE: 2

Ser Cys Leu Leu Ala Asp Asp Asn
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic construct

<400> SEQUENCE: 3

Gln Asp Asp Ser Lys Val Phe
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic construct

<400> SEQUENCE: 4

Val Phe Lys Glu Gly Ser Cys
1               5

<210> SEQ ID NO 5
<211> LENGTH: 15
<212> TYPE: PRT
<213> ORGANISM: Artificial Sequence
<220> FEATURE:
<223> OTHER INFORMATION: Synthetic construct

<400> SEQUENCE: 5

Ser Lys Val Phe Lys Glu Gly Ser Cys Leu Leu Ala Asp Asp Asn
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: Synthetic construct

<400> SEQUENCE: 6

Lys Glu Gly Ser Cys Leu Leu Ala Asp
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is a serine or threonine
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is a valine or isoleucine
<220> FEATURE:
```

-continued

```
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 7

Glu Xaa Ala Ala Xaa Ala Ala Xaa Ala Ala
1               5                   10
```